US010259855B2

(12) United States Patent
Perales-Puchalt et al.

(10) Patent No.: US 10,259,855 B2
(45) Date of Patent: Apr. 16, 2019

(54) METHODS AND COMPOSITIONS FOR TREATING CANCER

(71) Applicant: The Wistar Institute of Anatomy and Biology, Philadelphia, PA (US)

(72) Inventors: Alfredo Perales-Puchalt, Philadelphia, PA (US); Jose R. Conejo-Garcia, Philadelphia, PA (US)

(73) Assignee: THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 0 days.

(21) Appl. No.: 15/515,442

(22) PCT Filed: Sep. 30, 2015

(86) PCT No.: PCT/US2015/053128
§ 371 (c)(1),
(2) Date: Mar. 29, 2017

(87) PCT Pub. No.: WO2016/054153
PCT Pub. Date: Apr. 7, 2016

(65) Prior Publication Data
US 2017/0226176 A1 Aug. 10, 2017

Related U.S. Application Data

(60) Provisional application No. 62/059,068, filed on Oct. 2, 2014, provisional application No. 62/202,824, filed on Aug. 8, 2015.

(51) Int. Cl.
| A61K 38/24 | (2006.01) |
| A61K 38/00 | (2006.01) |
| C07K 14/72 | (2006.01) |
| C07K 14/705 | (2006.01) |
| C07K 14/59 | (2006.01) |
| C07K 14/725 | (2006.01) |
| A61K 35/17 | (2015.01) |
| A61K 38/17 | (2006.01) |
| A61K 48/00 | (2006.01) |

(52) U.S. Cl.
CPC .............. *C07K 14/59* (2013.01); *A61K 35/17* (2013.01); *A61K 38/177* (2013.01); *A61K 38/1774* (2013.01); *A61K 38/24* (2013.01); *C07K 14/705* (2013.01); *C07K 14/7051* (2013.01); *C07K 14/70517* (2013.01); *C07K 14/70521* (2013.01); *C07K 14/70564* (2013.01); *C07K 14/70578* (2013.01); *A61K 38/00* (2013.01); *A61K 48/00* (2013.01); *C07K 2319/00* (2013.01); *C07K 2319/02* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| 5,702,702 | A | 12/1997 | Santoli et al. |
| 7,247,472 | B2 | 7/2007 | Wilson et al. |
| 7,696,179 | B2 | 4/2010 | Lieberman et al. |
| 7,803,611 | B2 | 9/2010 | Roelvink et al. |
| 8,546,535 | B2 | 10/2013 | Leuschner et al. |
| 2006/0247420 | A1 | 11/2006 | Coukos et al. |
| 2013/0287748 | A1 | 10/2013 | June et al. |
| 2013/0309258 | A1* | 11/2013 | June ............... A61K 35/17 424/184.1 |
| 2014/0161767 | A1 | 6/2014 | Leuschner et al. |
| 2014/0241983 | A1 | 8/2014 | Hu et al. |

FOREIGN PATENT DOCUMENTS

| WO | WO-2005/071093 | 8/2005 |
| WO | WO 2009/081170 | 7/2009 |
| WO | WO-2009/103741 | 8/2009 |
| WO | WO-2013/044225 | 3/2013 |
| WO | WO-2013/063019 | 5/2013 |
| WO | WO2016/073456 | 5/2016 |

OTHER PUBLICATIONS

Gust et al. 2008. Cell Communication and Signaling 6:3, 2008 (Year: 2008).*
Minegishi, T. et al., Expression of gonadotropin and activin receptor messenger ribonucleic acid in human ovarian epithelial neoplasms, Clinical Cancer Research, Jul. 2000, 6(7):2764-2770.
Wang, J. et al., Quantitative analysis of follicle-stimulating hormone receptor in ovarian epithelial tumors: a novel approach to explain the field effect of ovarian cancer development in secondary mullerian systems, International Journal of Cancer, Jan. 2003, 103(3):328-334.
Cesano, A. & Santoli, D., Two unique human leukemic T-cell lines endowed with a stable cytotoxic function and a different spectrum of target reactivity analysis and modulation of their lytic mechanisms, In Vitro Cellular & Developmental Biology, Sep. 1992, 28A(9/10):648-656.

(Continued)

*Primary Examiner* — Shulamith H Shafer
(74) *Attorney, Agent, or Firm* — Howson & Howson LLP; Colleen M. Schaller

(57) ABSTRACT

A nucleic acid sequence is provided that encodes a chimeric protein comprising a ligand that comprises a naturally occurring or modified follicle stimulating hormone sequence, e.g., an FSHp sequence, or fragment thereof, which ligand binds to human follicle stimulating hormone (FSH) receptor, linked to either (a) a nucleic acid sequence that encodes an extracellular hinge domain, a transmembrane domain, a co-stimulatory signaling region, and a signaling endodomain; or (b) a nucleic acid sequence that encodes a ligand that binds to NKG2D. The vector containing the nucleic acid sequence, the chimeric proteins so encoded, and modified T cells expressing the chimeric protein, as well as method of using these compositions for the treatment of FSHR-expressing cancers or tumor cells are also provided.

18 Claims, 17 Drawing Sheets
Specification includes a Sequence Listing.

(56) References Cited

OTHER PUBLICATIONS

Huang, B. et al., Modulation of NKG2D-ligand cell surface expression enhances immune cell therapy of cancer, Journal of Immunotherapy Apr. 2011, 34(3):289-296.
Kruse, C. A. et al., The human leukemic T-cell line, TALL-104, is cytotoxic to human malignant brain tumors and traffics through brain tissue: implications for local adoptive immunotherapy, Cancer Research, Oct. 2000, 60:5731-5739.
Geoerger, B. et al., Antitumor activity of a human cytotoxic T-cell line (TALL-104) in brain tumor xenografts, Neuro Oncology, Apr. 2000, 2(2):103-113.
Zou, W. et al., Stromal-derived factor-1 in human tumors recruits and alters the function of plasmacytoid precursor dendritic cells, Nature Medicine, Dec. 2001, 7(12):1339-1346.
Heublein, S. et al., The G-protein coupled estrogen receptor (GPER/GPR30) is a gonadotropin receptor dependent positive prognosticator in ovarian carcinoma patients, PLoS One, Aug. 2013, 8(8):e71791.
Laws, M.J., et al. Dysregulated estrogen receptor signaling in the hypothalamic-pituitary-ovarian axis leads to ovarian epithelial tumorigenesis in mice, PLoS Genetics, Mar. 2014, 10(3):e1004230.
Eruslanov, E. B. et al., Tumor-associated neutrophils stimulate T cell responses in early-stage human lung cancer, Journal of Clinical Investigation, Dec. 2014, 124(12):5466-5480.
Rutkowski, M. R. et al., Microbial driven TLR5-dependent signaling governs distal malignant progression through tumor-promoting inflammation, Cancer Cell, Jan. 2015, 27(1):27-40.
Stephen, T. L. et al., Transforming Growth Factor beta-Mediated Suppression of Antitumor T Cells Requires FoxP1 Transcription Factor Expression, Immunity, Sep. 2014, 41(3):427-439.
Ali, N. et al., Xenogeneic graft-versus-host-disease in NOD-scid IL-2Rgammanull mice display a T-effector memory phenotype, PLoS One, Aug. 2012, 7(8):e44219.
Harlin, H. et al., Chemokine expression in melanoma metastases associated with CD8+ T-cell recruitment, Cancer Research, Apr. 2009, 69(7):3077-3085.
Yokokawa, J. et al., Identification of novel human CTL epitopes and their agonist epitopes of mesothelin, Clinical Cancer Research, Sep. 2005, 11(17):6342-6351.
Rosati, S. F. et al., A novel murine T-cell receptor targeting NY-ESO-1, Journal of Immunotherapy, Apr. 2014, 37(3):135-146.
Carpenito, C. et al., Control of large, established tumor xenografts with genetically retargeted human T cells containing CD28 and CD137 domains, PNAS, Mar. 2009, 106(9):3360-3365.
Perales-Puchalt, A. et al., Follicle-Stimulating Hormone Receptor Is Expressed by Most Ovarian Cancer Subtypes and Is a Safe and Effective Immunotherapeutic Target, Clinical Cancer Research, Jan. 2017, 23(2):441-453.
Cubillos-Ruiz, J. R. et al., Blocking ovarian cancer progression by targeting tumor microenvironmental leukocytes, Cell Cycle, Jan. 2010, 9(2):260-268.
International Search Report dated Dec. 28, 2015 in corresponding International Patent Application No. PCT/US15/53128.
Written Opinion dated Dec. 28, 2015 in corresponding International Patent Application No. PCT/US15/53128.
Zhang, X et al, Targeted paclitaxel nanoparticles modified with follicle-stimulating hormone β 81-95 peptide show effective anti-tumor activity against ovarian carcinoma. Jun. 2013, Internat. J Pharmaceutics, 453:498-505.
Scarlett, UK and Conejo-Garcia, JR, Modulating the tumor immune microenvironment as an ovarian cancer treatment strategy, Sep. 2012, Expert Rev. Obstet Gynecol, 7(5):413-419.
Urbanska, K. et al, Follicle-stimulating hormone receptor as a target in the redirected T-cell therapy for cancer. Oct. 2015, Cancer Immunol. Res., 3(10):1130-1137, publ online Jun. 25, 2015.
Ramos, RA and Dotti, G., Chimeric Antigen Receptor (CAR)-Engineered Lymphocytes for Cancer Therapy, Expert Opin Biol Ther., Jul. 2011, 11(7):855-873.
Radu, A. et al, Expression of Follicle-Stimulating Hormone Receptor in Tumor Blood Vessels, NEngl J. Medic, Oct. 2010, 363:1621-30.
Kang, TH et al, Control of spontaneous ovarian tumors by CD8+ T cells through NKG2D-targeted delivery of antigenic peptide. Cell & Biosci, Dec. 2013, 3:48.
Cartellieri, M. et al, Chimeric Antigen Receptor-Engineered T Cells for Immunotherapy of Cancer, J. Biomed Biotech, vol. 2010, Art ID 954304.
Coukos, J. R. et al, Immunotherapy for gynecological malignancies, Expert Opin Biol Ther, Sep. 2005, 5(9):1193-210.
International Preliminary Report on Patentability, dated Apr. 13, 2017, in corresponding International Patent Application No. PCT/US2015/053128, filed Sep. 30, 2015.
Siegel, R. et al., Cancer statistics, 2014, CA Cancer J Clin, Jan. 2014, 64(1):9-29.
Curiel, T.J. et al., Specific recruitment of regulatory T cells in ovarian carcinoma fosters immune privilege and predicts reduced survival, Nature Medicine, Sep. 2004, 10(9):942-949.
Zhang, L. et al., Intratumoral T cells, recurrence, and survival in epithelial ovarian cancer, The New England Journal of Medicine, Jan. 2003, 348(3):203-213.
Cubillos-Ruiz, J. R. et al., Polyethylenimine-based siRNA nanocomplexes reprogram tumor-associated dendritic cells via TLR5 to elicit therapeutic antitumor immunity, The Journal of Clinical Investigation, Aug. 2009, 119(8):2231-2244.
Cubillos-Ruiz, J. R. et al., cd277 is a Negative Co-stimulatory Molecule Universally Expressed by Ovarian Cancer Microenvironmental Cells, Oncotarget, Sep. 2010, 1(5):329-338.
Huarte, E. et al., Depletion of dendritic cells delays ovarian cancer progression by boosting anti-tumor immunity, Cancer Res, Sep. 2008, 68(18):7684-7691.
Nesbeth, Y. et al., CCL5-mediated endogenous antitumor immunity elicited by adoptively transferred lymphocytes and dendritic cell depletion, Cancer Res, Aug. 2009, 69(15):6331-6338.
Scarlett, U. K. et al., In situ stimulation of CD40 and Toll-like receptor 3 transforms ovarian cancer-infiltrating dendritic cells from immunosuppressive to immunostimulatory cells, Cancer Res, Sep. 2009, 69(18):7329-7337.
Scarlett, U. K. et al., Ovarian cancer progression is controlled by phenotypic changes in dendritic cells, The Journal of Experimental Medicine, Mar. 2012, 209(3):495-506.
Cubillos-Ruiz, J. R. et al., Reprogramming tumor-associated dendritic cells in vivo using microRNA mimetics triggers protective immunity against ovarian cancer, Cancer Res, Apr. 2012, 72(7):1683-1693.
Porter, D. L. et al., Chimeric antigen receptor-modified T cells in chronic lymphoid leukemia, The New England Journal of Medicine, Aug. 2011, 365(8):725-733.
Maus, M. V. et al., Antibody-modified T cells: CARs take the front seat for hematologic malignancies, Blood, Apr. 2014, 123(17):2625-2653.
Kalos, M., et al. T cells with chimeric antigen receptors have potent antitumor effects and can establish memory in patients with advanced leukemia, Sci Transl Med, Aug. 2011, 3(95):95ra73.
Simoni, M. et al., The follicle-stimulating hormone receptor: biochemistry, molecular biology, physiology, and pathophysiology, Endocrine Reviews, Dec. 1997, 18(6):739-773.
Vannier, B. et al., Anti-human FSH receptor monoclonal antibodies: immunochemical and immunocytochemical characterization of the receptor, Biochemistry, Feb. 1996, 35(5):1358-1366.
Zhang, X. Y. et al., Follicle-stimulating hormone peptide can facilitate paclitaxel nanoparticles to target ovarian carcinoma in vivo, Cancer Res, Aug. 2009, 69(16):6506-6514.
Al-Timimi, A. at al., An immunohistochemical study of the incidence and significance of human gonadotrophin and prolactin binding sites in normal and neoplastic human ovarian tissue, Br J Cancer, Mar. 1986, 53(3):321-329.
Ramakrishna, V. et al., Naturally occurring peptides associated with HLA-A2 in ovarian cancer cell lines identified by mass spectrometry are targets of HLA-A2-restricted cytotoxic T cells, International Immunology, Jun. 2003, 15(6):751-763.

(56) References Cited

OTHER PUBLICATIONS

Choi, J. H. et al., Overexpression of follicle-stimulating hormone receptor activates oncogenic pathways in preneoplastic ovarian surface epithelial cells, The Journla of Endocrinology and Metabolism, Nov. 2004, 89(11):5508-5516.
Jemal, A. et al., Cancer statistics, 2009, CA Cancer J Clin, Jul. 2009, 59(4):225-249.
Jemal, A. et al., Cancer statistics, 2008, CA Cancer J Clin, Mar. 2008, 58(2):71-96.
Conejo-Garcia, J. R. et al., Ovarian carcinoma expresses the NKG2D ligand Letal and promotes the survival and expansion of CD28- antitumor T Cells, Cancer Research, Mar. 2004, 64:2175-2182.
Hamanishi, J. et al., Programmed cell death 1 ligand 1 and tumor-infiltrating CD8+ T lymphocytes are prognostic factors of human ovarian cancer, PNAS, Feb. 2007, 104(9):3360-3365.
Sato, E. et al., Intraepithelial CD8+ tumor-infiltrating lymphocytes and a high CD8+/regulatory T cell ratio are associated with favorable prognosis in ovarian cancer, PNAS, Dec. 2005, 102(51):18538-18543.
Urba, W. J. & Longo, D. L., Redirecting T cells, The New England Journal of Medicine, Aug. 2011, 365(8):754-757.
Maude, S. L. et al., Chimeric antigen receptor T cells for sustained remissions in leukemia, The New England Journal of Medicine, Oct. 2014, 371(16):1507-1517.
Huarte, E. et al., PILAR is a novel modulator of human T-cell expansion, Blood, Aug. 2008, 112(4):1259-1268.
Lamers, C. H. et al., Immune responses to transgene and retroviral vector in patients treated with ex vivo-engineered T cells, Blood, Jan. 2011, 117(1):72-82.
Maus, M. V. et al., T cells expressing chimeric antigen receptors can cause anaphylaxis in humans, Cancer Immunology Research, Jul. 2013, 1(1):26-31.
Conejo-Garcia, J. R. et al., Tumor-infiltrating dendritic cell precursors recruited by a beta-defensin contribute to vasculogenesis under the influence of Vegf-A, Nature Medicine, Sep. 2004, 10(9):950-958.
Rutkowski, M. R. et al., Initiation of metastatic breast carcinoma by targeting of the ductal epithelium with adenovirus-cre: a novel transgenic mouse model of breast cancer, Journal of Visualized Experiments, Mar. 2014, 85:e51171.
Song, D. G. et al., In vivo persistence, tumor localization, and antitumor activity of CAR-engineered T cells is enhanced by costimulatory signaling through CD137 (4-1BB), Cancer Res, Jul. 2011, 71(13):4617:4627.
Milone, M. C. et al., Chimeric receptors containing CD137 signal transduction domains mediate enhanced survival of T cells and increased antileukemic efficacy in vivo, Molecular Therapy, Aug. 2009, 17(8):1453-4464.
Heslop, H. E. et al., Long-term outcome of EBV-specific T-cell infusions to prevent or treat EBV-related lymphoproliferative disease in transplant recipients, Blood, Feb. 2010, 115(5:):925-935.
Scholler, J. et al., Decade-long safety and function of retroviral-modified chimeric antigen receptor T cells, Sci Transl Med, May 2012, 4(132):132ra53.
Biasco, L. et al., Integration profile of retroviral vector in gene therapy treated patients is cell-specific according to gene expression and chromatin conformation of target cell, EMBO Molecular Medicine, Feb. 2011, 3(2):89-101.
Brentjens, R. J. & Curran, K. J., Novel cellular therapies for leukemia: CAR-modified T cells targeted to the CD19 antigen, American Society of Hematology, Dec. 2012, 2012(1):143-151.
Hollyman, D. et al., Manufacturing validation of biologically functional T cells targeted to CD19 antigen for autologous adoptive cell therapy, J Immunother, Feb. 2009, 32(2):169-180.
Pule, M. A. et al., Virus-specific T cells engineered to coexpress tumor-specific receptors: persistence and antitumor activity in individuals with neuroblastoma, Nature Medicine, Nov. 2008, 14(11)1264-1270.

Nesbeth, Y.C. et al., CD4+ T cells elicit host immune responses to MHC class II-ovarian cancer through CCL5 secretion and CD40-mediated licensing of dendritic cells, The Journal of Immunology, May 2010, 184(10):5654-5662.
Porter, D. L. et al., A phase 1 trial of donor lymphocyte infusions expanded and activated ex vivo via CD3/CD28 costimulation, Blood, Feb. 2006, 107(4):1325-1331.
Terakura, S. et al., Generation of CD19-chimeric antigen receptor modified CD8+ T cells derived from virus-specific central memory T cells, Blood, Jan. 2012, 119(1):72-82.
Maines-Bandiera, S. L. et al., Epithelio-mesenchymal transition in a neoplastic ovarian epithelial hybrid cell line, Differentiation, May 2004, 72(4):150-161.
Ritchie, D. S. et al., Persistence and efficacy of second generation CAR T cell against the LeY antigen in acute myeloid leukemia, Molecular Therapy, Nov. 2013, 21(11):2122-2129.
Amatangelo, M. D. et al., Three-dimensional culture sensitizes epithelial ovarian cancer cells to EZH2 methyltransferase inhibition, Cell Cycle, Jul. 2013, 12(13):2113-2119.
Nesbeth, Y. & Conejo-Garcia, J. R., Harnessing the effect of adoptively transferred tumor-reactive T cells on endogenous (host-derived) antitumor immunity, Clinical and Developmental Immunology, Nov. 2010, 2010(139304):1-11.
Siraj, A. et al., Expression of follicle-stimulating hormone receptor by the vascular endothelium in tumor metastases, BMC Cancer, May 2013, 13(246):1-8.
Mariani, S. et al., Expression and cellular localization of follicle-stimulating hormone receptor in normal human prostate, benign prostatic hyperplasia and prostate cancer, The Journal of Urology, Jun. 2006, 175(6):2072-2077.
Walker, J. L. et al., Intraperitoneal catheter outcomes in a phase III trial of intravenous versus intraperitoneal chemotherapy in optimal stage III ovarian and primary peritoneal cancer: a Gynecologic Oncology Group Study, Gynecologic Oncology, Jan. 2006, 100(1):27-32.
Lee, D. W. et al., T cells expressing CD19 chimeric antigen receptors for acute lymphoblastic leukaemia in children and young adults: a phase 1 dose-escalation trial, Lancet, Oct. 2014, 385(9967):517-528.
Grupp, S. A. et al., Chimeric antigen receptor-modified T cells for acute lymphoid leukemia, The New England Journal of Medicine, Apr. 2013, 368(16):1509-1518.
Teachey, D. T. et al., Cytokine release syndrome after blinatumomab treatment related to abnormal macrophage activation and ameliorated with cytokine-directed therapy, Blood, Jun. 2013, 121(26):5154-5157.
Barber., A. et al., Chimeric NKG2D receptor-bearing T cells as immunotherapy for ovarian cancer, Cancer Research, May 2007, 67(10):5003-5008.
Brando, C. et al., Receptors and lytic mediators regulating anti-tumor activity by the leukemic killer T cell line TALL-104, Journal of Leukocyte Biology, Aug. 2005, 78(2):359-371.
Visonneau, S. et al., Phase I trial of TALL-104 cells in patients with refractory metastatic breast cancer, Clinical Cancer Research, May 2000, 6(5):1744-1754.
Sadelain, M. et al., The basic principles of chimeric antigen receptor (CAR) design, Cancer Discovery, Apr. 2013, 3(4):388-398.
Conejo-Garcia, J. et al., Letal, A Tumor-Associated NKG2D Immunoreceptor Ligand, Induces Activation and Expansion of Effector Immune Cells, Cancer Biology and Therapy, Jul. 2003, 2(4):446-451.
Manjunath, N. et al., Lentiviral delivery of short hairpin RNAs, Adv Drug Deliv Rev, Jul. 2009, 61(9):732-745.
Lauer, P. et al., Constitutive Activation of the PrfA Regulon Enhances the Potency of Vaccines Based on Live-Attenuated and Killed but Matabolically Active Listeria monocytogenes Strains, Aug. 2008, 76(8):3742-3753.
Hall, J. E., Neuroendrocrine changes with reproductive aging in women, Seminars in Reproductive Medicine, Sep. 2007, 25(5):344-351.
Ellis, J. M. et al., Frequencies of HLA-A2 alleles in five U.S. population groups, Predominance of A*02011 and identification of HLA-A*0231, Hum Immunol, Mar. 2000, 61(3):334-340.

(56) References Cited

OTHER PUBLICATIONS

International Preliminary Report on Patentability dated Apr. 4, 2017 in corresponding International Patent Application No. PCT/US15/53128.

Gartrell, BA et al, The follicle-stimulating hormone receptor:A novel target in genitourinary malignancies. Urol. Oncol: Simiars and Origl Invest., Nov. 2013, 31(8):1403-1407.

George, JW et al., Current concepts of fillicle-stimulating hormone receptor gene regulation., Biol. Reproduc. Jan. 2011, 84(1):7-17.

Cui, J et al, Regulation of gene expression in ovarian cancer cells by luteinizing hormone receptor expression and activation, BMC Cancer, Jun. 2011, 11(1):280.

Communication and Extended European Search Report, dated Mar. 22, 2018 in corresponding European patent application No. 15847792.7.

Arcangeli S et al. Balance of Anti-CD123 Chimeric Antigen Receptor Binding Affinity and Density for the Targeting of Acute Myeloid Leukemia. Aug. 2, 2017; 25(8):1933-45. Epub May 4, 2017.

Curran KJ et al. Chimeric antigen receptors for T cell immunotherapy: current understanding and future directions. J Gene Med. Jun. 2012; 14(6):405-15.

Fan QR and Hendrickson WA. Structure of human follicle-stimulating hormone in complex with its receptor. Nature. Jan. 20, 2005; 433(7023):269-77.

Gacerez AT et al. How chimeric antigen receptor design affects adoptive T cell therapy. Cell Physiol. Dec. 2016; 231(12):2590-8. Epub Jun. 2, 2016.

Jensen MC and Riddell SR. Design and implementation of adoptive therapy with chimeric antigen receptor-modified T cells. Immunol Rev. Jan. 2014; 257(1):127-44.

Kahlon KS et al. Specific recognition and killing of glioblastoma multiforme by interleukin 13-zetakine redirected cytolytic T cells. Cancer Res. Dec. 15, 2004; 64(24):9160-6.

Norelli M et al. Clinical pharmacology of CAR-T cells: Linking cellular pharmacodynamics to pharmacokinetics and antitumor effects. Biochim Biophys Acta. Jan. 2016; 1865(1):90-100. Epub Dec. 31, 2015.

Sadelain M et al. The basic principles of chimeric antigen receptor design. Cancer Discov. Apr. 2013; 3(4):388-98. Epub Apr. 2, 2013.

Santoro S. "T cells bearing a chimeric antigen receptor against the tumor vasculature destroy the tumor endothelium and result in tumor regression" (2014) Dissertations available from ProQuest. AAI3670963.

\* cited by examiner

FIG. 5

```
atgaagacactccagttttt cttccttttctgttgctggaaagcaatctgctgcaatagc    60
 M  K  T  L  Q  F  F  F  L  F  C  C  W  K  A  I  C  C  N  S Tgtgagctgaccaacatcaccattgcaatagagaaagaagaatgtcgtttctgcataagc   120
 C  E  L  T  N  I  T  I  A  I  E  K  E  E  C  R  F  C  I  S Atcaacaccacttggtgtgctggctactgctacaccagggatctggtgtataaggaccca   180
 I  N  T  T  W  C  A  G  Y  C  Y  T  R  D  L  V  Y  K  D  P Gccaggcccaaaatccagaaaacatgtaccttcaaggaactggtatacgaaacagtgaga   240
 A  R  P  K  I  Q  K  T  C  T  F  K  E  L  V  Y  E  T  V  R Gtgcccggctgtgctcaccatgcagattccttgtatacatacccagtggccacccagtgt   300
 V  P  G  C  A  H  H  A  D  S  L  Y  T  Y  P  V  A  T  Q  C Cactgtggcaagtgtgacagcgacagcactgattgtactgtgcgaggcctggggcccagc   360
 H  C  G  K  C  D  S  D  S  T  D  C  T  V  R  G  L  G  P  S Tactgctcctttggtgaaatgaaagaaggtggtggttctggtggtggatccggtggtggt   420
 Y  C  S  F  G  E  M  K  E  G  G  G  S  G  G  G  S  G  G  G Tctggtggtggtgctcctgatgtgcaggagacagggtttcaccatgttgcccaggctgct   480
 S  G  G  G  A  P  D  V  Q  E  T  G  F  H  H  V  A  Q  A  A Ctcaaactcctgagctcaagcaatccacccactaaggcctcccaaagtgctaggattaca   540
 L  K  L  L  S  S  S  N  P  P  T  K  A  S  Q  S  A  R  I  T Gattgcccagaatgcacgctacaggaaaacccattcttctcccagccgggtgccccaata   600
 D  C  P  E  C  T  L  Q  E  N  P  F  F  S  Q  P  G  A  P  I Cttcagtgcatgggctgctgcttctctagagcatatcccactccactaaggtccaagaag   660
 L  Q  C  M  G  C  C  F  S  R  A  Y  P  T  P  L  R  S  K  K Acgatgttggtccaaaagaacgtcacctcagagtccacttgctgtgtagctaaatcatat   720
 T  M  L  V  Q  K  N  V  T  S  E  S  T  C  C  V  A  K  S  Y Aacagggtcacagtaatggggggtttcaaagtggagaaccacacggcgtgccactgcagt   780
 N  R  V  T  V  M  G  G  F  K  V  E  N  H  T  A  C  H  C  S Acttgttattatcacaaatctaccacgacgccagcgccgcgaccaccaacaccggcgccc   840
 T  C  Y  Y  H  K  S  T  T  T  P  A  P  R  P  P  T  P  A  P Accatcgcgtcgcagcccctgtccctgcgcccagaggcgtgccggccagcggcggggggc   900
 T  I  A  S  Q  P  L  S  L  R  P  E  A  C  R  P  A  A  G  G
```

FIG. 5 (cont'd)

```
Gcagtgcacacgagggggctggacttcgcctgtgatatctacatctgggcgcccttggcc  960
 A  V  H  T  R  G  L  D  F  A  C  D  I  Y  I  W  A  P  L  A Gggacttgtggggtccttctcctgtcactggttatcacccttactgcaaacggggcaga  1020
 G  T  C  G  V  L  L  S  L  V  I  T  L  Y  C  K  R  G  R aagaaactcctgtatatattcaaacaaccatttatgagaccagtacaaactactcaagag  1080
 K  K  L  Y  I  F  K  Q  P  F  M  R  P  V  Q  T  T  Q  E Gaagatggctgtagctgccgatttccagaagaagaagaaggaggatgtgaactgagagtg  1140
 E  D  G  C  S  C  R  F  P  E  E  E  G  G  C  E  L  R  V Aagttcagcaggagcgcagacgccccgcgtaccagcagggccagaaccagctctataac  1200
 K  F  S  R  S  A  D  A  P  A  Y  Q  Q  G  Q  N  Q  L  Y  N Gagctcaatctaggacgaagagaggagtacgatgttttggacaagagacgtggccgggac  1260
 E  L  N  L  G  R  R  E  E  Y  D  V  L  D  K  R  R  G  R  D Cctgagatgggggaaagccgagaaggaagaaccctcaggaaggcctgtacaatgaactg  1320
 P  E  M  G  G  K  P  R  R  K  N  P  Q  E  G  L  Y  N  E  L Cagaaagataagatggcggaggcctacagtgagattgggatgaaaggcgagcgccggagg  1380
 Q  K  D  K  M  A  E  A  Y  S  E  I  G  M  K  G  E  R  R  R Ggcaaggggcacgatggcctttaccagggtctcagtacagccaccaaggacacctacgac  1440
 G  K  G  H  D  G  L  Y  Q  G  L  S  T  A  T  K  D  T  Y  D gcccttcacatgcaggccctgcccctcgctaa                              1473
 A  L  H  M  Q  A  L  P  P  R  *
```

FIG. 6B

```
ATGaatagctgtgagctgaccaacatcaccattgcaatagagaagaagaatgtcgtttc
 M  N  S  C  E  L  T  N  I  T  I  A  I  E  K  E  E  C  R  F
tgcataagcatcaacaccacttggtgtgctggctactgctacaccagggatctggtgtat
 C  I  S  I  N  T  T  W  C  A  G  Y  C  Y  T  R  D  L  V  Y
aaggacccagccaggcccaaaatccagaaaacatgtaccttcaaggaactggtatacgaa
 K  D  P  A  R  P  K  I  Q  K  T  C  T  F  K  E  L  V  Y  E
acagtgagagtgcccggctgtgctcaccatgcagattccttgtatacatacccagtggcc
 T  V  R  V  P  G  C  A  H  H  A  D  S  L  Y  T  Y  P  V  A
acccagtgtcactgtggcaagtgtgacagcgacagcactgattgtactgtgcgaggcctg
 T  Q  C  H  C  G  K  C  D  S  D  S  T  D  C  T  V  R  G  L
gggcccagctactgctcctttggtgaaatgaaagaaggcggcggaagcggaggcggatct
 G  P  S  Y  C  S  F  G  E  M  K  E  G  G  G  S  G  G  G  S
gggggaggatctggcggcggagctcctgatgtgcaggagacagggtttcaccatgttgcc
 G  G  G  S  G  G  A  P  D  V  Q  E  T  G  F  H  H  V  A
caggctgctctcaaactcctgagctcaagcaatccacccactaaggcctcccaaagtgct
 Q  A  A  L  K  L  L  S  S  S  N  P  P  T  K  A  S  Q  S  A
aggattacagattgcccagaatgcacgctacaggaaaacccattcttctcccagccggt
 R  I  T  D  C  P  E  C  T  L  Q  E  N  P  F  F  S  Q  P  G
gccccaatacttcagtgcatgggctgctgcttctctagagcatatcccactccactaagg
 A  P  I  L  Q  C  M  G  C  C  F  S  R  A  Y  P  T  P  L  R
tccaagaagacgatgttggtccaaaagaacgtcacctcagagtccacttgctgtgtagct
 S  K  K  T  M  L  V  Q  K  N  V  T  S  E  S  T  C  C  V  A
aaatcatataacagggtcacagtaatggggggtttcaaagtggagaaccacacggcgtgc
 K  S  Y  N  R  V  T  V  M  G  G  F  K  V  E  N  H  T  A  C
cactgcagtacttgttattatcacaaatctggcggcggaagcggaggcggatctggggga
 H  C  S  T  C  Y  Y  H  K  S  G  G  G  S  G  G  G  S  G  G
ggatctggcggcggaaacttcactataaaatcattgtccagacctggacagccctggtgt
 G  S  G  G  G  N  F  T  I  K  S  L  S  R  P  G  Q  P  W  C
gaagcgcaggtcttcttgaataaaaatcttttccttcagtacaacagtgacaacaacatg
 E  A  Q  V  F  L  N  K  N  L  F  L  Q  Y  N  S  D  N  N  M
gtcaaacctctgggcctcctggggaagaaggtatatgccaccagcacttggggagaattg
 V  K  P  L  G  L  L  G  K  K  V  Y  A  T  S  T  W  G  E  L
acccaaacgctgggagaagtggggcgagacctcaggatgctcctttgtgacatcaaaccc
 T  Q  T  L  G  E  V  G  R  D  L  R  M  L  L  C  D  I  K  P
cagataaagaccagtgatccttccactctgcaagtcgagatgttttgtcaacgtgaagca
 Q  I  K  T  S  D  P  S  T  L  Q  V  E  M  F  C  Q  R  E  A
gaacggtgcactggtgcatcctggcagttcgccaccaatggagagaaatccctcctcttt
 E  R  C  T  G  A  S  W  Q  F  A  T  N  G  E  K  S  L  L  F
gacgcaatgaacatgacctggacagtaattaatcatgaagccagtaagatcaaggagaca
 D  A  M  N  M  T  W  T  V  I  N  H  E  A  S  K  I  K  E  T
tggaagaaagacagagggctggaaaagtatttcaggaagctctcaaagggagactgcgat
 W  K  K  D  R  G  L  E  K  Y  F  R  K  L  S  K  G  D  C  D
cactggctcagggaattctagggcactggaggcaatgccagaaccgacagtgtcacca
 H  W  L  R  E  F  L  G  H  W  E  A  M  P  E  P  T  V  S  P
gtaaatgcttcagatatccactggtcttcttctagtctaccaTAG
 V  N  A  S  D  I  H  W  S  S  S  S  L  P  Stop
```

FIG. 6C

```
ATGcacagctgcgagctgaccaacatcaccatcagcgtggaaaagaggaatgccggttctgcatc
 M  H  S  C  E  L  T  N  I  T  I  S  V  E  K  E  E  C  R  F  C  I
agcatcaacaccacttggtgcgccggctactgctacacccgggacctggtgtacaaggac
 S  I  N  T  T  W  C  A  G  Y  C  Y  T  R  D  L  V  Y  K  D
cccgccagacccaacacccagaaagtgtgcaccttcaaagaactggtgtacgagacagtg
 P  A  R  P  N  T  Q  K  V  C  T  F  K  E  L  V  Y  E  T  V
cggctgccggctgtgccagacacagcgatagcctgtacacctaccccgtggccaccgag
 R  L  P  G  C  A  R  H  S  D  S  L  Y  T  Y  P  V  A  T  E
tgccactgcggcaagtgtgacagcgacagcaccgactgtaccgtgcggggactgggccct
 C  H  C  G  K  C  D  S  D  S  T  D  C  T  V  R  G  L  G  P
agctactgcagcttcagcgagatgaaggaaggcggcggaagcggaggcggatctggggga
 S  Y  C  S  F  S  E  M  K  E  G  G  G  S  G  G  S  G  G
ggatctggcggcggagacttcattattcaaggctgccccgagtgcaagctgaaagagaac
 G  S  G  G  D  F  I  I  Q  G  C  P  E  C  K  L  K  E  N
aagtacttcagcaagctgggcgctcccatctaccagtgcatgggctgctgcttcagcaga
 K  Y  F  S  K  L  G  A  P  I  Y  Q  C  M  G  C  C  F  S  R
gcctaccccaccccgccagatccaagaaaaccatgctggtgcccaagaacatcacctcc
 A  Y  P  T  P  A  R  S  K  K  T  M  L  V  P  K  N  I  T  S
gaggccacctgttgcgtggccaaggccttcaccaaggccaccgtgatgggcaacgccaga
 E  A  T  C  C  V  A  K  A  F  T  K  A  T  V  M  G  N  A  R
gtggaaaaccacacagagtgtcactgcagcacctgttactaccacaagagcgctagc
 V  E  N  H  T  E  C  H  C  S  T  C  Y  Y  H  K  S  A  S
ggcggcggaagcggaggcggatctgggggaggatctggcggcgga
 G  G  G  S  G  G  G  S  G  G  G  S  G  G
ccaaggatagaagagactgcttctctttgtaacatttacaaggtt
 P  R  I  E  E  T  A  S  L  C  N  I  Y  K  V
aacaggtcagagtctggacaacatagtcatgaagttcaaggcctactcaacagacagcct
 N  R  S  E  S  G  Q  H  S  H  E  V  Q  G  L  L  N  R  Q  P
cttttgtctacaaggataaaaagtgtcatgccattggtgctcataggaacagcatgaat
 L  F  V  Y  K  D  K  K  C  H  A  I  G  A  H  R  N  S  M  N
gctacaaagatctgtgaaaagagggttgacactctgaaagatggaattgacattttcaaa
 A  T  K  I  C  E  K  E  V  D  T  L  K  D  G  I  D  I  F  K
ggtctgctgcttcacatagtgcaggagactaacacaaccggaaagccctcactctgcag
 G  L  L  L  H  I  V  Q  E  T  N  T  T  G  K  P  L  T  L  Q
gctgaggtgtgtggccagtatgaagtagacaaacatttcacaggatacgccattgttagc
 A  E  V  C  G  Q  Y  E  V  D  K  H  F  T  G  Y  A  I  V  S
ctcaatggaaagaatatattccgtgttgacacaagcactggcaactggacccaactggat
 L  N  G  K  N  I  F  R  V  D  T  S  T  G  N  W  T  Q  L  D
catgaattcgagaagtttatagaaatgtgcaaggaagacaaggttttagctgcttttta
 H  E  F  E  K  F  I  E  M  C  K  E  D  K  V  L  A  A  F  L
aagaagactacagagggcgactgcaggacctggcttgatgagctcatgttgcactggaaa
 K  K  T  E  G  D  C  R  T  W  L  D  E  L  M  L  H  W  K
GaacatctggagcctgcaggatctTAG
 E  H  L  E  P  A  G  S  Stop
```

FIG. 6D

```
ATGaatagctgtgagctgaccaacatcaccattgcaatagagaaagaagaatgtcgtttc
 M  N  S  C  E  L  T  N  I  T  I  A  I  E  K  E  E  C  R  F
tgcataagcatcaacaccacttggtgtgctggctactgctacaccagggatctggtgtat
 C  I  S  I  N  T  T  W  C  A  G  Y  C  Y  T  R  D  L  V  Y
aaggacccagccaggcccaaaatccagaaaacatgtaccttcaaggaactggtatacgaa
 K  D  P  A  R  P  K  I  Q  K  T  C  T  F  K  E  L  V  Y  E
acagtgagagtgcccggctgtgctcaccatgcagattccttgtatacatacccagtggcc
 T  V  R  V  P  G  C  A  H  H  A  D  S  L  Y  T  Y  P  V  A
acccagtgtcactgtggcaagtgtgacagcgacagcactgattgtactgtgcgaggcctg
 T  Q  C  H  C  G  K  C  D  S  D  S  T  D  C  T  V  R  G  L
gggcccagctactgctcctttggtgaaatgaaagaaggcggcggaagcggaggcggatct
 G  P  S  Y  C  S  F  G  E  M  K  E  G  G  G  S  G  G  G  S
gggggaggatctggcggcggagctcctgatgtgcaggattgcccagaatgcacgctacag
 G  G  G  S  G  G  G  A  P  D  V  Q  D  C  P  E  C  T  L  Q
gaaaacccattcttctcccagccgggtgccccaatacttcagtgcatgggctgctgcttc
 E  N  P  F  F  S  Q  P  G  A  P  I  L  Q  C  M  G  C  C  F
tctagagcatatcccactccactaaggtccaagaagacgatgttggtccaaaagaacgtc
 S  R  A  Y  P  T  P  L  R  S  K  K  T  M  L  V  Q  K  N  V
acctcagagtccacttgctgtgtagctaaatcatataacagggtcacagtaatgggggt
 T  S  E  S  T  C  C  V  A  K  S  Y  N  R  V  T  V  M  G  G
ttcaaagtggagaaccacacggcgtgccactgcagtacttgttattatcacaaatctggc
 F  K  V  E  N  H  T  A  C  H  C  S  T  C  Y  Y  H  K  S  G
ggcggaagcggaggcggatctggggaggatctggcggcggaaacttcactataaaatca
 G  G  S  G  G  G  S  G  G  G  S  G  G  N  F  T  I  K  S
ttgtccagacctggacagccctggtgtgaagcgcaggtcttcttgaataaaaatctt
 L  S  R  P  G  Q  P  W  C  E  A  Q  V  F  L  N  K  N  L
ttccttcagtacaacagtgacaacaacatggtcaaacctctgggcctcctggggaagaag
 F  L  Q  Y  N  S  D  N  N  M  V  K  P  L  G  L  L  G  K  K
gtatatgccaccagcacttggggagaattgacccaaacgctgggagaagtggggcgagac
 V  Y  A  T  S  T  W  G  E  L  T  Q  T  L  G  E  V  G  R  D
ctcaggatgctcctttgtgacatcaaaccccagataaagaccagtgatccttccactctg
 L  R  M  L  L  C  D  I  K  P  Q  I  K  T  S  D  P  S  T  L
caagtcgagatgttttgtcaacgtgaagcagaacggtgcactggtgcatcctggcagttc
 Q  V  E  M  F  C  Q  R  E  A  E  R  C  T  G  A  S  W  Q  F
gccaccaatggagagaaatccctcctctttgacgcaatgaacatgacctggacagtaatt
 A  T  N  G  E  K  S  L  L  F  D  A  M  N  M  T  W  T  V  I
aatcatgaagccagtaagatcaaggagacatggaagaaagacagagggctggaaaagtat
 N  H  E  A  S  K  I  K  E  T  W  K  K  D  R  G  L  E  K  Y
ttcaggaagctctcaaagggagactgcgatcactggctcagggaattcttagggcactgg
 F  R  K  L  S  K  G  D  C  D  H  W  L  R  E  F  L  G  H  W
gaggcaatgccagaaccgacagtgtcaccagtaaatgcttcagatatccactggtcttct
 E  A  M  P  E  P  T  V  S  P  V  N  A  S  D  I  H  W  S  S
tctagtctaccaTAG
 S  S  L  P Stop
```

METHODS AND COMPOSITIONS FOR TREATING CANCER

CROSS-REFERENCE TO RELATED APPLICATIONS

This application is a national stage of International Patent Application No. PCT/US15/53128, filed Sep. 30, 2015, which claims the benefit of the priority of U.S. Provisional Patent Application Nos. 62/202,824, filed Aug. 8, 2015, and 62/059,068, filed Oct. 2, 2014, which applications are incorporated herein by reference.

INCORPORATION BY REFERENCE OF MATERIAL SUBMITTED IN ELECTRONIC FORM

Applicant hereby incorporates by reference the Sequence Listing material filed in electronic form herewith. This file is labeled "WST150PCT_ST25.txt", was created on Sep. 28, 2015, and is 23 KB.

BACKGROUND OF THE INVENTION

Despite the advances in surgical approach and chemotherapy, the 5 year survival of ovarian cancer has barely changed in the last 40 years Immune pressure against ovarian cancer progression is elicited by tumor infiltrating T cells. Despite the devastating course of ovarian cancer, T cells can spontaneously exert clinically relevant pressure against malignant progression, to the point that the pattern and the intensity of T cell infiltration can predict the patient's outcome. Ovarian cancers are therefore immunogenic and optimal targets for the design of novel immunotherapies.

Over the last years, immunotherapy has emerged as a promising tool in the treatment of cancer. For example, Chimeric Antigen Receptor (CAR) therapy has shown excellent results in the treatment of chemotherapy resistant hematologic malignancies. However, the paucity of specific antigens expressed on the surface of tumor cells that are not shared with healthy tissues, has so far prevented the success of this technology against most solid tumors, including ovarian cancer. There is considerable difficulty in finding specific antigens in tumor cells which are not present in normal tissues and elicit intolerable side effects. Additionally, the immunosuppressive effect of the tumor microenvironment of solid tumors heavily impairs antitumor T cell responses

SUMMARY OF THE INVENTION

Compositions and methods are described herein that provide effective and useful tools and methods for the treatment of cancer, including solid tumors that are characterized by the cellular expression of the endocrine receptor, Follicle Stimulating Hormone (FSHR).

In one aspect, a nucleic acid construct comprises a nucleic acid sequence that encodes a chimeric protein comprising a ligand that comprises a follicle stimulating hormone (FSH) sequence, which ligand binds to human FSHR, linked to sequences providing T cell activating functions. In one aspect, the sequences providing T cell activating functions are (a) a nucleic acid sequence that encodes an extracellular hinge domain, a spacer element, a transmembrane domain, a co-stimulatory signaling region, and a signaling endodomain; or (b) a nucleic acid sequence that encodes an optional spacer and a ligand that binds to NKG2D. In one embodiment, the ligand is naturally occurring FSH, a single subunit of FSH, FSHβ, an FSH or FSHβ fragment, or a modified version of any of the foregoing sequences.

In another aspect, a chimeric protein comprising a ligand that comprises an FSH sequence, which ligand binds to human FSHR, linked to either (a) an extracellular hinge domain, a transmembrane domain, a co-stimulatory signaling region, and a signaling endodomain; or (b) an optional spacer, and a ligand that binds to NKG2D. In one embodiment, the ligand is naturally occurring FSH, a single subunit of FSH, FSHβ, an FSH or FSHβ fragment, or a modified version of any of the foregoing sequences.

In another aspect, a modified human T cell comprises a nucleic acid sequence that encodes a chimeric protein comprising a ligand that comprises an FSH sequence, which ligand binds to human FSHR, linked to an extracellular hinge domain, a transmembrane domain, a co-stimulatory signaling region, and a signaling endodomain in a pharmaceutically acceptable carrier. In one embodiment, the modified T cell is an autologous T cell isolated from the patient to whom the T cell will be readministered once the T cell is modified to contain a nucleic acid construct as described herein. In another embodiment, the modified T cell is a universal allogeneic platform, i.e., a heterologous T cell, for administration to any number or patients once the T cell is modified as described herein.

In one embodiment, the ligand is naturally occurring FSH, a single subunit of FSH, FSHβ, an FSH or FSHβ fragment, or a modified version of any of the foregoing sequences. In still another aspect, a method of treating a cancer in a human subject comprises administering to the subject in need thereof, a composition as described herein, including e.g., a nucleic acid sequence, chimeric protein, or modified T cell. In one embodiment, the method comprises administering to a subject in need thereof a modified human T cell that comprises a nucleic acid sequence that encodes a chimeric protein comprising a ligand that comprises an FSH sequence, which ligand binds to human FSHR, an extracellular hinge domain, a transmembrane domain, a co-stimulatory signaling region, and a signaling endodomain.

In still another aspect, a method of treating a cancer in a human subject comprises administering to a subject, a composition comprising a nucleic acid sequence that encodes a chimeric protein comprising a ligand that comprises an FSH sequence, which ligand binds to human FSHR, linked to either (a) a nucleic acid sequence that encodes an extracellular hinge domain, a spacer element, a transmembrane domain, a co-stimulatory signaling region, and a signaling endodomain; or (b) a nucleic acid sequence that encodes an optional spacer and a ligand that binds to NKG2D. In one embodiment, the ligand is naturally occurring FSH, a single subunit of FSH, FSHβ, an FSH or FSHβ fragment, or a modified version of any of the foregoing sequences.

In still another aspect, a method of treating a cancer in a human subject comprises administering to a subject, a composition comprising a chimeric protein comprising a ligand that comprises an FSH sequence, which ligand binds to human FSHR, linked to either (a) a nucleic acid sequence that encodes an extracellular hinge domain, a spacer element, a transmembrane domain, a co-stimulatory signaling region, and a signaling endodomain; or (b) a nucleic acid sequence that encodes an optional spacer and a ligand that binds to a tumor-associated NKG2D receptor.

In another aspect, a method of treating ovarian cancer comprises administering to a subject in need thereof, a modified human T cell comprises a nucleic acid sequence that encodes a chimeric protein comprising a ligand that comprises an FSH sequence, which ligand binds to human FSHR, linked to an extracellular hinge domain, a transmembrane domain, a co-stimulatory signaling region, and a signaling endodomain in a pharmaceutically acceptable carrier. In one embodiment, the ligand is naturally occurring FSH, a single subunit of FSH, FSHβ, an FSH or FSHβ fragment, or a modified version of any of the foregoing sequences. In another embodiment, the female subject has been surgically treated for removal of the ovaries prior to the administering step.

Other aspects and advantages of these compositions and methods are described further in the following detailed description of the preferred embodiments thereof.

BRIEF DESCRIPTION OF THE DRAWINGS

FIGS. 4A-4D show that there is an increased number of transferred T cells in the spleen of mice injected with the FSH chimeric protein—carrying T cells compared to those of mice injected with the mock protein-carrying T cells. Also a higher CD4/CD8 ratio is detected in the spleen cells into which the chimeric protein—carrying T cells were transferred. This ratio is found to be a good marker of response against cancer in this cell model of ovarian cancer.

FIG. 5 is a nucleic acid sequence SEQ ID NO: 1 and an amino acid sequence SEQ ID NO: 2 for a construct comprising the following fused components of Table 1:

TABLE 1

| Component | Nucleic Acids of SEQ ID NO: 1 | Amino Acids of SEQ ID NO: 2 |
|---|---|---|
| Human FSH Beta Signal | 1-54 | 1-18 |
| Human FSH beta | 55-387 | 19-129 |
| Spacer | 388-432 | 130-144 |
| Human FSH alpha | 433-801 | 145-267 |
| Hinge from Human CD8 | 802-936 | 268-312 |
| Transmembrane domain from Human CD8 | 937-1008 | 313-336 |
| Human intracellular region from 4-1BB | 1009-1134 | 337-378 |
| Human CD3 Z Domain | 1135-1473 | 379-490 |

Figure 6A:
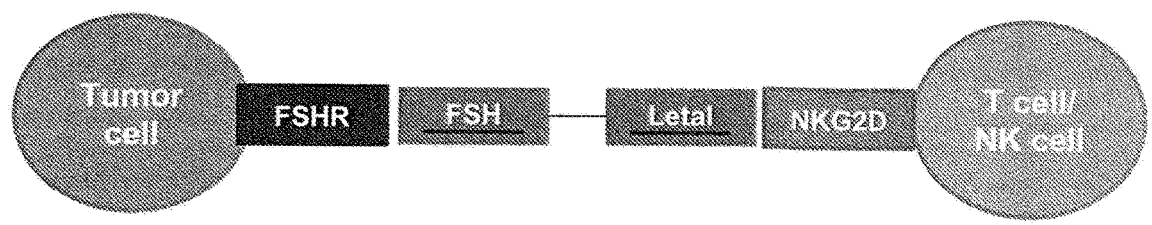

FIG. 6A is a schematic of a chimeric FSH-Letal construct, which demonstrates how it binds to a tumor cell and a NK cell or a T cell (e.g., a CD8 T cell, a gamma T cell or an NK T cell).

FIG. 6B is a nucleic acid sequence SEQ ID NO: 3 and an amino acid sequence SEQ ID NO: 4 for a construct comprising the following fused components of Table 2:

TABLE 2

| Component | Nucleic Acids of SEQ ID NO: 3 | Amino Acids of SEQ ID NO: 4 |
|---|---|---|
| Human FSH Beta Signal | 1-3 | 1 |
| Human FSH beta | 4-336 | 2-112 |
| Spacer | 337-381 | 113-127 |
| Human FSH alpha | 382-750 | 128-250 |
| Spacer | 751-795 | 251-265 |
| Human extracellular NKG2D ligand (Letal) | 796-1365 | 266-454 |

FIG. 6C is a nucleic acid sequence SEQ ID NO: 5 and an amino acid sequence SEQ ID NO: 6 for a construct comprising the following fused components of Table 3. Construct has a MW of 45.87 kD, and employs noncutting enzyme sites AscI, BamHI, BcgI, BclI, ClaI, HindIII, KpnI, MfeI, MluI, NcoI, NdeI, NotI, Pad, PmeI, PsiI, PvuI, SacII, SalI, SfiI, SgfI, SpeI, SphI, XbaI, and XhoI.

TABLE 3

| Component | Nucleic Acids of SEQ ID NO: 5 | Amino Acids of SEQ ID NO: 6 |
|---|---|---|
| Mouse FSH Beta Signal | 1-3 | 1 |
| Mouse FSH beta | 4-336 | 2-112 |
| Spacer | 337-381 | 113-127 |
| Mouse FSH alpha | 382-657 | 128-219 |
| Spacer | 658-708 | 220-236 |
| Extracellular domain of Mouse MULT1 | 709-1260 | 237-446 |

FIG. 6D is a nucleic acid sequence SEQ ID NO: 7 and an amino acid sequence SEQ ID NO: 8 for a construct comprising the following fused components of Table 4:

TABLE 4

| Component | Nucleic Acids of SEQ ID NO: 7 | Amino Acids of SEQ ID NO: 8 |
|---|---|---|
| Human FSH Beta Signal | 1-3 | 1 |
| Human FSH beta | 4-336 | 2-112 |
| Spacer | 337-381 | 113-127 |
| Human FSH alpha | 382-657 | 128-219 |
| Spacer | 658-702 | 220-234 |
| Human extracellular domain of Letal | 703-1272 | 235-423 |

Figure 7A:
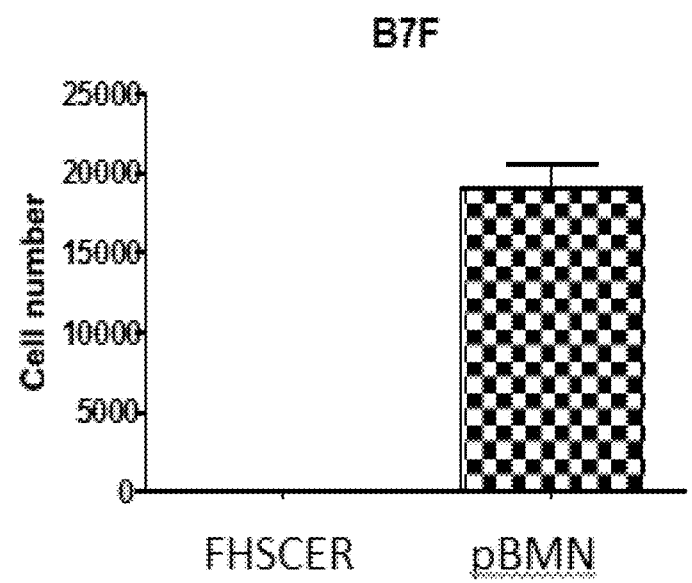

FIG. 7A is a bar graph showing that adherent FSHR-transduced ID8-Defb29/Vegf-a (B7F) cancer cells were incubated for 24 hours with FSH CER-expressing or mocked transduced T cells, pBMN (1:40 ratio). After removing non-adherent cells, trypan blue negative cells were counted in a hematocytometer. FSH-targeted CER T cells effectively eliminate FSHR+ tumor cells.

Figure 7B:
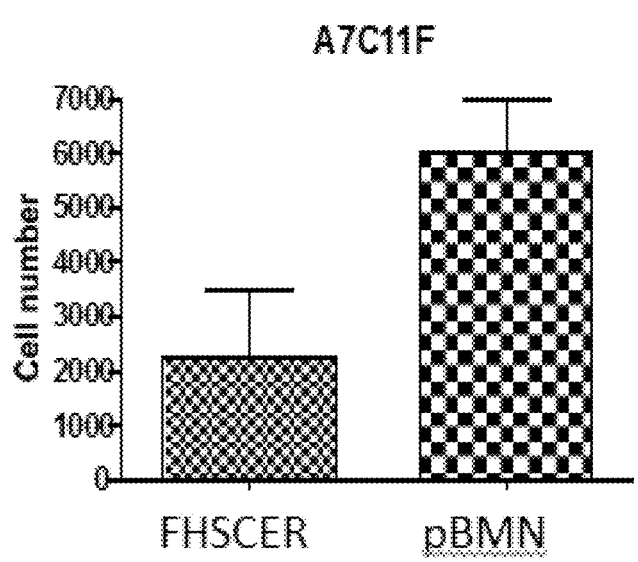

FIG. 7B is a bar graph showing that adherent FSHR-transduced A7C11F transduced with the FSH-targeted constructs described herein effectively eliminate FSHR+ tumor cells. Adherent FSHR-transduced A7C11F cancer cells were incubated for 24 hours with FSH CER-expressing or mocked transduced T cells (1:40 ratio). After removing non-adherent cells, trypan blue negative cells were counted in a hematocytometer. FSH-targeted CER T cells effectively eliminate FSHR+ tumor cells.

Figure 8:
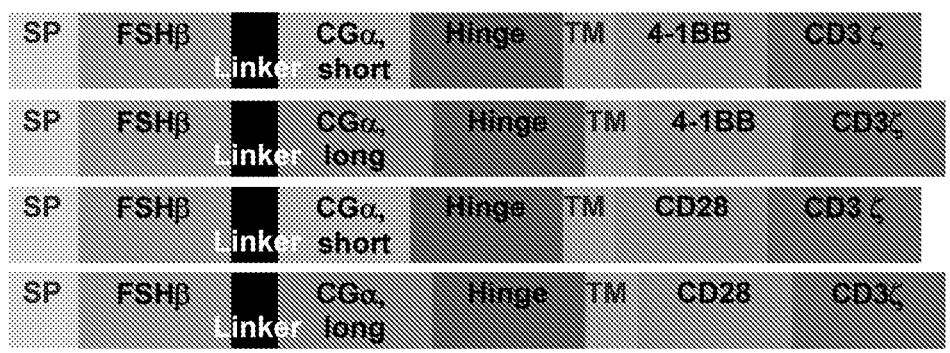

FIG. 8 is a schematic showing variants of the FSH Chimeric Endocrine Receptor (CER)-T constructs described herein.

Figure 9:
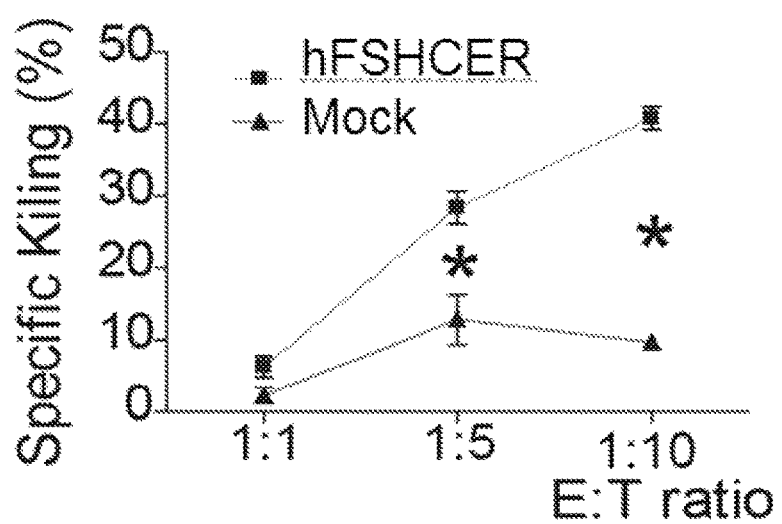

FIG. 9 is a graph showing the human FSHCER T cells kill ovarian tumor cells in a dose-dependent manner. HLA-A2+ human T cells were expanded with ConA, spininfected with hFSHCER in pBMN with retronectin or mock-transduced at 20 and 44 hours, and kept at 0.5-1 million cells/mL with 1 ug/mL of IL-7 and 20 U/mL of IL-2. At day 7, CER and control T cells were sorted on GFP expression and rested for 18 hours, before being plated with plated with HLA-A2+ human OVCAR-3 ovarian cancer cells (10000 per well; spontaneously FSHR+) on the indicated effector (E) to target (T) ratios. Six hours after setting the coculture cells were stained with Annexin V and 7AAD and cytotoxicity was analyzed by flow cytometry. The percentage of specific lysis was calculated as (experimental dead−spontaneous dead)/(maximum dead−spontaneous dead)×100%.

Figure 10:
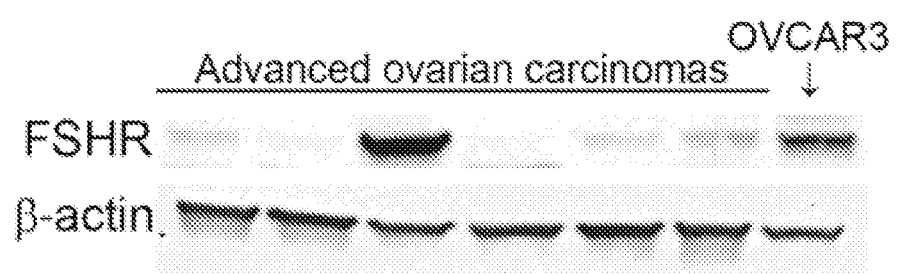

FIG. 10 is a Western gel showing that advanced human ovarian carcinoma specimens express variable levels of FSHR. FSHR protein expression was analyzed by Western Blot (Santa Cruz#H-190) in 6 unselected human advanced ovarian carcinoma specimens, and compared to that in FSH-targeted CER T cell-sensitive OVCAR3 cells. β-actin Ab, Sigma#A5441

Figure 11:
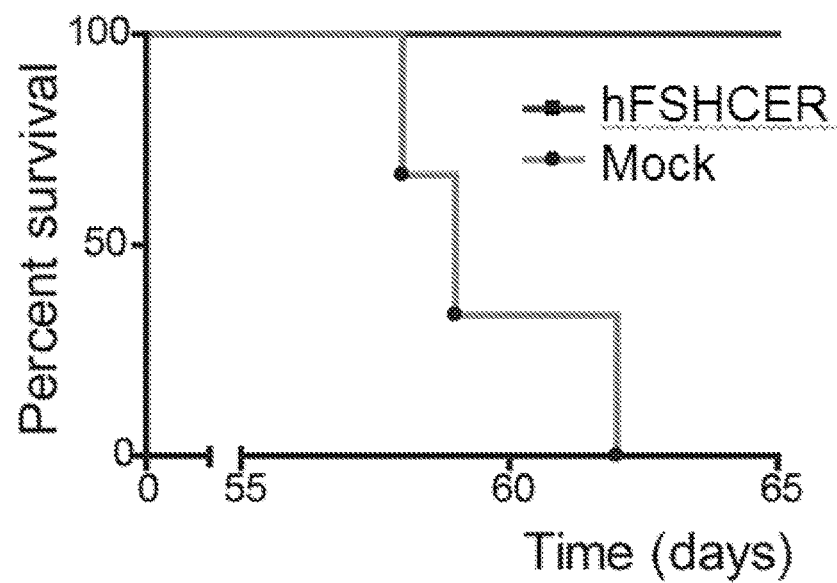

FIG. 11 is a graph showing that FSHCER T cells abrogate the progression of fshr-expressing orthotopic ovarian tumors. T cells carrying FSHR-targeting cars (FSH-CER) or identically expanded mock-transduced t cells (PBMN) were intraperitoneally administered at days 7 and 14 after intraperitoneal challenge with ID8-defb29/vegf-a tumor cells transduced with FSHR (n=5 mice/group). Malignant progression was compared.

Figure 12:
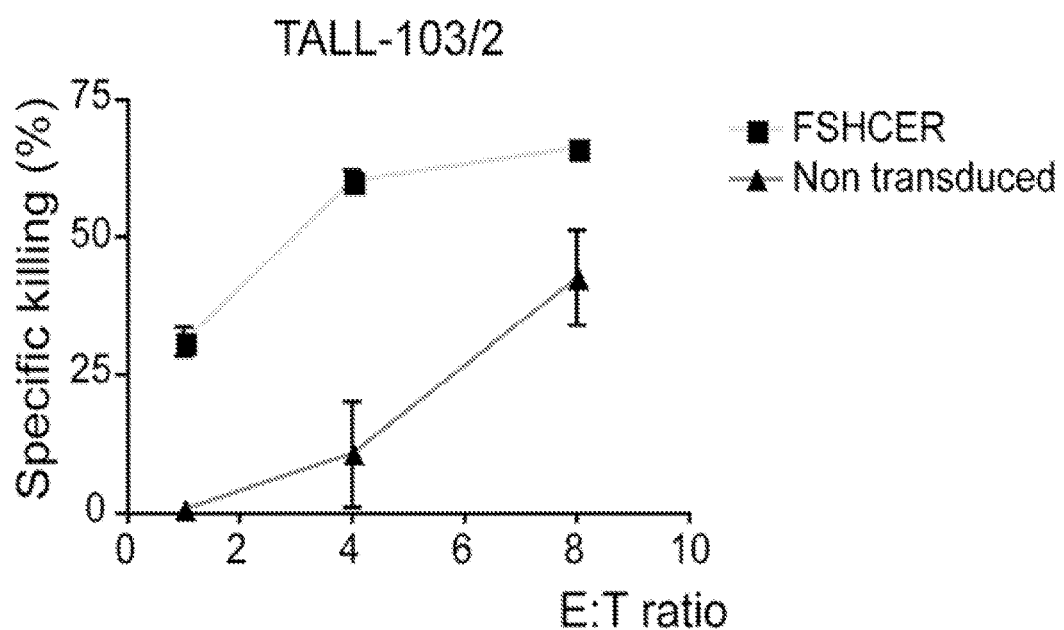

FIG. 12 is a graph showing that a modified allogeneic or heterologous human FSH CER T cell generated by using TALL-103/2 cells, kill ovarian tumor cells in a dose-dependent manner. TALL-103/2 cells were transduced with hFSH-CER in pBMN and maintained in culture with 20 U/mL of IL-2. FSH CER-transduced (■) or mock-transduced (▲) TALL-103/2 cells were deprived from IL-2 24 h before being incubated with luciferase-transduced FSHR+ human OVCAR-3 ovarian cancer cells (10000 per well) at the indicated effector (E) to target (T) ratios. Four hours after setting the co-culture cells were lysed and luciferase signal quantified. The percentage of specific lysis was calculated as (experimental dead−spontaneous dead)/(maximum dead−spontaneous dead)×100%.

DETAILED DESCRIPTION OF THE INVENTION

Compositions and methods are provided herein that elicit protective anti-tumor immunity against, and prevent recurrence of, e.g., ovarian cancer or other cancers characterized by tumor cells bearing the FSH receptor (FSHR), e.g., prostate cancer cells[52] and metastatic tumor lesions[51]. By targeting hormone receptors by taking advantage of endogenous ligands as targeting motifs, challenges that have prevented the success of certain immunotherapy technologies against epithelial tumors are overcome.

Technical and scientific terms used herein have the same meaning as commonly understood by one of ordinary skill in the art to which this invention belongs and by reference to published texts, which provide one skilled in the art with a general guide to many of the terms used in the present application. The following definitions are provided for clarity only and are not intended to limit the claimed invention.

Follicle stimulating hormone (FSH) is a central hormone of mammalian reproduction produced primarily in the anterior pituitary gland. This hormone exerts its normal biological role by binding to the plasma membrane follicle-stimulating hormone receptor (FSHR) and stimulating follicular maturation and estrogen production in females. In males, the interaction of FSH and FSHR stimulates Sertoli cell proliferation and maintenance of normal spermatogenesis. The naturally occurring FSH hormone is a heterodimer formed of two subunits, an alpha and a beta subunit. The alpha subunit is also referred to as CGα, and is common to luteinizing hormone (LH) and thyroid stimulating hormone (TSH). The nucleic acid and amino acid sequences of the alpha and beta subunits of FSH for humans and other mammalian species are publically known and accessible.

FSHR is a hormone receptor that is selectively expressed in women in the ovarian granulosa cells and at low levels in the ovarian endothelium. Most importantly, this surface receptor is expressed in 50-70% of ovarian carcinomas but not in the brain, as negative feedback depends on sensing estrogen. Given that oophorectomy is a standard procedure in the treatment of ovarian cancer, targeting the FSHR should not cause damage to healthy tissues.

As used herein, the phrase "a ligand that comprises an FSH sequence, which ligand binds FSHR" includes the naturally occurring full-length FSH sequence of a suitable mammal. The ligand comprises a sufficient FSH sequence to permit binding between the ligand and the FSHR via the naturally affinity between the hormone sequence and the receptor. The ligand is not an antibody or antibody fragment and does not bind to the receptor in that manner. If the ligand is naturally occurring, e.g., a full-length FSHβ-FSHα sequence or naturally occurring fragment thereof, the ligand does not induce an immunogenic reaction in the subject to which it is administered. If the ligand comprises a modified full-length or fragment of the naturally occurring FSH sequence, in certain embodiments the modifications are not sufficient to induce any strong immunogenic reaction within the subject to which the ligand is administered.

In one embodiment, a ligand that comprises an FSH sequence is a naturally occurring full length human FSH, e.g., the FSHβ sequence linked to the FSHα sequence. In another embodiment, a ligand that comprises an FSH sequence is a modified FSHβ sequence linked to a naturally occurring FSHα sequence. In another embodiment, a ligand that comprises an FSH sequence is a modified FSHβ sequence linked to a modified FSHα/CGα sequence. In another embodiment, the ligand is a naturally occurring FSHβ sequence linked to a modified FSHα sequence. In another embodiment, where the subject mammal is a human and the target tumor is a human tumor, a suitable FSH sequence is human FSH or modified versions of the human sequence. Alternatively the ligand is a modified FSH, such as a naturally occurring or modified FSHβ sequence linked via an optional spacer to a naturally occurring or modified FSHα sequence. In another embodiment, the ligand is a single naturally occurring or modified FSHβ subunit alone. In another embodiment, the ligand is a naturally occurring FSHβ subunit linked via an optional spacer sequence to a modified second FSHβ sequence. In another embodiment, the ligand is a modified FSHβ subunit linked via an optional spacer sequence to a naturally occurring second FSHβ sequence.

In yet another embodiment, the ligand comprises a fragment of a naturally occurring or modified FSH sequence. In yet another embodiment, the ligand comprises a fragment of a naturally occurring or modified FSHβ sequence. In another embodiment, the ligand is a naturally occurring FSHβ subunit linked to a modified FSHα subunit or fragment thereof. In another embodiment, the ligand is a modified FSHβ subunit or fragment thereof linked to a naturally occurring or FSHα subunit. In another embodiment, the ligand comprises a fragment of a naturally occurring or modified FSHβ sequence linked together.

By "naturally occurring" is meant that the sequence is a native nucleic acid or amino acid sequence that occurs in the selected mammal, including any naturally occurring variants in various nucleic acid and/or amino acid positions in the sequences that occur among various members of the mammalian species.

By "modified" is meant that the reference sequence, e.g., FSH or a fragment thereof or FSHβ linked to FSHα nucleic acid or amino acid sequence, or either subunit sequence individually has been deliberately manipulated. Suitable modifications include the use of fragments of the sequences shorter than the naturally occurring full length hormone. Such modifications include changes in the nucleic acid sequences to include preferred codons, which may encode the same or a related amino acid than that occurring in the native amino acid sequence. Modifications also include changes in the nucleic acid or amino acid sequences to introduce conservative amino acid changes, e.g., a change from one charged or neutral amino acid for a differently charged amino acid. Such modifications may also include use of the FSHβ with or without FSHα sequence in a deliberately created fusion with other sequences with which FSHβ or FSHα do not naturally occur. Modifications also include linking the subunits using deliberately inserted spacer sequences or linking fragments of the subunits together or linking repetitive fragments or subunits together in fusions which are not naturally occurring.

As one example, a naturally occurring human FSHβ nucleic acid sequence inclusive of the signal sequence comprises or consists of nucleic acids 1-387 of SEQ ID NO: 1, and amino acid sequence is aa 1-129 of SEQ ID NO: 2. The FSHβ signal sequence itself comprises or consists of nucleic acids 1-54 of SEQ ID NO: 1, and amino acid sequence is aa 1-18 of SEQ ID NO: 2 The mature FSHβ comprises or consists of nucleic acids 55-387 of SEQ ID NO: 1, and amino acid sequence is aa 19-129 of SEQ ID NO: 2.

As another example for use in the methods and compositions herein, a mature human FSHβ nucleic acid sequence comprises or consists of nucleic acids 4-336 of SEQ ID NO: 3 or 7, and amino acid sequence is aa 2-112 of SEQ ID NO: 4 or 8. As another example for use in the methods and compositions herein, a useful fragment of a human FSHβ nucleic acid sequence comprises or consists of nucleic acids 55-99 of FSHβ SEQ ID NO: 1, nucleic acids 153-213 of FSHβ SEQ ID NO: 1, nucleic acids 207-249 of FSHβ SEQ ID NO: 1, or nucleic acids 295-339 of FSHβ SEQ ID NO: 1. As another example for use in the methods and compositions herein, a useful fragment of a human FSHβ amino acid sequence comprises or consists of amino acids 19-33 of FSHβ SEQ ID NO: 2, amino acids 51-71 of FSHβ SEQ ID NO: 2, amino acids 69-83 of FSHβ SEQ ID NO: 2, or amino acids 99-113 of FSHβ SEQ ID NO: 2.

In embodiments in which the ligand also comprises an FSHα sequence, the naturally occurring human FSHα nucleic acid sequence comprises or consists of nucleic acids 433-801 of SEQ ID NO: 1, and amino acid sequence is aa 145-267 of SEQ ID NO: 2. In another embodiment for use in the methods and compositions herein, a human FSHα nucleic acid sequence comprises or consists of nucleic acids 382-750 of SEQ ID NO: 3, and amino acid sequence is aa 128-250 of SEQ ID NO: 4. In another embodiment for use in the methods and compositions herein, a fragment of a human FSHα nucleic acid sequence comprises or consists of nucleic acids 382-657 of SEQ ID NO: 7, and amino acid sequence is aa 128-219 of SEQ ID NO: 8.

It should be understood that amino acid modifications or nucleic acid modifications as described above applied to these fragments are also useful ligands in this method. The ligand does not bind to FSHR in an antibody or antibody fragment—antigen complex. As described above, the ligands described herein bind using the naturally affinity between the natural hormone (or a modified version of a natural hormone) and its receptor. Because the ligand is a natural hormone or a modified version thereof, it is designed to avoid inducing an antigenic response in the subject.

The terms "linker" and "spacer" are used interchangeably and refer to a nucleic acid sequence that encodes a peptide of sufficient length to separate two components and/or refers to the peptide itself. The composition and length of a linker may be selected depending upon the use to which the linker is put. In one embodiment, an amino acid linker used to separate the FSHα and FSHβ (either naturally occurring sequences or modified sequences or fragments) is between 2 to 70 amino acids in length, including any number within that range. For example, in one embodiment the linker is 10 amino acids in length. In another embodiment, the linker is 15 amino acids in length. In still other embodiment, the linker is 25, 35, 50 or 60 amino acids in length. See, for example, the spacers/linkers identified in the sequences described in Tables 1-4 above.

Correspondingly, the nucleic acid sequences encoding the linker or spacer are comprised of from 6 to 210 nucleotides in length, including all values in that range. In certain embodiment, the linker comprises multiple glycine residues or nucleic acids encoding them. In certain embodiments, the amino acid linker comprises multiple serine residues or nucleic acids encoding them. In other embodiment, the linker comprises multiple thymine residues or nucleic acids encoding them. In still other embodiment, linkers and spacers comprise any combination of the serine, thymine and glycine residues. Still other linkers can be readily designed for use.

As used herein, a "vector" comprises any genetic element including, without limitation, naked DNA, a phage, transposon, cosmid, episome, plasmid, bacteria, or a virus, which expresses, or causes to be expressed, a desired nucleic acid construct.

As used herein, the term "subject" or "patient" refers to a male or female mammal, preferably a human. However, the mammalian subject can also be a veterinary or farm animal, a domestic animal or pet, and animals normally used for clinical research. In one embodiment, the subject of these methods and compositions is a human.

The term "cancer" as used herein means any disease, condition, trait, genotype or phenotype characterized by unregulated cell growth or replication as is known in the art. A "cancer cell" is cell that divides and reproduces abnormally with uncontrolled growth. This cell can break away from the site of its origin (e.g., a tumor) and travel to other parts of the body and set up another site (e.g., another tumor), in a process referred to as metastasis. A "tumor" is an abnormal mass of tissue that results from excessive cell division that is uncontrolled and progressive, and is also referred to as a neoplasm. Tumors can be either benign (not cancerous) or malignant. The compositions and methods described herein are useful for treatment of cancer and tumor cells, i.e., both malignant and benign tumors, so long as the cells to be treated express FSHR. Thus, in various embodiments of the methods and compositions described herein, the cancer can include, without limitation, breast cancer, lung cancer, prostate cancer, colorectal cancer, esophageal cancer, stomach cancer, bladder cancer, pancreatic cancer, kidney cancer, cervical cancer, liver cancer, ovarian cancer, and testicular cancer.

As used herein the term "pharmaceutically acceptable carrier" or "diluent" is intended to include any and all solvents, dispersion media, coatings, antibacterial and antifungal agents, isotonic and absorption delaying agents, adjuvants and the like, compatible with administration to humans. In one embodiment, the diluent is saline or buffered saline. The term "a" or "an", refers to one or more, for example, "an anti-tumor T cell" is understood to represent one or more anti-tumor T cells. As such, the terms "a" (or "an"), "one or more," and "at least one" is used interchangeably herein. The term "about" is used herein to modify a reference value and to include all values ±0.01% of that value up to values of ±10% of the reference value, and all numbers within and including these endpoints, e.g., ±0.5%, ±1%, ±5%, etc. Various embodiments in the specification are presented using "comprising" language, which is inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention.

In one embodiment, this invention provides a nucleic acid sequence that encodes a chimeric protein comprising a ligand comprising an FSH sequence that binds to human FSHR, linked to nucleic acid sequences that encode T cell activating functions. As described above in more detail, in certain embodiments, the ligand is a naturally occurring FSH with both subunits, a single subunit of FSH, an FSHβ subunit only, an FSHα/CGα or FSHβ fragment, or a modified version of the foregoing sequences.

In one embodiment, the T cell activating functions can be provided by linking the above noted ligand with nucleic acid sequences encoding components useful in the design of known Chimeric Antigen Receptors (CAR). See, e.g., Sadelain, M et al, "The basic principles of chimeric antigen receptor (CAR) design" 2013 April, Cancer Discov. 3(4): 388-398; International Patent Application Publication WO2013/044225, US patent application publication No. US 2013/0287748, and other publications directed to the use of such chimeric proteins. These publications are incorporated by reference to provide information concerning various components useful in the design of some of the constructs described herein. Such CAR T cells are genetically modified lymphocytes expressing a ligand that allows them to recognize an antigen of choice. Upon antigen recognition, these modified T cells are activated via signaling domains converting these T cells into potent cell killers. An advantage over endogenous T cells is that they are not MHC restricted, which allows these T cells to overcome an immune surveillance evasion tactic used in many tumor cells by reducing MHC expression[19].

For example, such T cell activating functions can be provided by linking the ligand via optional spacers to transmembrane domains, co-stimulatory signaling regions, and/or signaling endodomains.

Thus, one embodiment of a nucleic acid sequence useful in the methods described herein is exemplified in FIG. 5 SEQ ID NO: 1 and Table 1 herein. The nucleic acid sequence or CER construct comprises a ligand formed of a naturally occurring human FSHβ sequence formed of the 18 amino acid human FSHβ signal sequence and the 120 amino acid mature FSHβ, linked to a 15 amino acid spacer, and to the naturally occurring 123 amino acid FSHα sequence. The CER construct also includes other components, i.e., an extracellular hinge domain, a transmembrane domain, a human intracellular region and a signaling endodomain. In the case of the construct of FIG. 5, e.g. the hinge region and transmembrane domains are from human CD8α, the human intracellular region is from 4-1BB, and the signaling domain is the human CD3ζ domain.

Other embodiments useful as such a nucleic acid construct can include that construct with a different ligand, such as one of the ligands described above. In one embodiment, the FSHα sequence in the same construct described in FIG. 5 may be a shortened sequence having the nucleic acid sequence of nts 382-657 of SEQ ID NO: 7, and amino acid sequence of aa 128-219 of SEQ ID NO: 8. Still another embodiment of the ligand used in the construct of FIG. 5 may comprise the FSHβ sequence without signal sequence amino acids 2-18 of SEQ ID NO: 2. Embodiments similar to that of the nucleic acid construct of FIG. 5 may be readily designed by substituting the ligand portions of Table 1 with any of the ligands, modified, naturally occurring or fragments discussed above.

Other embodiments of a nucleic acid construct similar to that of FIG. 5 may employ different components, such as those detailed in Sadelain et al, cited above, or the patent publications, incorporated by reference herein. For example, where a hinge domain is employed, other naturally occurring or synthetic hinge domains, including an immunoglobulin hinge region, such as that from IgG1, the $CH_2CH_3$ region of immunogiobulin, fragments of CD3, etc. Other embodiments of a nucleic acid construct similar to that of FIG. 5 may employ a different naturally occurring or synthetic transmembrane domain obtained from a T cell receptor.

Various transmembrane proteins contain domains useful in the constructs described herein. For example, transmembrane domains obtained from T-cell receptors, CD28, CD3 epsilon, CD45, CD4, CD8, CD9, CD16, CD22, CD33, CD37, CD64, CD80, CD86, CD134, CD137, or CD154 have been noted to be useful.

Other embodiments of a nucleic acid construct similar to that of FIG. 5 may employ a different naturally occurring or synthetic intracellular region, including, among others known in the art, a costimulatory signaling region. The costimulatory signaling region may be the intracellular domain of a cell surface molecule (e.g., a costimulatory molecule) such as CD27, CD28, 4-1BB (CD137), OX40, CD30, CD40, PD-1, ICOS, lymphocyte function-associated antigen-1 (LFA-1), CD2, CD7, LIGHT, NKG2C, B7-H3. See, e.g., others listed in the publications cited above.

Other embodiments of a nucleic acid construct similar to that of FIG. 5 may employ a different naturally occurring or synthetic cytoplasmic signaling domain including, among others known in the art, those derived from CD3ζ, TCRζ, FcRγ, FcRβ, CD3γ, CD3δ, CD3ε, CD5, CD22, 25 CD79a, CD79b, and CD66d, among others.

Given the teachings provided herein and using the information known to the art, any number of variations of the nucleic acid constructs, such as FIG. 5 may be designed for use in the methods described herein.

Thus, another component described herein is a chimeric protein comprising a ligand that comprises an FSHβ sequence, or a modification or fragment of said FSH sequence, which ligand binds to human FSHR, linked to peptides or proteins that have T cell activating functions. Such a chimeric protein comprises a ligand as described above that binds to human FSHR linked to an extracellular hinge domain, a transmembrane domain, a co-stimulatory signaling region, and a signaling endodomain. Exemplary chimeric proteins are encoded by the nucleic acid sequences described above. One embodiment of such a chimeric protein is that of FIG. 5 SEQ ID NO: 2. Others are readily designed employing the various ligands identified herein, e.g., one or more of the FSHβ fragment identified in detail above, or the other FSHR binding ligands identified herein in place of the ligand specific exemplified in SEQ ID NO: 2.

In another embodiment, a useful CER construct is a nucleic acid sequence that encodes ligand that comprises an FSHβ sequence, or a modification or fragment of said FSH sequence, which ligand binds to human FSHR, as described above, linked to a nucleic acid sequence that encodes a ligand that binds to a tumor-associated NKG2D receptor. See, e.g., FIG. 6A. One such NKG2D ligand is termed Letal or ULBP4. Letal is encoded by nucleic acid sequence nts 796-1365 of SEQ ID NO: 3 and has the amino acid sequence of aa 266-454 of SEQ ID NO: 4. See, e.g., Conejo-Garcia, J et al, "Letal, A Tumor-Associated NKG2D Immunoreceptor Ligand, Induces Activation and Expansion of Effector Immune Cells" July 2003, Canc. Biol. & Ther., 2(4): 446-451; and US patent application publication No. 20060247420, incorporated by reference herein. Other NKG2D ligands or amino acid modifications, modifications on the nucleic acid level or functional fragments of the Letal sequence may be substituted in this description for the exemplified Letal sequences.

Additionally, these FSHR binding ligands and NKG2D ligand are optionally linked by a suitable spacer or linker as described above.

Specific examples of such a nucleic construct are provided in FIG. 6A, FIG. 6B, Table 2, SEQ ID NO: 3, FIG. 6D, Table 4, SEQ ID NO: 7, and FIG. 8. In the embodiment of FIG. 7B, the FSHR binding ligand is formed of a naturally occurring human FSHβ sequence formed of a single amino acid methionine from the signal sequence, followed by the 120 amino acid mature FSHβ, linked to a 15 amino acid spacer, in turn linked to the naturally occurring 123 amino acid FSHα sequence. This ligand is in turn linked to Letal via another 15 amino acid spacer. In the embodiment of FIG. 6D, the FSHR binding ligand is formed of a naturally occurring human FSHβ sequence formed of a single amino acid methionine from the signal sequence, followed by the 120 amino acid mature FSHβ, linked to a 15 amino acid spacer, in turn linked to the modified FSHα sequence, i.e., a fragment of amino acids 128-219 of SEQ ID NO: 8, encoded by nucleotides 382-657 of SEQ ID NO: 7. This ligand is in turn linked to Letal via another 15 amino acid spacer.

Other embodiments useful as such a nucleic acid construct can include the constructs of FIGS. 6B and 6D with a different ligand-encoding sequence, such as a sequence encoding one of the ligands described above. In one embodiment, the FSHα sequence in the same construct described in FIG. 6B may be a single or multiple copies of full length FSHβ with or without a signal sequence. As another example the construct of FIG. 6B or 6D may contain a ligand formed by a fragment of a human FSHβ encoded by nucleic acid sequence comprising or consisting of nucleic acids 55-99 of FSHβ SEQ ID NO: 1, nucleic acids 153-213 of FSHβ SEQ ID NO: 1, nucleic acids 207-249 of FSHβ SEQ ID NO: 1, or nucleic acids 295-339 of FSHβ SEQ ID NO: 1. The ligand may be formed by these fragments alone, in combination or substituted for the full-length FSHβ and thus fused via a linker with the FSHα sequence of FIG. 6B or 6D. Embodiments similar to that of the nucleic acid construct of FIG. 6B or 6D may be readily designed by substituting the ligand portions of Table 2 or 4 with any of the ligands, modified, naturally occurring or fragments discussed above.

As another aspect, therefore, is a chimeric or bi-specific protein encoded by the nucleic acid sequences described above and comprising a ligand comprising a FSHβ sequence, or a modification or fragment of said FSH sequence as described herein that binds to human FSHR, linked to a ligand that binds to NKG2D. These proteins are primarily useful in the form of a protein, and function in vivo to bring together endogenous lymphocytes and FSHR+ tumor cells.

In still other aspects, recombinant vectors carrying the above-described nucleic acid constructs are provided. The nucleic acid constructs may be carried, and chimeric proteins may be expressed in, plasmid based systems, of which many are commercially available or in replicating or non-replicating recombinant viral vectors. The nucleic acid sequences discussed herein may be expressed and produced using such vectors in vitro in desired host cells or in vivo. Thus, in one embodiment, the vector is a non-pathogenic virus. In another embodiment, the vector is a non-replicating virus. In one embodiment, a desirable viral vector may be a retroviral vector, such as a lentiviral vector. In another embodiment, a desirable vector is an adenoviral vector. In still another embodiment, a suitable vector is an adeno-associated viral vector. Adeno, adeno-associated and lentiviruses are generally preferred because they infect actively dividing as well as resting and differentiated cells such as the stem cells, macrophages and neurons. A variety of adenovirus, lentivirus and AAV strains are available from the American Type Culture Collection, Manassas, Va., or available by request from a variety of commercial and institutional sources. Further, the sequences of many such strains are available from a variety of databases including, e.g., PubMed and GenBank.

In one embodiment, a lentiviral vector is used. Among useful vectors are the equine infectious anemia virus and feline as well as bovine immunodeficiency virus, and HIV-based vectors. A variety of useful lentivirus vectors, as well as the methods and manipulations for generating such vectors for use in transducing cells and expressing heterologous genes, e.g., N Manjunath et al, 2009 Adv Drug Deliv Rev., 61(9): 732-745; Porter et al., N Engl J Med. 2011 Aug. 25; 365(8):725-33), among others.

In another embodiment, the vector used herein is an adenovirus vector. Such vectors can be constructed using adenovirus DNA of one or more of any of the known adenovirus serotypes. See, e.g., T. Shenk et al., *Adenoviridae: The Viruses and their Replication*", Ch. 67, in FIELD'S VIROLOGY, 6$^{th}$ Ed., edited by B.N Fields et al, (Lippincott Raven Publishers, Philadelphia, 1996), p. 111-2112; U.S. Pat. No. 6,083,716, which describes the genome of two chimpanzee adenoviruses; U.S. Pat. No. 7,247,472; WO 2005/1071093, etc. One of skill in the art can readily construct a suitable adenovirus vector to carry and express a nucleotide construct as described herein. In another embodiment, the vector used herein is an adeno-associated virus (AAV) vector. Such vectors can be constructed using AAV DNA of one or more of the known AAV serotypes. See, e.g., U.S. Pat. Nos. 7,803,611; 7,696,179, among others.

In yet another embodiment, the vector used herein is a bacterial vector. In one embodiment, the bacterial vector is *Listeria monocytogenes*. See, e.g., Lauer et al, Infect. Immunity, 76(8):3742-53 (August 2008). Thus, in one embodiment, the bacterial vector is live-attenuated or photochemically inactivated. The chimeric protein can be expressed recombinantly by the bacteria, e.g., via a plasmid introduced into the bacteria, or integrated into the bacterial genome, i.e., via homologous recombination.

These vectors also include conventional control elements that permit transcription, translation and/or expression of the nucleic acid constructs in a cell transfected with the plasmid vector or infected with the viral vector. A great number of expression control sequences, including promoters which are native, constitutive, inducible and/or tissue-specific, are known in the art and may be utilized. In one embodiment, the promoter is selected based on the chosen vector. In another embodiment, when the vector is lentivirus, the promoter is U6, H1, CMV IE gene, EF-1α, ubiquitin C, or phosphoglycero-kinase (PGK) promoter. In another embodiment, when the vector is an AAV, the promoter is an RSV, U6, or CMV promoter. In another embodiment, when the vector is an adenovirus, the promoter is RSV, U6, CMV, or H1 promoters. In another embodiment, when the vector is *Listeria monocytogenes*, the promoter is a hly or actA promoter. Still other conventional expression control sequences include selectable markers or reporter genes, which may include sequences encoding geneticin, hygromicin, ampicillin or purimycin resistance, among others. Other components of the vector may include an origin of replication. Selection of these and other promoters and vector elements are conventional and many such sequences are available (see, e.g., the references cited herein).

These vectors are generated using the techniques and sequences provided herein, in conjunction with techniques known to those of skill in the art. Such techniques include conventional cloning techniques of cDNA such as those described in texts (Sambrook et al, Molecular Cloning: A Laboratory Manual, Cold Spring Harbor Press, Cold Spring Harbor, N.Y.), use of overlapping oligonucleotide sequences, polymerase chain reaction, and any suitable method which provides the desired nucleotide sequence.

Thus, in one embodiment, using the information taught herein and publically available and known vector construction components and techniques, one of skill in the art can construct a viral vector (or plasmid) that expresses the desired nucleic acid construct. The chimeric proteins encoded by these nucleic acid constructs may be expressed in vitro, or ex vivo in host cells or expressed in vivo by administration to a mammalian subject. Alternatively the chimeric proteins may be generated synthetically by known chemical synthesis methodologies. One of skill in the art can select the appropriate method to produce these chimeric proteins depending upon the components, the efficiency of the methodologies and the intended use, e.g., whether for administration as proteins, nucleic acids or in adoptive T cells, or otherwise to accomplish the desired therapeutic result.

In yet another aspect, a modified human T cell is provided that comprises a nucleic acid sequence that encodes a chimeric protein comprising a ligand that binds to human FSHR, linked to nucleic acid sequences that encode T cell activating functions. In one embodiment, these latter nucleic acid sequences encode an extracellular hinge domain, a transmembrane domain, a co-stimulatory signaling region, and a signaling endodomain in a pharmaceutically acceptable carrier.

A modified T cell is a T cell that has been transduced or transfected with one of the above-described vectors carrying the nucleic acid constructs encoding the chimeric proteins. Desirably, the T cell is a primary T cell, a CD8 (cytotoxic) T cell, or an NK T cell or other T cell obtained from the same mammalian subject into whom the modified T cell is administered or from another member of the mammalian species. In one embodiment, the T cell is an autologous human T cell or natural killer (NK) T cell obtained from the subject or from a bone marrow transplant match for the subject. Other suitable T cells include T cells obtained from resected tumors, a polyclonal or monoclonal tumor-reactive T cell. The T cell is generally obtained by apheresis, and transfected or transduced with the selected nucleic acid construct to express the chimeric protein in vivo.

Still other suitable T cells include an allogeneic or heterologous T cells useful as a universal T cell platform carrying the nucleic acid constructs described herein. In one embodiment, a human cytotoxic T cell may be employed. TALL-104 and TALL-103/2 cells are CD3-responsive lymphocytes, CD3$^+$TCRαβ$^+$ and CD3$^+$TCRγδ$^+$, respectively, derived from childhood T cell leukemia that display major histocompatibility complex nonrestricted, NK cell receptor-mediated tumoricidal activity, primarily dependent on NKG2D.[59,60,61] TALL cells display a broad range of tumor target reactivity that is NKG2D-dependent. Irradiated TALL-104 cells have been used for the treatment of metastatic breast and ovarian cancer due to their spontaneous (NK-like) cytolytic activity and safety.

These modified T cells, whether autologous or endogenous, are activated via signaling domains converting these T cells into potent cell killers. The autologous cells have an advantage over endogenous T cells in that they are not MHC restricted, which allows these T cells to overcome an immune surveillance evasion tactic used in many tumor cells by reducing MHC expression. The endogenous cells, such as the TALL cells, have an advantage in being universal, amenable to mass production, standardization and further cell engineering, to target FSHR$^+$ ovarian cancers.

In yet another embodiment, the modified T cell is also engineered ex vivo to inhibit, ablate, or decrease the expression of Forkhead Box Protein (Foxp1). In one embodiment, The T cells is engineered or manipulated to decrease Foxp1 before the T cell is transfected with a nucleic acid sequence as described above that encodes the chimeric protein comprising a ligand that comprises a naturally occurring or modified FSH sequence or fragment thereof, which ligand binds to human FSHR, linked to other T cell stimulating or targeting sequences. In another embodiment the manipulation to decrease or ablate Foxp1 occurs after the T cell is transfected with a nucleic acid sequence that encodes a chimeric protein or bi-specific protein as described herein. In one embodiment, the T cell has been pre-treated so that it does not express Foxp1 once the T cells are delivered to the subject. Most desirably, the Foxp1 in the modified T cell is ablated. The T cells may be treated with zinc finger nucleases, transcription activator-like effector nucleases (TALEN), the CRISPR/Cas system, or engineered meganuclease re-engineered homing endonucleases along with sequences that are optimized and designed to target the unique sequence of Foxp1 to introduce defects into or delete the Fox-P1 genomic sequence. By taking advantage of endogenous DNA repair machinery, these reagents remove Foxp1 from the modified T cells before adoptive transfer. Alternatively, the T cells may be co-transfected with another nucleic acid sequence designed to inhibit, decrease, downregulate or ablate expression of Foxp1. See, e.g., International Patent Application Publication WO2013/063019, incorporated by reference herein. Various combinations of these techniques may also be employed before or after the T cells have been modified by introduction of the nucleic acid construct.

Generally, when delivering the vector by transfection to the T cells, the vector is delivered in an amount from about 5 μg to about 100 μg DNA to about $1 \times 10^4$ cells to about $1 \times 10^{13}$ cells. In another embodiment, the vector is delivered in an amount from about 10 to about 50 μg DNA to $1 \times 10^4$ cells to about $1 \times 10^{13}$ cells. In another embodiment, the vector is delivered in an amount from about 5 μg to about 100 μg DNA to about $10^5$ cells. However, the relative amounts of vector DNA to the T cells may be adjusted, taking into consideration such factors as the selected vector, the delivery method and the host cells selected. The vector may be introduced into the T cells by any means known in the art or as disclosed above, including transfection, transformation, infection, extraporation or direct DNA injection. The nucleic acid construct may be stably integrated into the genome of the host cell, stably expressed as episomes, or expressed transiently.

The resulting modified T cells are prepared to expressed the nucleic acid constructs for adoptive therapy in a suitable pharmaceutical carrier. However, the chimeric bi-specific proteins may be administered as proteins in a suitable pharmaceutical carrier, as mentioned above.

All of the compositions and components described above may be used in the methods described herein for treating the cancers described herein and stimulating anti-tumor immune activity. Thus, methods of treating a cancer in a human subject are provided that comprise administering to a subject, any of the compositions as described above, in a pharmaceutically acceptable formulation or carrier.

The subject being treated by the method is in one embodiment a subject who has a cancer that expresses FSHR, including those cancers listed above. In another embodiment, the subject with FSHR-expressing cancer or tumor cells has been surgically treated to resect the tumor in question prior to administration of the composition described herein. In one embodiment, the subject is a female with ovarian cancer. In another embodiment, the female subject with ovarian cancer has been surgically treated to remove ovaries, fallopian tubes and/or uterus. Subjects having any of the other cancers enumerated above may be treated by appropriate surgery before or after application of these methods.

In one embodiment, the subject is administered a composition comprising a nucleic acid construct as described above. In another embodiment, the subject is administered a composition comprising a chimeric protein as described above. In one specific embodiment, the method of treating cancer in a human subject comprises administering to a subject in need thereof the bi-specific protein comprising a ligand that comprises an FSHβ sequence, which ligand binds to human FSHR, linked to a ligand that binds to NKG2D. In another embodiment, the composition is a viral vector carrying the nucleic acid construct to permit infection in vivo.

In another embodiment the method of treating cancer in a human subject comprises administering to a subject in need thereof a modified human T cell that comprises a nucleic acid sequence that encodes a chimeric protein comprising a FSH sequence, a modification or fragment of said FSH sequence, which ligand binds to FSHR, linked to nucleic acid sequences that encode T cell activating functions. In one embodiment, the T cell activating functions are provided by a nucleic acid sequence that encodes an extracellular hinge domain, a transmembrane domain, a co-stimulatory signaling region, and a signaling endodomain. In one embodiment, the modified T cell expresses any of the nucleic acid constructs described herein. In one exemplary embodiment, the modified T cell expresses the nucleic acid construct of FIG. 5 or similar constructs described herein. In another embodiment, upon administration the modified T cell does not express Forkhead Box Protein (Foxp1). In another embodiment, the modified T cell carries a nucleic acid construct that expresses or co-expresses sequences that ablate or decrease expression of Foxp1.

In still another embodiment, the modified human T cell is administered with clinically available PD-1 inhibitors. In still another embodiment, the modified human T cell is administered with clinically available including TGF-β inhibitors (including blocking antibodies). In still another embodiment, the modified human T cell is administered with clinically available IL-10 inhibitors.

These methods of treatment are designed to enhance the therapeutic activity of the T cells and prolong the survival of cancer patients. The therapeutic compositions administered by these methods, e.g., whether nucleic acid construct alone, in a virus vector or nanoparticle, as chimeric or bi-specific protein, or as modified anti-tumor T cell treated for adoptive therapy, are administered systemically or directly into the environment of the cancer cell or tumor microenvironment of the subject. Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration or intratumoral or intranodal administration. Routes of administration may be combined, if desired. In some embodiments, the administration is repeated periodically. In one embodiment, the composition is administered intraperitoneally. In one embodiment, the composition is administered intravenously. In another embodiment, the composition is administered intratumorally.

These therapeutic compositions may be administered to a patient, preferably suspended in a biologically compatible solution or pharmaceutically acceptable delivery vehicle. The various components of the compositions are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

Dosages of these therapeutic compositions will depend primarily on factors such as type of composition (i.e., T cells, vectors, nucleic acid constructs or proteins) the condition being treated, the age, weight and health of the patient, and may thus vary among patients. In one embodiment, the modified T cell-containing composition is administered in multiple dosages of between 2 million and 200 million modified T cells. Any value therebetween may be selected depending upon the condition and response of the individual patient. As another example, the number of adoptively transferred anti-tumor T cells can be optimized by one of skill in the art. In one embodiment, such a dosage can range from about $10^5$ to about $10^{11}$ cells per kilogram of body weight of the subject. In another embodiment, the dosage of anti-tumor T cells is about $1.5\times10^5$ cells per kilogram of body weight. In another embodiment, the dosage of anti-tumor T cells is about $1.5\times10^6$ cells per kilogram of body weight. In another embodiment, the dosage of anti-tumor T cells is about $1.5\times10^7$ cells per kilogram of body weight. In another embodiment, the dosage of anti-tumor T cells is about $1.5\times10^8$ cells per kilogram of body weight. In another embodiment, the dosage of anti-tumor T cells is about $1.5\times10^9$ cells per kilogram of body weight. In another embodiment, the dosage of anti-tumor T cells is about $1.5\times10^{10}$ cells per kilogram of body weight. In another embodiment, the dosage of anti-tumor T cells is about $1.5\times10^{11}$ cells per kilogram of body weight. Other dosages within these specified amounts are also encompassed by these methods.

In another embodiment, a therapeutically effective adult human or veterinary dosage of a viral vector is generally in the range of from about 100 μL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles virus.

Administration of the protein-containing compositions may range between a unit dosage of between 0.01 mg to 100 mg of protein (which is equivalent to about 12.5 μg/kg body weight).

Methods for determining the timing of frequency (boosters) of administration will include an assessment of tumor response to the administration.

In still other embodiments, these methods of treating cancer by administering a composition described herein are part of a combination therapy with various other treatments or therapies for the cancer.

In one embodiment, the methods include administration of a cytokine, such as IL-7 treatment as tumor-specific host conditioning strategies. Exogenous administration of IL-7 further promotes the in vivo activity specifically of Foxp1-deficient T cells. In another embodiment, the method further comprises administering to the subject along with the compositions described herein, an adjunctive anti-cancer therapy which may include a monoclonal antibody, chemotherapy, radiation therapy, a cytokine, or a combination thereof. In still another embodiment the methods herein may include co-administration or a course of therapy also using other small nucleic acid molecules or small chemical molecules or with treatments or therapeutic agents for the management and treatment of cancer. In one embodiment, a method of treatment of the invention comprises the use of one or more drug therapies under conditions suitable for cancer treatment.

As previously mentioned surgical debulking, in certain embodiments is a necessary procedure for the removal of large tumor masses, and can be employed before, during or after application of the methods and compositions as described herein. Chemotherapy and radiation therapy, in other embodiments, bolster the effects of the methods described herein. Such combination approaches (surgery plus chemotherapy/radiation plus immunotherapy) are anticipated to be successful in the treatment of many cancers along with the methods described herein.

In still further embodiments, the methods of treating a subject with an FSHR-expressing cancer or tumor include the following steps prior to administration of the compositions described herein. In one embodiment, the methods include removing T cells from the subject and transducing the T cells ex vivo with a vector expressing the chimeric protein. In another embodiment, the removed T cells are treated to ablate or reduce the expression of Fox-P1 in the T cells before or after transduction of the removed T cells with the nucleic acid construct described herein. In another method, the removed, treated T cells are cultured prior to administration to remove Foxp1 from the cells ex vivo. Another method step involves formulating the T cells in a suitable pharmaceutical carrier prior to administration. It is also possible to freeze the removed and treated T cells for later thawing and administration.

The methods of treatment may also include extracting T cells from the subject for modification and ex vivo cell expansion followed by treating the subject with chemotherapy and depleting the subject of lymphocytes and optionally surgically resecting the tumor. These steps may take place prior to administering the modified T cells or other compositions to the subject.

The invention is now described with reference to the following examples. These examples are provided for the purpose of illustration only. The compositions, experimental protocols and methods disclosed and/or claimed herein can be made and executed without undue experimentation in light of the present disclosure. The protocols and methods described in the examples are not considered to be limitations on the scope of the claimed invention. Rather this specification should be construed to encompass any and all variations that become evident as a result of the teaching provided herein. One of skill in the art will understand that changes or variations can be made in the disclosed embodiments of the examples, and expected similar results can be obtained. For example, the substitutions of reagents that are chemically or physiologically related for the reagents described herein are anticipated to produce the same or similar results. All such similar substitutes and modifications are apparent to those skilled in the art and fall within the scope of the invention.

Example 1: Generation of Human and Mouse FSHR-Targeting Constructs

We generated a new fully murine construct as described herein against mouse FSHR that includes the mouse version of all signals successfully used in human patients. To target FSHR, we synthetized a construct expressing a signal peptide, followed by the two subunits (alpha and beta) of endogenous FSH, separated by a linker (See FIG. 1). This targeting motif was cloned in frame with a hinge domain from murine IgG, such as CD8α, followed by the transmembrane domain of CD8α, the intracellular domain of co-stimulatory mediator (e.g., murine 4-1BB or CD28), finally, the activating CD3ζ domain.

We have also generated constructs with the corresponding human sequences (see FIG. 5, Table 1, SEQ ID NOS: 1 and 2). Human variants of the FSHR-expressing constructs are generated to define the leading formulation and demonstrate the relevance of experiments in mice. Human HLA-A2+ T cells (>50% of Caucasians are A2+) from healthy donors are transduced with retro- or lentiviral stocks containing the FSH-targeted construct, which is optimized for cytotoxic testing.

In frame constructs similar to the mouse sequences described above are generated to compare CD28 vs. 4-1BB/CD137. CD28 is an alternative intracellular co-stimulatory motif because, although T cells expressing 4-1BB/CD137 exhibited enhanced persistence in xenograft models in published experiments with CAR-T cells, it is unclear that long-term survival of T cells is preferable over multiple injections. In addition, the two human variants of the alpha subunit of human FSH (NM_000735.3 vs. NM_001252383.1) are tested. These two subunits have different lengths and have the potential to promote different binding affinities.

Overall, the 8 variants cloned (in frame) for expression into viral vectors are: 1) CGα (long)+4-1BB; 2) CGα (long)+CD28; 3) CGα (short)+4-1BB; and 4) CGα (short)+CD28 (see FIG. 8).

Other constructs are designed using only the beta subunit of FSH (which provides specificity for FSHR binding) and with a 15 aa binding region of the beta subunit that also binds FSHR, e.g., the fragment of amino acids 19-32 of SEQ ID NO: 2 of FSHβ or other FSHβ fragments identified above.

Example 2: FSH Constructs Respond Specifically to FSHR+ Tumor Cells

Retroviral (pSFG) vs. lentiviral (pELNS) vectors are tested to transduce the FSHR-carrying construct into human T cells. There is no formal demonstration that lentiviral vectors are superior for ex vivo transduction. Most importantly, concerns regarding the risk of insertional oncogenesis after gene transfer in the T cell are negligible after a decade-long safety using retroviral vectors. The pSFG vector in particular has been used many times for similar retroviral transduction of T cells in clinical trials[41,42].

Figure 2A:
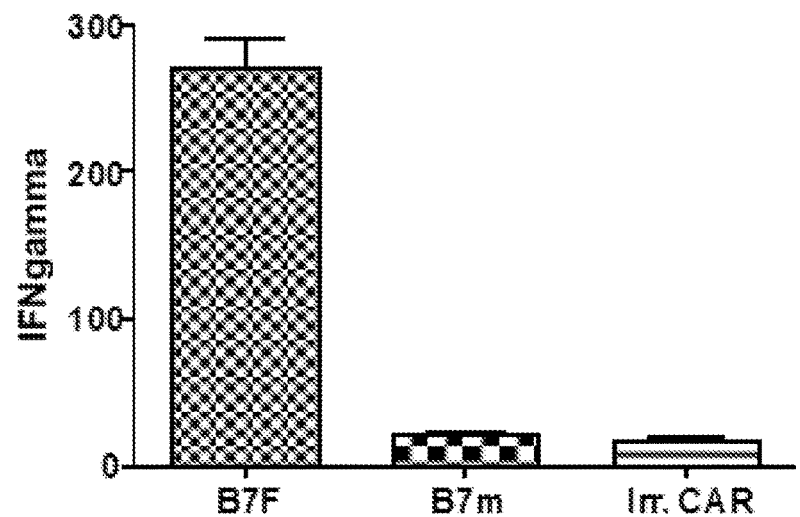
FIG. 2A is a bar graph showing that T cells containing the nucleic acid sequence encoding the chimeric protein expressing the ligand to FSH receptor (FSHCER-CD8) respond specifically to FSHR-expressing B7F tumor cells. Positively transduced (GFP+) T cells carrying the FSHR-targeting CER (FSHCER-CD8; small checkerboard pattern) of FIG. 1 or an irrelevant mesothelin-targeting (K1) CAR (large checkerboard pattern) were co-incubated (1:20) for 6 hours with ID8-Defb29/Vegf-a tumor cells (B7) transduced with FSHCER-CD8 or an empty vector (ID-8; Irrelevant CAR). IFN-γ was quantified in supernatants (pg/mL). The FSH chimeric protein-transfected (or FSHR-targeting) modified T cells secreted interferon-γ, an activation marker, in response to mouse B7 ovarian tumor cells that overexpress FSHR. The mesothelin-targeting T cells do not secrete Interferon-γ against the FSHR-overexpressing tumor cell line B7F. Likewise the T cell expressing the FSH chimeric protein is not activated with a tumor cell B7 that does not express FSHR.
Figure 2B:
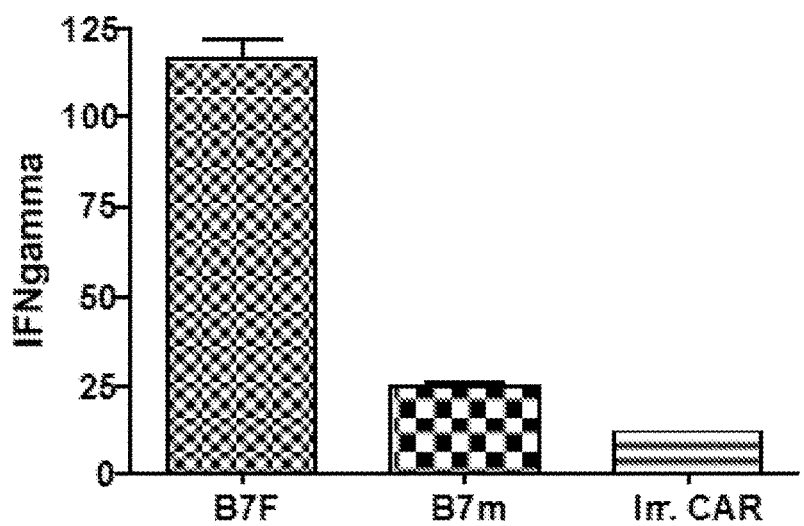
FIG. 2B is a bar graph showing the same analysis with a FSHCER-CD4 construct.

Retroviral or lentiviral stocks expressing these constructs are generated and used to transduce human T cells from healthy HLA-A2 donors (>50% Caucasians). Retroviral stocks were used to transduce CD3/CD28-activated T cell splenocytes, which were FACS-sorted based on co-expression of GFP. The specificity of the binding of modified T cells expressing the FSH nucleic acid constructs of Example 1 was then tested against FSHR- or mock-transduced ID8-Defb29/Vegf-a ovarian cancer cells. As shown in FIG. 2, co-incubation of T cells transduced with the FHSR targeting construct, but not T cells carrying an irrelevant mesothelin-targeting construct (K1), elicited the secretion of IFN-γ. Further supporting the specificity of FSHR recognition, IFN-γ secretion did not occur in the presence of mock-transduced (naturally FSHR-) tumor cells.

Figure 3:
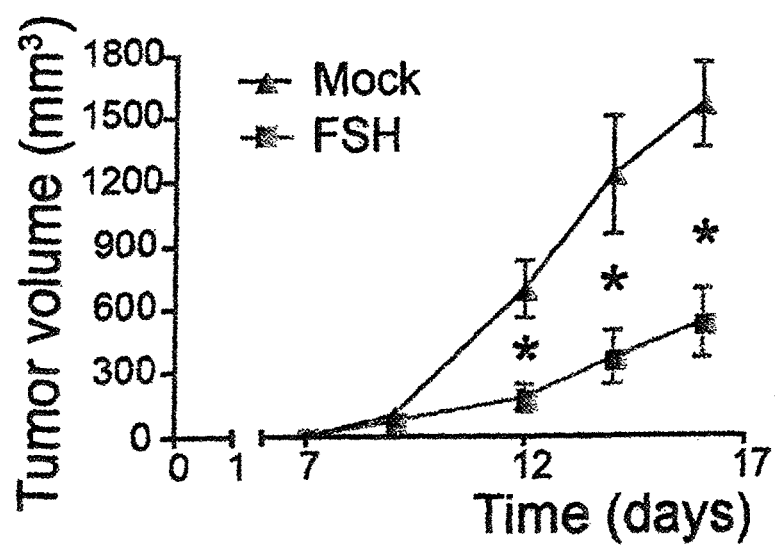
FIG. 3 is a graph showing that T cells containing the nucleic acid sequence encoding the chimeric protein expressing the ligand to FSH receptor delays progression of established FSHR+ tumor cells. A7C11 syngeneic (B6) breast cancer cells that overexpress FSHR were administered into the flank of two groups of mice (5 mice/group). Four days after tumor cell administration, $10^6$ FSHR-targeting modified T cells (■) or mock (pBMN) transduced T cells (▲) were adoptively transferred intraperitoneally. The progression of the tumor growth in the mice treated with the chimeric protein-carrying T cells is delayed.
Figure 4A:
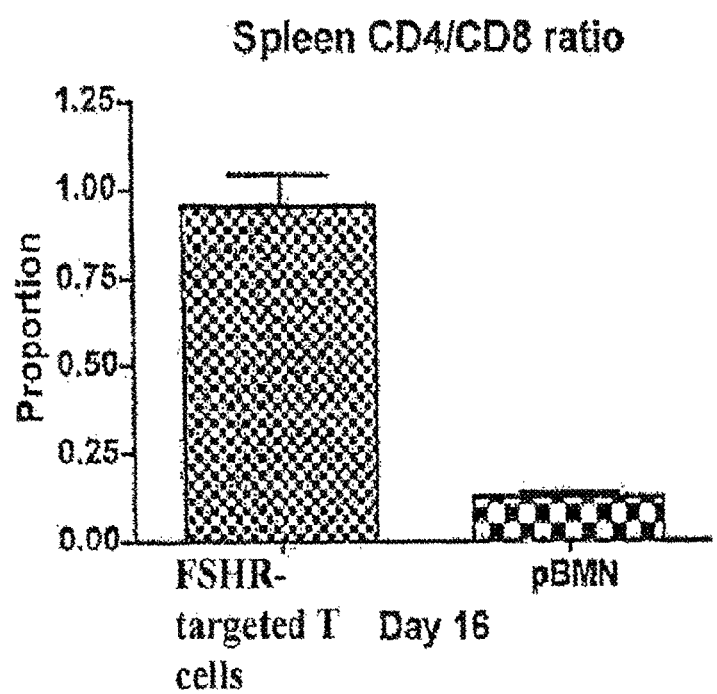
FIG. 4A is a bar graph showing CD4/CD8 ratio in the splenic cells of mice injected with the chimeric protein or the mock pBMN T cells in equal numbers on day 16 post-administration of the T cells carrying the chimeric protein or the mock protein.
Figure 4B:
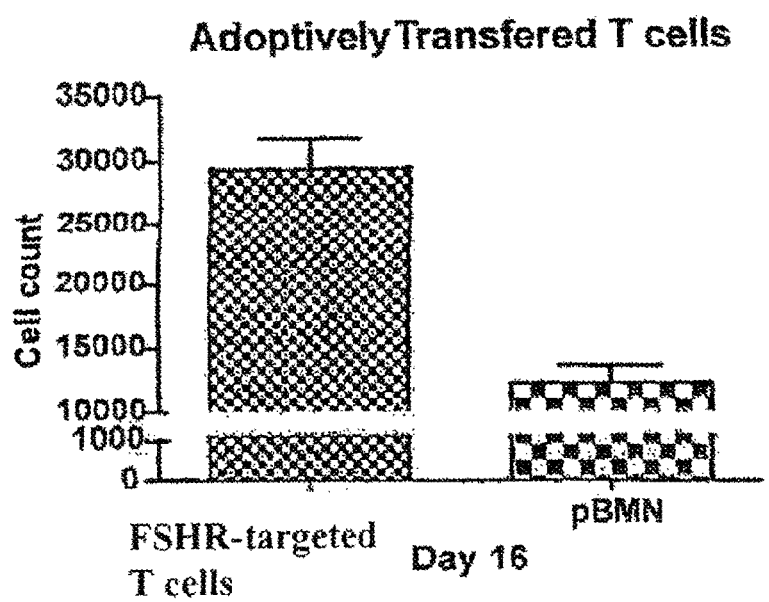
FIG. 4B is a bar graph showing the cell count of adoptively transferred T cells of the mice treated as described as in FIG. 4A on day 16.
Figure 4C:
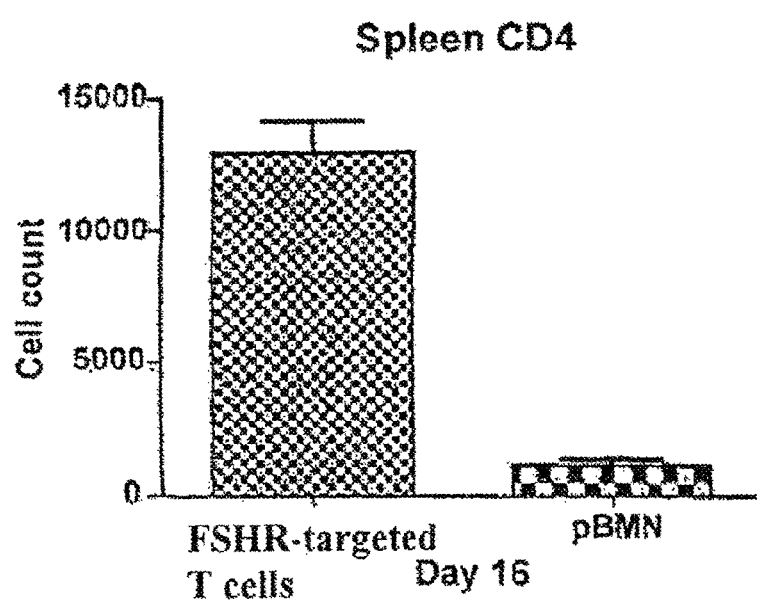
FIG. 4C is a bar graph showing the individual spleen CD4 counts of the splenic cells from the mice of FIG. 4A on day 16.
Figure 4D:
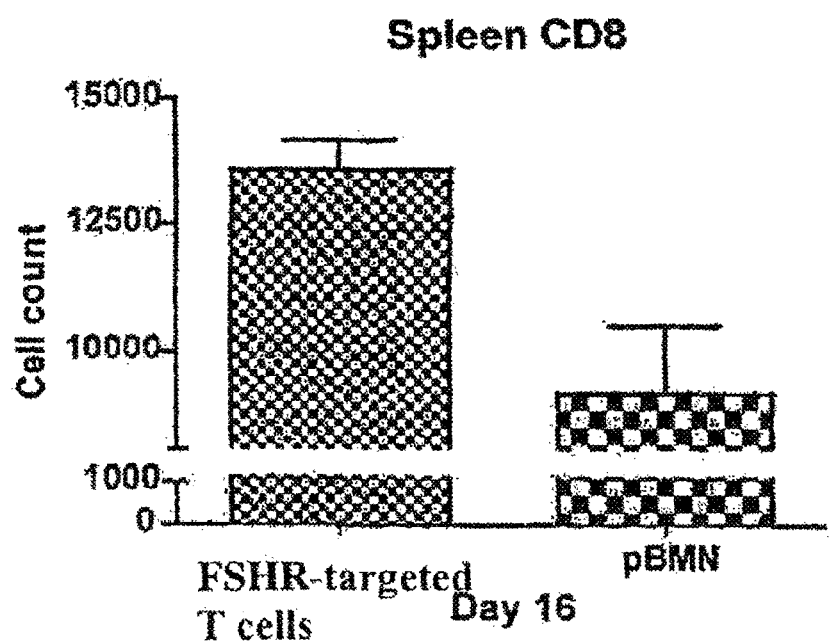
FIG. 4D is a graph showing the CD8 cell counts of the splenic cells from the mice of FIG. 4A on day 16. As indicated in the flow cytometric data (data graphs not shown) of these spleen cells gated on CD8 and CD4 markers (not shown), these figures also demonstrate that there is an increased number of transfected cells, both CD4 and CD8, in the spleen of mice administered the chimeric protein bearing T cells, as compared to the mock protein bearing T cells.

Example 3: Intratumoral Administration of FSH Construct-Expressing T Cells Delays the Progression of FSHR+ Breast Tumors To gain some insight into the potential effectiveness and safety of FSHR-targeting modified T cells in vivo in immunocompetent mice, we also transduced A7C11 breast cancer cells, a cell line generated from an autochthonous p53/KRas-mutated tumor, with mouse FSHR. Syngeneic mice were then challenged with flank tumors and administered identically treated $10^6$ FSHR-targeting modified T cells or mock transduced T cells through intraperitoneal injection. As shown in FIG. 3, a single administration of FSHR-targeting modified T cells was sufficient to significantly delay the progression of established flank tumors, without noticeable side effects. These results support the use of FSHR-targeting modified T cells against ovarian orthotopic tumors, alone or in combination with other clinically available immunotherapies.

The use of mouse FSH as a targeting motif is much more predictive of the effects of FSHR-targeting modified T cells than the use of human FSHR targeting constructs in immunodeficient mice, because: 1) T cells expressing mouse FSH target potentially unidentified healthy cells expressing endogenous FSHR (unlike T cells expressing human FSH administered into immunodeficient mice); 2) certain T cells, e.g., CER-T, cells can boost polyclonal anti-tumor immunity by enhancing pre-existing T cell responses through antigen spreading and decreasing the immunosuppressive burden; and 3) interactions between FSH and its specific receptor are highly conserved.

To demonstrate the cytotoxic potential of the FSHR-construct-containing T cells specifically against FSHR+ tumor cells, we again incubated the FSHR-constructs or mock-transduced T cells with FSHR+ID8-Defb29/Vegf-a33 (ovarian tumor) or A7C1134 (a cell line generated in the lab from autochthonous p53/KRas-mutated breast tumors34) cells (40:1 ratio for 24 h.), and cytotoxic killing was determined by counting Tripan blueneg (live) tumor cells. As shown in FIGS. 7A and 7B, FSH CER T cells, but not mock-transduced lymphocytes eliminated both types of tumor cells. Comparable results were obtained in a MTS assay (not shown), further supporting that FSH targeting motifs are able to elicit CER-mediated T cell cytotoxic activity in a FSHR-specific manner.

Example 4: The Effectiveness Vs. Toxicity of FSH Ligand-Expressing Modified T Cells in Preclinical Ovarian Cancer Models in Immunocompetent Hosts To define the immunological consequences of using FSHR-targeting modified T cells in immunocompetent preclinical tumors models that include all healthy tissues where endogenous FSH could potentially bind (as it will happen in patients), we have generated new nucleic acid constructs with the mouse counterparts of all targeting and activating domains. See Table 3, FIG. 6C and SEQ ID NOs 4 and 5.

We test the hypothesis that FSHR-targeting modified T cells show selective activity on the FSHR-expressing cells, impairing tumor progression, while not harboring significant adverse effects in the mouse. These results define the effect of this promising therapy on ovarian cancer and ensure its safety for the future translation of this approach to the clinic.

We use aggressive orthotopic ID8-Vegf/Defb29 tumors which have been transduced and selected with mouse FSHR. We validate the general applicability of selected findings using transduced parental ID8 cells and/or, an autochthonous p53-dependent inducible tumor model or our derived cell lines.

Example 5. Mouse Clinical Trial: Define the Effectiveness of FSHR-Targeting Modified T Cells Against Human Ovarian Cancers We generated constructs with all human domains (see FIG. 5), which are used in our established cohort of primary tumor-derived xenografts in NSG mice. By using the same patients' tumors and T cells, we mimic a limited clinical trial that recapitulates the heterogeneity of clinical ovarian cancer. We hypothesize that FSHR-targeting modified T cells are effective against established FSHR+ ovarian cancers from different patients, and synergize with combinatorial interventions targeting the TME.

By establishing the effectiveness and potential toxicity of FSHR-targeting modified T cells in a variety of preclinical models, we provide a mechanistic rationale for the testing of such T cells as a potential therapy against ovarian cancer. By using FSHR as a specific tumor target and a ligand comprising an FSH sequence as targeting motif, we overcome some of the challenges that have prevented the success of a variety of technologies against epithelial tumors.

To define full spectrum of activities of FSHR-targeting modified T cells in vivo in immunocompetent hosts, we have generated fully murine FSHR-targeting modified T cells. (CD45.2+) established (FSHR+ and FSHR−) ovarian tumor-bearing mice (n≥10/group) are treated with (CD45.1+, congenic) $10^6$ i.p. anti-FSHR-targeting modified T cells 7 d. after tumor challenge. Control mice receive mock transduced T cells. We compare survival, as an indisputable readout of effectiveness. Additional injections of FSHR-targeting modified T cells are administered depending on these results. In different mice, at days 14, 21 and 28 after tumor challenge, we track the homing and persistence of (specifically CD45.1+) transferred CD4 and CD8 T cells. Samples from spleen, draining (mediastinal) lymph nodes, bone marrow and tumor beds (peritoneal wash) are included. An exhaustive analysis of activation (e.g., CD44, CD69, CD27, CD25) vs. exhaustion (e.g., PD-1, Lag3) markers in transferred lymphocytes is included. In addition, possible central memory differentiation of (congenic) FSHR-targeting modified T cells in BM and lymph nodes is analyzed, as a potential predictor of long-term engraftment and durable protection.

Example 6: Effects of FSHR-Targeting Modified T Cells on Pre-Existing Anti-Tumor Immunity We determine the effects that FSHR-targeting modified CER-T cells have on ongoing anti-tumor immune responses, through antigen spreading and reduction of the immunosuppressive burden. For that purpose, we treat tumor-bearing mice with FSHR-targeting modified CER-T cells vs. mock-transduced T cells and FACS-sort the endogenous (CD3+ CD8+CD45.2+) T cells from tumor and lymphatic locations, at days 7 and 14 after adoptive transfer (days 14 and 21 after tumor). Magnitude of anti-tumor immune responses_attributable to pre-existing T cells influenced by treatment, are quantified through IFNγ and Granzyme B ELISPOT analysis. Activation vs. exhaustion markers in endogenous T cells additionally define the effects of FSHR-targeting modified T cells. To define immune protection against recurrences potentially elicited by these combinatorial interventions, mice are re-challenged if they rejected their tumors.

Example 7—Short and Long-Term Toxicity Potentially Induced by FSHR-Targeting Modified T Cells The main concern in T cell adoptive transfer protocols in the short term is the occurrence of a cytokine release syndrome, a systemic inflammatory response that induces non-infective fever and is associated with high levels of TNFα and IL-6.

We first monitor temperature and cytokine levels in treated vs. control mice, besides obvious signs of disease (e.g., ruffled fur). If a cytokine release syndrome was a frequent occurrence, we define whether the use of corticoids or IL6 depletion could make it a manageable event. The FSHR has not been reported to be expressed in normal tissue outside of the ovary or the testes; therefore, we expect no long term side effects. However, we monitor any macroscopic alterations in treated mice for up to 4 months after treatment.

Example 8—Mouse Clinical Trial in Patient-Derived Xenografts

We engraft fresh advanced ovarian carcinoma that we receive (~2-3 specimens/month). Fresh specimens are delivered through a courier within 2 h. after resection, and ~1 mm3 chunks are engrafted into the ovarian bursa of NSG (severely immunodeficient) mice, through an optimized surgical procedure. Importantly, we receive peripheral blood from the same patients, and buffy coats are immediately cryopreserved. In the last 2 months, we have challenged ~35 mice with 7 different specimens. Most tumors become palpable and visible in ~45 days although their progress is slow. Approximately 2-3 new fresh specimens arrive every month. We generate xenografts for ≥10 primary tumors from different patients. Mice are used to define the effectiveness of FSHR-targeting modified T cells against heterogeneous human ovarian tumors. For that, we CD3/CD28-expand and transduce the FHSR-targeting construct on T cells from the same patient, thus mimicking its potential clinical application.

Figure 1:
FIG. 1 is a schematic of one construct (i.e., a nucleic acid construct or amino acid construct) that expresses the chimeric endocrine receptor (CER), FSH ligand protein, in T cells.

We have generated FSH-targeting modified T cells with the corresponding human endogenous FSH, the hinge and transmembrane domains, and the co-stimulatory 4-1BB and activating CD3 motifs shown in FIG. 1 (all human sequences—see FIG. 5). We determine the expression of FSHR in each xenograft through Western-blot analysis, to define how it predicts effectiveness. T cells from healthy donors with matching HLAs can be transduced and transferred.

To define the effectiveness of FSHR-targeting modified T cells against ovarian cancer, we use peripheral blood autologous to our engrafted human ovarian cancer specimens (≥3 mice/tumor; 10 different patients). T cells are expanded and transduced with human FSHR-targeting nucleic acid constructs or the empty vector (and/or irrelevant human CAR T19), and adoptively transferred into xenograft-bearing NSG mice challenged at the same time. Tumor growth is monitored through palpation and ultrasound, and mice are sacrificed when tumors protrude through the abdomen, or earlier if the mice show signs of distress or advanced disease. Tumor growth, metastases and survival are quantified as a readout of effectiveness. How tumor growth is affected as a function of the expression of FSHR is defined, using WB analysis in matching surgical specimens. We dissociate tumor specimens to determine the accumulation of transferred T cells in the presence vs. the absence of the target (NSG mice do not have endogenous lymphocytes). Persistence of FSHR-targeting modified T cells at bone marrow and lymph node locations is determined and correlated with the expression of the targeted hormone receptor (FSHR) and effectiveness.

Example 9: Modulating Immunosuppression to Enhance the Effect of FSHR-Targeting Modified T Cells Activity Against Ovarian Cancer A potential challenge of adoptive T cell transfer interventions against solid tumors is the prospect that immunosuppressive networks in the TME abrogate the protective activity of exogenous T cells. To modulate the tumor microenvironment in order to decrease its immunosuppressive effects, and increase survival, adjunctive methods are applied with the FSHR-targeting modified T cells. To elicit tumor rejection and sustained protection, the FSHR-targeting modified T cells are combined with the administration of clinically available PD-1 inhibitors (or PD1 blockers alone in control groups). Effectiveness as a function of PD-L1 expression in tumor cells is monitored. Alternatively, we block other immunosuppressive pathways in the ovarian cancer microenvironment in mice receiving FSHR-targeting modified T cells, including TGF-β (for which blocking Abs have been recently developed) and IL-10.

In summary, the above examples demonstrate that we targeted a G-protein coupled receptor (FSHR) that is expressed on the surface of ovarian cancer cells in most tumors and has not been used in T cell based interventions. To enhance both specificity and receptor:ligand interactions, we use the endogenous hormone as a targeting motif, thereby providing a rationale for the clinical testing of FSHR-targeting modified T cells carrying the human counterparts of these motifs. We use the endogenous ligand (a hormone), as opposed to anti-FSHR antibody or antibody fragments as a ligand to ensure effectiveness or specificity. We show that modified T cells directed against FSHR are safe and do not induce obvious toxicity in vivo.

Most relevant for this application, the cytotoxic activity of modified T cells targeting FSHR+ tumor cells boosts pre-existing lymphocyte responses through antigen spreading, thus enhancing polyclonal anti-tumor immunity. In addition, we define whether combinatorial targeting of suppressive networks operating in the ovarian cancer microenvironment unleashes both FSHR-targeting modified T cells and tumor-infiltrating lymphocytes from tolerogenic pathways that could dampen their protective activity.

Thus, this application is innovative at multiple conceptual and experimental levels. We leverage a collection of freshly, orthotopically engrafted primary ovarian cancer xenografts to reflect the heterogeneity of the human disease in terms of FSHR expression and response variability. Specifically, we anticipate the above studies to demonstrate that ovarian cancer-bearing mice treated with FSHR-targeting modified T cells show significantly increased survival (even tumor rejection in some cases), compared to controls receiving mock-transduced T cells. Correspondingly, we identify FSHR-targeting modified T cells in vivo in treated mice for relatively long periods, as opposed to control T cells. Because the bone marrow is a reservoir of memory T cells in our system that is where we see niches of persistent FSHR-targeting modified T cells. FSHR-targeting modified T cells are less sensitive to mechanisms of exhaustion at tumor beads. Together, these results are interpreted as evidence for the therapeutic potential of FSHR-targeting modified T cells, and pave the way for subsequent clinical testing.

The data is anticipated to demonstrate that FSHR-targeting modified T cells induce a significant boost in the suboptimal but measurable anti-tumor activity of pre-existing T cells, as quantified by ELISPOT analysis. The combined activity of FSHR-targeting modified T cells and endogenous lymphocytes correspondingly confers protection against recurrence in those mice rejecting established tumors. This underscores the potential of FSHR-targeting modified T cells to elicit polyclonal immunological memory against tumor relapse, even if tumors lose targeted FSHR in the process.

The data is expected to show absence of significant adverse effects in the long-term (e.g., autoimmunity) for ovarian cancer, as expression of FSHR is restricted to the ovary (including all nucleated cells). We cannot rule out that the acute administration of FSHR-targeting modified T cells will result in flu-like symptoms, but it is unlikely that they will cause a cytokine-release syndrome. Together, these data further support using FSHR-targeting modified T cells in ovarian cancer patients.

The data is anticipated to demonstrate that >50% of primary tumors eventually grow exponentially in NSG mice and allow serial engraftment into different mice. 50-70% of these tumors express surface FSHR. Although we have shown the feasibility of engrafting human cultured ovarian cells (which could be used as a back-up or complementary approach), this resource recapitulates the heterogeneity of the human disease.

The data is anticipated to show that FSHR-targeting modified T cells are also effective against xenografted human ovarian cancers that express FSHR, but not against FSHR– tumors. Correspondingly, we anticipate that tumors with higher levels of FSHR expression are superior responders. Accordingly, we find enhanced persistence of modified T cells, stronger infiltrates (due to FSHR-induced proliferation) and less exhaustion in $FSHR^{high}$ tumor-bearing hosts. These results further support both the specificity and the therapeutic potential of FSHR-targeting compositions, as described herein.

Combination of PD-1 inhibitors with FSHR-targeting modified T cells promote the rejection of PD-L1+ tumors, while only a significant delay in malignant progression is observed using individual treatments. Given the emerging clinical success of PD-1 blockers, we expect that they are overall superior to other interventions targeting immunosuppression, which could nevertheless be more effective in PD-L1-tumors. Combinatorial interventions integrating cellular and molecular immunotherapies has obvious implications for subsequent clinical testing.

Example 10—Expression of CER Variants in Human T Cells

We use peripheral blood from the aphaeresis of healthy HLA-A2+ donors (>50% of Caucasians), to minimize allogeneic reactions when transduced T cells are co-incubated with (A2+) tumor cells. We use methods and resources as described[5,29,30 44,45]. Briefly, monocytes are depleted from the apheresis product and T cells are expanded in 5% normal human AB serum using beads conjugated anti-CD3 (OKT3) and anti-CD28 (clone 9.3) antibodies (3:1 bead/CD3+ cell ratio). On day 1 after stimulation, T cells are exposed to retro- or lentivirus supernatant encoding the FSH-targeted constructs variants (MOI~3), on retronectin coated plates in the presence of 50 UI/mL of IL-2 and 1 ng/mL of IL-7, followed by spinoculation (1000 g, 45 min, 4° C.). On day 2, media are changed and spinoculation repeated, followed by up to 12 days of expansion. After completion of cell culture, magnetic beads are removed through magnetic separation and the cells are washed and resuspended in PlasmaLyte A (Baxter). The efficiency of transduction is determined by flow cytometry using primary antibodies against human FSHβ (Clone 405326) expressed outside infected cells, and PE-labeled anti-mouse IgG as secondary antibodies. The transduction of human HLA-A2+ T cells is optimized for cytotoxic testing of all variants.

Example 11—the Anti-Tumor Activity of FSH-Targeted CER Variants In Vitro

An in vitro luciferase assay is used to test the effectiveness, i.e., cytotoxic activity, of the FSH-targeted T cell variants generated as described in the Examples above. We use human HLA-A2+ OVCAR3 ovarian cancer cells[19], which are also known to express high levels of FSHR[20,46]. By using HLA-A2+ OVCAR3 T cells (expressing the most common HLA type present in 50% of the Caucasians and 35% of African-Americans), we can use T cells from a wide variety of donors without eliciting an alloimmune response. We thereby restrict the elicitation of cytotoxic killing to specific recognition of the FSHR receptor. We also measure IFN-γ production by transduced T cells in response to FSHR-expressing tumor cells. The two FSHR-expressing T cell variants that show the best combined cytotoxic activity and IFN-γ production are selected for subsequent in vivo testing.

Transfection with the retroviral vector pBABE-luc-puro makes the OVCAR3 cells express firefly luciferase spontaneously, and allow selection by a puromycin resistance gene.

Human HLA-A2+ FSH-targeted construct-transduced T cells as described herein are used as effectors. If more than 60% of the T cells are transduced, the T cells are considered ready to use in the assays. If less than 60% of the T cells are transduced, we enrich for the transduced T cells by FACS-sorting for the FSH+ cells.

After clonal selection and expansion of luciferase expressing OVCAR3 (OVCAR3-luc), we plate 10,000 cells per well and coculture with T cells expressing the different FSH construct variants at ratios 1:1 (tumor cells: T cells), 1:5, 1:10 and 1:20. We also have a condition without T cells as negative control (no cell death) and another treated with Triton X as positive control for maximal tumor cell death. 18 hours after plating the cells in co-culture we remove the media, wash the wells, lyse the cells and add the luciferase substrate. We measure the amount of luciferase signal to determine the specific lysis of OVCAR3-luc cells by the FSH-targeted CER T cells.

Example 12—Production of IFN-Γ in Response to FSHR by all CER T Cell Variants

Another parameter potentially important for therapeutic effectiveness is the production of effector cytokines that may influence the immunoenvironment in vivo.

Complementarily, we co-culture OVCAR3 cells and T cells expressing the different variants of FSH-targeted construct and collect the supernatants at 18 hours for determining IFNγ production by ELISA with at 1:1, 1:10 and 1:20 tumor cell to T cell ratios. If time permits, we also determine IFN-γ production by intracellular staining of FSH-targeted transfected T cells incubated with FSHR+ tumor cells, as well as other cytokines such as TNF-α (ELISA) and granzyme B (intracellular staining).

These experiments are run in (at least) triplicates and repeated 3 times, to achieve statistical significance (P<0.05) using the Mann-Whitney's test. We identify two FSH-targeted construct-transfected T cell variants for further investigation and development in an in vivo system. We select the FSH-targeted CER variant that provides, in order of priority: 1) The highest % of specific OVCAR3-luc cell lysis at the different ratios; 2) the highest levels of IFN-γ secretion are selected. Where there are different best candidates at different ratios, we choose the one with the highest specific lysis at a lowest ratio. If all variants show similar activity, we prioritize the use of retroviral vectors, the inclusion of CD28 instead of 4-1BB, and the shorter CGα variant. If there are no differences we choose the variant that shows higher transduction efficiency.

If FSHR-targeted killing of OVCAR3 cells is suboptimal, we use Caov-3 ovarian cancer cells (ATCC#HTB-75), which also co-express FSHR and HLA-A2. In this case, this cell line is used for subsequent in vivo testing.

Example 13—FSHR Construct Variants Tested In Vivo in Ovarian Cancer Xenografts

We compare the in vivo efficacy of the two leading CER T cell variants identified in the Examples above. OVCAR3 cells (HLA-A2+[19]; FSHR+[20]) are engrafted into the ovarian bursa of NSG (severely immunodeficient) mice[9]. Orthotopic tumor-bearing mice are treated with HLA-A2+CER T cells as follows. Tumor chunks (~1 mm$^3$) are derived from TOV-21G ovarian clear cell carcinoma cells implanted into the flank of immunodeficient mice engrafted into the ovarian bursa of NSG mice in ~1 month. The challenged ovary was taken by malignant growth and compared to the left contralateral ovary. The tumor (figure not shown) was particularly aggressive and grew in ~21 days. We have also challenged mice with either tumor chunks (right ovary) or single cell suspensions from the same freshly dissociated primary ovarian cancer specimens.

To define the effectiveness of FSH-targeted construct-transduced T cells against FSHR+ ovarian cancer, we use the two CER T cell variants that show the best combined cytotoxic activity and IFN-γ production. If all variants show similar activity, we prioritize the use of retroviral vectors, the inclusion of CD28 instead of 4-1BB, and the shorter CGα variant. Mice showing established orthotopic ovarian tumors of similar size by ultrasound and/or palpation (≥5 mice/group) receive T cells transduced with the two variants of FSHR-targeting construct-transduced, or mock-transduced, T cells as an alternative control. If <60% transduction is achieved, positively transduced T cells are FACS-sorted and allowed to rest for 2 h before treatment. 10$^7$ FSHR-target construct-transduced T cells/injection and two injections 14 days apart (i.p. in PBS) are administered for these analyses. Tumor growth is monitored through palpation and ultrasound, and mice are sacrificed when tumors protrude through the abdomen, or earlier if the show signs of distress or advanced disease. Tumor growth, metastases and survival are first quantified as an undisputable readout of effectiveness.

Example 14—the Persistence of the Two CER T Cell Variants In Vivo in Tumor-Bearing Mice An important parameter associated with long-term protection is the persistence of central memory FSH-targeted construct-transduced T cells that can produce new waves of T cell effectors upon tumor recurrence. To determine what CER T cell variant persists for longer time in vivo, we identically treat different OVCAR3-growing mice (≥5 mice/ group) with FSH-targeted construct-transduced T cells, and monitor where they gather and persist. First, the accumulation of transferred T cells at days 14 and 28 after adoptive transfer are determined through FACS analysis using dissociated tumor tissue, bone marrow (a reservoir of central memory T cells), lymph nodes and spleen samples. We use human CD3, as NSG mice do not have endogenous lymphocytes. Their memory attributes (CD62L+CD45RA-CD122+CD127+) at lymphatic and BM locations are determined. If mice reject tumors upon the administration of FSH-targeted T cells, we re-challenge them with OVACR3 flank tumors, and compare tumor progression with that in naïve (untreated) NSG mice.

Based on our previous observations, we anticipate that 5 mice per group should provide a 5% significance level and 95% power to detect differences of 20% or greater, using Mann-Whitney's or Wilcoxon's tests. Experiments use at least 5 mice/group (plus a repetition) and are analyzed according to these statistical parameters. We thereby identify the lead FSH-targeted T cell variant that is used for final preclinical optimization. The selected candidate shows a combination of, in order of importance: 1) strongest effectiveness against established tumor growth; 2) central memory differentiation at lymphatic or bone marrow locations; and 3) superior overall persistence in vivo.

We theorize that persistence of FSH targeted T cells is important for long-term remissions, based on clinical evidence treating leukemia[12,38,48]. If both FSH target construct-transduced T cell variants express CD28 and do not persist for at least 2 weeks, we also test the in vivo effectiveness of T cells carrying the constructs using 4-1BB. If comparable tumor reduction was achieved, we would select CD28 as a co-stimulatory domain.

We complement these experiments with the use of Caov-3 ovarian cancer cells, which express even higher levels of the FSH Receptor and are HLA-A2$^+$.

Example 15: Maximum Tolerated Dose (MTD) for Single Dose Administrations

The experimental plan to define MTD involves: (1) administering a single dose ($2\times10^6$, $10^7$ and $5\times10^7$) mouse T cells in tumor-bearing immunocompetent mice; (2) administering a single dose ($2\times10^6$, $10^7$ and $5\times10^7$) human T cells in human tumor-bearing immunodeficient mice; and (3) administering a single dose ($2\times10^6$, $10^7$ and $5\times10^7$) mouse T cells in tumor-free immunocompetent mice. After obtaining a single dose MTD from these experiments, the following experiments are conducted: (4) administering multi-doses of MTD (mouse T cells) in tumor-bearing immunocompetent mice on days 21, 28 and 32; (5) administering multi-doses of MTD (human T cells) in human cancer-bearing immunodeficient mice (3 times, a week apart); and (6) administering multi-doses of MTD (mouse T cells) in tumor-free immunocompetent mice on days 0, 7 and 14. The results of these experiments define the multi-dose MTD.

These experiments provide a rationale for subsequent development of FSH-targeted CER T cells for the treatment of ovarian cancer. They allow the identification of a lead variant to be used for clinical interventions. To pave the way for immediate clinical testing, we determine the single-infusion maximum tolerated dose (MTD) of our leading FSH-targeted CER. We evaluate tumor-dependent, FSH receptor-specific, and non-specific toxicity after infusion of FSH-targeted CER T cells.

Single Dose Escalation In Vivo in Immunocompetent Mice.

In order to determine single infusion MTD, a single dose escalation is conducted in both tumor- and non-tumor bearing immunocompetent mice. Thus, although the NOD/SCID/γc−/− (NSG) mouse is the best available model for evaluating preclinical efficacy of CER T cells for FSHR-expressing tumors, the mouse tumor xenograft model is a non-relevant species for determination of some aspects of toxicology for this particular CER T cell, because the human FSH component may not bind to normal mouse FSHR, and therefore, this mouse could under-predict toxicity. For this reason, we first use FSH-targeted CER T cell constructs that contain the exact mouse counterpart of each motif identified, to be expressed by murine primary T cells. The goal of these initial experiments is to have a system where the endogenous (mouse FSHR) hormone receptor is present in the ovary and potentially unidentified healthy tissues. These studies test the capacity of the host for orchestrating inflammatory reactions similar to what could be observed in cancer patients in the presence of an intact immune system. Expression of FSH-targeted CER in mouse primary T cells is performed with retroviral vectors independently of the results of Phase I, as lentiviruses do not infect mouse lymphocytes. Doses have been selected based on 5 years of experience with adoptive transfer of T cells in various preclinical models[7,30,43,49,50], including the use of FSH-targeted CER lymphocytes to treat FSHR+ tumors in immunocompetent mice (FIG. 3). The "standard" efficacious and non-toxic dose is $10^7$ cells, though we have shown efficacy below this dose. Mice are infused with $2\times10^6$, $10^7$, or $5\times10^7$ mock-transduced T cells, FSH-targeted CER T cells, or HBSS. Because the expression of the FSHR has been also reported to be present in the altered endothelium found in metastatic lesions (but not in healthy blood vessels)[51], as well as in the epithelial cells in prostate cancer[52], we conduct two independent experiments for each protocol; one used male mice and another used female mice, with 5 mice per group in each experiment. These experiments define toxicity in both genders by not excluding the potential presence of endogenous FSHR in healthy male or female tissues.

In both males and females, FSHR-transduced ID8-Defb29/Vegf-a ovarian cancer cells are administered to generate ovarian tumors disseminated throughout the peritoneal cavity. These tumors, albeit more slowly and slightly less reproducibly, also grow in male mice. Tumor-bearing mice are infused with T cells or HBSS 5 days after tumor injection. Because the standard administration of other CAR T cells in the clinic involves previous lymphodepletion[28], we sublethally irradiate the mice (300 rads) 5 h before T cell adoptive transfer. All tumor cells and T cells are initially infused i.p., because this is the route endorsed by the NCI for targeting ovarian cancer in the clinic[53]. If two or more mice at a particular T cell dose show signs of toxicity, all mice at that dose and paired HBSS treated controls were sacrificed for analysis. In that case, the administration of CER T cells i.v. is evaluated.

Single Dose Escalation In Vivo in Human Ovarian Cancer-Bearing Mice.

These complementary experiments are conducted in OVCAR3 (FSHR+) ovarian cancer-bearing NSG mice, which is the best available model for evaluating preclinical efficacy of CER T cells for FSHR-expressing tumors (survival). FSH-targeted CERs are expressed with the viral vector developed for clinical testing. Monocyte-depleted human T cells from the aphaeresis of HLA-A2+ healthy donors are used for transduction of the (human) FSH-targeted CER T cell variant. Because NSG mice do not have T, NK or B cells, adoptively transferred T cells undergo homeostatic expansion anyway, making lymphodepletion (sublethal irradiation) unnecessary. The goal of these studies is to identify potential side effects restricted to the use of human T cells. For instance human IL-6 is known to signal on mouse receptors and therefore a potential cytokine release syndrome could be detected.

In both sets of experiments, the following readouts are monitored:

The health status of mice is monitored and graded on a scale from 1 to 4:1—normal and healthy; 1.5—some lethargy, walking a bit slowly; 2—moving slowly and a slight dragging of a limb; 2.5—dragging limbs when moving; 3—hunched posture and little movement; 3.5—laying on side, no or little movement upon touch; 4—death. A cohort of mice (≥5/group) is sacrificed between 6 and 20 hours after T cell infusion and their health status is recorded. Potential differences in the presence CER vs. HBSS, and between the presence vs. the absence of tumor are recorded. If mice experienced signs of grade 3-4 health deterioration, serum is collected for quantification of IL-6 circulating levels, as this cytokine is responsible for the cytokine release syndrome observed in some patients.

We also measure and record body weight on each day of T cell infusion and the three subsequent days. We continue to monitor body weight throughout the experiments. If mice experienced >10% of body weight loss in 24 h they are sacrificed. Otherwise, recorded body weight is compared to control mice, and also in the presence vs. the absence of a tumor.

Tissue sections are be analyzed in a blinded manner in all sacrificed mice. The liver, pancreas, spleen, small intestine, large intestine, heart, kidney, and lung are examined for evidence of tissue damage in H&E staining as well as the presence of (CD45+) inflammatory infiltrates by IHC. Leukocyte accumulation in healthy tissues is compared in mice treated with CER T cells vs. HBSS, and also in the presence vs. the absence of tumor. The presence of red blood cells in the alveolar space or airways is additionally monitored to detect acute bleeding.

Survival is monitored in tumor-free vs. tumor-bearing mice receiving a single infusion of CER vs. control T cells. If mice infused with the highest dose ($5 \times 10^7$ cells) of FSH-targeted CER T cells suffer from severe acute toxicity, they are sacrificed regardless of whether they have tumors.

These experiments define the maximum tolerated dose for single infusion of our FSH-targeted T cells.

Maximum Tolerated Dose for Multi-Dose Administrations

The single dose MTD is likely between $2 \times 10^6$ and $5 \times 10^7$ of FSH-targeted CER T cells. To determine the toxicity of multiple FSH-targeted CER T cell administrations analogous to a therapeutic regimen in a clinical setting tumor-dependent, FSH receptor-specific, and non-specific toxicity are evaluated after infusion of FSH-targeted CER T cells. Both human xenografts and immunocompetent mouse systems are used to predict potential side effects in a clinical setting.

To determine whether multiple infusions at this dose would result in toxicity based on in vivo accumulation of T cells or host sensitization, tumor-bearing and non-tumor bearing mice are treated with three infusions of the MTD of CER T cells, the same amount of mock transduced (control) T cells, or HBSS. FSHR-transduced ID8-Defb29/Vegf-a ovarian cancer-bearing immunocompetent mice receive primary mouse T cells transduced with the mouse version of our FSH-targeted CER Immunodeficient mice growing FSHR+HLA-A2+OVCAR3 human ovarian cancer cells are treated with human HLA-A2+FSH-targeted CER T cells. To maximize the probability of tumor-associated toxicity, mice are treated at later time points, once tumors have been established. Mice with orthotopic ID8-Defb29/Vegf-a ovarian tumors start treatment at day 21 after tumor challenge, when ascites becomes evident in the absence of treatment. Injections are repeated 7 days apart (days 28 and 32 after tumor challenge). For OVCAR3 tumor-bearing mice, treatments are initiated when tumors become palpable or are clearly established, as determined by ultrasound. Subsequent injections are administered a week apart. NSG mice receiving human T cells are not expected to show signs of GVHD before 30 days of the first infusion, which provides an evolution time long-enough to define toxicity as a function of effectiveness. By treating tumors at advanced stages, we anticipate a significant survival benefit for mice treated with FSH-targeted CER T cells but we do not expect total tumor elimination. NSG mice treated with human CER T cells are sacrificed at day 28 after the first T cell administration. Again, 5 mice per group are used for each experiment.

The same readouts as described above, i.e., health status, body weight, histology and survival are monitored. We do not expect to identify signs of toxicity after the second and third administrations. We compare how the presence vs. the absence of a tumor influences toxicity. In the unexpected event that significant toxicity is observed upon repeated injections, we escalate down the second and third infusion, starting with 50% of the previously determined MTD, and administering the full dose in the last injection. Subsequent reductions (50%) of the two last injections are tested if toxicity persists. Body weight is assessed starting on the day of each T cell infusion and three subsequent days. We monitor body weight throughout the experiment. We anticipate a slight decrease (~1%) in body weight one day after these infusions, likely reflecting the stress of handling and injection. However, we do not expect major weight losses. If they occur, we escalate down the second and third injections. We collect liver, pancreas, spleen, small intestine, large intestine, heart, kidney, and lung from all sacrificed mice and generate histological sections for analysis of obvious tissue damage and inflammatory infiltrates. Histological patterns after treatment with control vs. CER T cells, and administration in the presence vs. the absence of tumor are compared. Survival is monitored in tumor-free vs. tumor-bearing mice receiving multiple doses of CER vs. control T cells. We do not expect differences in survival of non-tumor bearing mice. However, we anticipate that advanced tumor-bearing mice receiving multiple doses of FSH-targeted CER T cells will exhibit significantly longer survival than those treated with control (mock-transduced) T cells. Survival in all groups is recorded.

Example 16—Evaluation of Biomarkers

The ability to monitor the PK/PD of the infused T cells is important for interpretation of outcomes, determination of mechanism, and identification of potential adverse effects early in the clinic. In addition, an important consideration is that the CER can become immunogenic[31,32]. The expression of an endogenous hormone in our FSH-targeted CER minimizes those potential side effects. Novel epitopes are created at the fusion joint of human signaling domains that are not normally juxtaposed (e.g., the joint regions of CD28 and CD3ζ, or the joint regions of CGα and the hinge region). Immunogenicity of the CER can lead to the rejection of the adoptively-transferred T cells and cause inflammatory reactions. As a means to understand the in vivo function of FSH-targeted CER T cells and those theoretical side effects, we evaluate specific biomarkers of cell activity in the serum. Serum is analyzed using ELISA and standard assays for the following markers:

Cytokines are important predictors of both in vivo activity of CART cells against tumor cells (e.g., tumor lysis) and potential allergic/inflammatory reactions. The following inflammatory cytokines are determined by ELISA in the serum of treated and control mice: IL-6, IFN-γ and TNF-α. From those, IL-6 is expected to show the strongest correlation with obvious behavioral alterations or changes in body weight, based on clinical evidence[54]. We anticipate some increases in at least IL-6 within the first 3 days after CER T cell administration, compared to the infusion of HBSS. This presumed mechanism of toxicity is well-understood in the clinic, and effective interventions (usually steroidal or IL-6 blockers) are known and commonly practiced. These inflammation markers are useful in clinical trials to monitor patients and determine the initial dose. We do not expect sustained elevations of systemic inflammatory cytokines >3 days after treatment, although they are monitored nevertheless. Potential changes are recorded and correlated with clinical responses. These surrogate markers are used for determining the minimal anticipated biological effect level.

Hyperferritinemia, peaking at days 2-3, is another important surrogate marker of a cytokine released syndrome in the clinic[57]. We determine the concentration of serum ferritin in control vs. treated mice, and correlate those levels with health deterioration, weight loss and histological changes.

Creatinine is measured as an indicator of potential damage of renal function. Values in control mice are compared to those in mice receiving FSH-targeted CER T cells. Again, we do not anticipate any kidney damage due to CER T cell administration.

AST is determined as an indicator of potential damage to the liver. Histological analyses of liver tissues are correlated with AST values, including potential tumor growth in the liver, as ovarian cancer is a peritoneal disease. Values in control mice receiving HBSS are compared to those in mice infused with CER T cells. Based on clinical evidence with other CER formulations, we do not expect that treatment with FSH-targeted T cells will adversely affect the liver.

We believe, based on clinical information that an important predictor of long-term protection when targeted tumor determinants are truly specific is the persistence of adoptively transferred T cells. We analyze the accumulation of FSH-targeted CER T cells in lymph nodes, the bone marrow, and tumor tissue (if tumors are not rejected) of different xenograft-bearing NSG mice (≥5/group). By analyzing dissociated lymph nodes and bone marrow at days 7 and 14 after adoptive transfer (before GVHD takes place 56), flow cytometry determines the phenotype of (CD3+, as NSG mice do not have T or B cells) persistent CER T cells in terms of acquisition of memory attributes (CD45RA-CD62L+CCR7+CD122+ lymphocytes). Thus, although immunodeficient mice are likely permissive, the presence of a co-stimulatory domain in transferred human T cells promotes long term engraftment and memory differentiation. This is interpreted as a predictor of subsequent therapeutic effectiveness but may have a reflection in the levels of circulating cytokines.

For additional safety, mass doses much lower than the toxic dose are initially used in mice, although the dose is slowly escalated as patients are monitored for signs of toxicity. In one known study, the maximum tolerated dose (MTD) in human mesothelioma-bearing NSG mice treated with anti-mesothelin CART cells was $50 \times 10^7$ cells/mouse. We anticipate similar or better results, given the specificity of our target. Based on preclinical evidence with different T cell adoptive transfer protocols[7,30,43], administration is up to 3 weekly injections. However, clinical protocols are based on infusing CAR T cells in the course of 3 days[28]. If significant toxicity is observed after the third weekly injection, doses of CER T cells are adjusted for tolerance when administered for 3 consecutive days.

Example 17—Minimal Anticipated Biological Effect Level (MABEL)

The minimum anticipated biological effect level for humans is based on the lowest animal dose or concentration required to produce activity in vivo and/or in vitro data in animal/human systems. MABEL is defined through dose-response data from in vivo studies in human tumor-bearing NSG mice treated with CER T cells. Dose/concentration-effect curves are generated derived from experimental data and extrapolated from animal to human to initiate careful dose escalations. The starting point is the dose that corresponds to the minimal biological effect, using the biomarkers defined above as surrogate markers.

To determine MABEL different NSG mice are challenged with OVCAR3 (FSHR+) ovarian cancer cells injected into the ovarian bursa (n≥5/group). When tumors become palpable and show similar size by ultrasound (~300 mm3), FSH-targeted CERs are expressed with the viral vector in CD3/CD28-expanded human T cells from the aphaeresis of HLA-A2+ healthy donors. A selected (human) FSH-targeted CER T cell variant is transduced and the maximum dose of CER T cells with no observed adverse effects is administered. Control mice receive HBSS. IL-6, IFN-γ, TNF-α and ferritin are again determined in serum at the temporal points where increases are observed (i.e., expected to happen only within the first 3 days). Based on this baseline, different cohorts of tumor-bearing mice are identically treated with doses of CER T cells escalated down by 50%, until any increases in the aforementioned cytokines (compared to control mice) disappears (becomes the same as in the control group). This amount of FSH-targeted CER T cells, calculated in terms of body weight, is used to define the starting dose for human intervention.

Patients currently receive between $10^7$ and $10^8$ T cells transduced with different CER per kg of body weight in ongoing trials[28]. Considering that we have not observed noticeable toxicity in mice at doses of $10^9$/kg of body weight (~$10^7$ CER T cells/mouse; ~30 g/mouse; FIG. 3), we anticipate that a safe initial dose can be adjusted and escalated in different patients to reach a "No Observable Adverse Effect Level" below these amounts. For additional safety, a "split dose" approach to dosing is followed over 3 days, administering CER-transduced T cells using 10% of the total intended on day 0, 30% on day 1 and 60% on day 2, starting 2 days following chemotherapy[28].

We analyze test batches of the initial virus to determine which clone is producing a high titer of FSH-targeted CER virus, by both qPCR analysis and ELISA for human FSH.

We transduce human T cells with this virus, and determine the expression of FSHβ, CD3, CD4 and CD8 by flow cytometry, and IFN-γ production after co-culture with FSHR+OVCAR3 tumor cells (as in FIG. 2). We select the cell clones that produce the highest titers for expansion, testing, and production of the master cell bank. This master cell bank can be used as a source of virus producing cells for additional studies.

We then test the product to assure the safety of biological products including tests for (1) sterility, (2) mycoplasma, and (3) adventitious viral agents, following FDA guidelines.

Example 18—Persistence of CER-T Cells in Peripheral Blood

A Q-PCR assay for determining the trafficking and persistence of adoptively transferred CER T cells in vivo in peripheral blood is defined. Primers and TaqMan probes are designed to span the joints between the sequence of CGα and the transmembrane domains of the CER, which are not naturally present in any cell in patients. In addition, a flow cytometry analysis of transferred CER T cells is optimized based on the detection of FSHβ on transduced (CD3+) T cells, by fluorescently labeling available anti-human FSH antibodies, or using a primary anti-FSH antibody and a fluorescently labeled secondary antibody. Tracking of transferred T cells includes CD4 and CD8 antibodies in the assay, to gain understanding of the mechanisms of therapeutic effectiveness. These reagents are tested in a new cohort of OVCAR3 tumor-bearing NSG mice (≥5) adoptively transferred with A2+ T cells from healthy donors transduced with the clinical grade vector and procedures. This experiment verifies the effectiveness of the new reagent against tumor growth.

The primary toxicity anticipated is whether the T cells will cause inflammation by killing tumor cells that express the target. After setting the starting dose, the conventional dose escalation is conservatively based on 3-fold increments. Because we use endogenous FSH, the risk of anaphylaxis or immune targeting of CAR T cells previously described for xenogeneic (murine) scFvs is negligible. As importantly, the expression of the FSH receptor has been limited to the ovary through millions of years of evolution. Because they are routinely resected in ovarian cancer patients and no other organ should bind the FSH hormone, we expect that FSH-targeted CER T cells represent a safe and effective intervention.

Example 19—Use of TALL Cells as a Universal Platform

CER constructs have been expressed in TALL-103/2 cells and in TALL-104 cells (ATCC CRL11386; U.S. Pat. No. 5,702,702), to re-direct their cytotoxic potential towards FSHR+ tumors through ligand rather than a scFv, but otherwise using the activating domains successfully used against leukemias.

The optimization of TALL-103/2 cells as an universal allogeneic platform is one embodiment, because they grow significantly faster than TALL-104 cells in vitro and therefore will be easier to handle for mass production. We will nevertheless also use TALL-104 cells, which traffic spontaneously to tumor beds. Expressing FSH-targeted chimeric receptors enhances the therapeutic potential of TALL-103/2 and TALL-104 cells, by re-directing their cytotoxic activity towards FSHR+ ovarian cancer cells through its endogenous (non-immunogenic) ligand. Preliminary results show that transduction of our FSH CER empowers TALL-103/2 or TALL-104 cells to kill ovarian cancer cells spontaneously expressing FSHRs significantly more effectively than their mock-transduced counterparts. FSH-targeting CER TALL-cells are able to specifically and effectively kill FSHR expressing ovarian cancer cells and abrogate malignant progression in clinically relevant ovarian cancer models without significant adverse effects. These results are anticipated to translate to ovarian cancer patients in subsequent clinical trials.

We have already transduced and selected TALL-103/2 and TALL-104 cells with pBMN retroviruses encoding human FSHR targeted CERs. To demonstrate that spontaneous (NK-like) cytolytic activity of TALL-103/2 cells can be significantly enhanced through the expression of our FSH-targeted CER, we again performed in vitro cytotoxicity experiments using human ovarian cancer (A2$^+$FSHR$^+$) OVCAR3 cells as targets. As shown in FIG. 12, mock-transduced TALL-103/2 cells showed, as expected, some dose-dependent anti-tumor activity against ovarian cancer cells. However, the expression of our FSH-targeted CER empowered this cell line to eliminate ~60% of tumor cells at effector:target ratios as low as 1:4. These experiments support the potential of re-directing our universal allogeneic platform more specifically against FSHR$^+$ (70%) ovarian tumors through the expression of FSHR CERs. Of note, FSH-targeted CER TALL-103/2 cells grow in our bioreactors as effectively as parental cells. This experiment provided proof-of-concept for a potentially safer and universally accessible system; namely, combining the spontaneous therapeutic activity of TALL-103/2 or TALL 104 cells with the power of our FSH-targeted activating receptor, to maximize their specificity; and their anti-tumor cytotoxic activity.

Importantly, the spontaneous cytotoxic activity of TALL-103/2 cells in the absence of CAR/CER expression is restricted to NK-susceptible targets that express NKG2D ligands, such as K562 and U937 leukemic cells, while healthy cells are completely spared from cytotoxic killing. In addition, TALL-103/2 cells are unlikely to cause GVHD upon administration into patients, because they express a single (γδ) TCR, as it was demonstrated for TALL-104 cells. However, the effector activity of TALL-103/2 cells can be elicited through the activation of CD3 or the administration of IL-2. Together with their faster ex vivo growth in bioreactors, compared to clinically available TALL-104 cells, these attributes make TALL-103/2 cells potentially superior allogenic platforms for re-directing their anti-tumor potential through the expression of our FSH-targeted CERs. However, TALL-104 cells are also desirable for this use as they traffic spontaneously to tumor beds.

Each and every patent, patent application including U.S. Provisional Patent Application 62/059,068, U.S. Provisional Patent Application No. 62/202,824, and any document identified herein and the sequence of any publically available nucleic acid and/or peptide sequence cited throughout the disclosure is expressly incorporated herein by reference in its entirety. Embodiments and variations of this invention other than those specifically disclosed above may be devised by others skilled in the art without departing from the true spirit and scope of the invention. The appended claims include such embodiments and equivalent variations.

REFERENCES

1. Siegel, R., Ma, J., Zou, Z. & Jemal, A. Cancer statistics, 2014. *CA Cancer J Clin* 64, 9-29 (2014).

2. Curiel, T. J., et al. Specific recruitment of regulatory T cells in ovarian carcinoma fosters immune privilege and predicts reduced survival. *Nat Med* 10, 942-949 (2004).
3. Zhang, L., et al. Intratumoral T cells, recurrence, and survival in epithelial ovarian cancer. *N Engl J Med* 348, 203-213 (2003).
4. Cubillos-Ruiz, J. R., et al. Polyethylenimine-based siRNA nanocomplexes reprogram tumor-associated dendritic cells via TLRS to elicit therapeutic antitumor immunity. *J Clin Invest* 119, 2231-2244 (2009).
5. Cubillos-Ruiz, J. R., et al. CD277 is a Negative Co-stimulatory Molecule Universally Expressed by Ovarian Cancer Microenvironmental Cells. *Oncotarget* 1, 329-328 (2010).
6. Huarte, E., et al. Depletion of dendritic cells delays ovarian cancer progression by boosting antitumor immunity. *Cancer Res* 68, 7684-7691 (2008).
7. Nesbeth, Y., et al. CCLS-mediated endogenous antitumor immunity elicited by adoptively transferred lymphocytes and dendritic cell depletion. *Cancer Res* 69, 6331-6338 (2009).
8. Scarlett, U. K., et al. In situ stimulation of CD40 and Toll-like receptor 3 transforms ovarian cancer-infiltrating dendritic cells from immunosuppressive to immunostimulatory cells. *Cancer Res* 69, 7329-7337 (2009).
9. Scarlett, U. K., et al. Ovarian cancer progression is controlled by phenotypic changes in dendritic cells. *J Exp Med* 209, 495-506 (2012).
10. Cubillos-Ruiz, J. R., et al. Reprogramming tumor-associated dendritic cells in vivo using microRNA mimetics triggers protective immunity against ovarian cancer. *Cancer Res* 72, 1683-1693 (2012).
11. Porter, D. L., Levine, B. L., Kalos, M., Bagg, A. & June, C. H. Chimeric antigen receptor-modified T cells in chronic lymphoid leukemia. *N Engl J Med* 365, 725-733 (2011).
12. Maus, M. V., Grupp, S. A., Porter, D. L. & June, C. H. Antibody-modified T cells: CARs take the front seat for hematologic malignancies. *Blood* 123, 2625-2635 (2014).
13. Kalos, M., et al. T cells with chimeric antigen receptors have potent antitumor effects and can establish memory in patients with advanced leukemia. *Sci Transl Med* 3, 95ra73 (2011).
14. Simoni, M., Gromoll, J. & Nieschlag, E. The follicle-stimulating hormone receptor: biochemistry, molecular biology, physiology, and pathophysiology. *Endocr Rev* 18, 739-773 (1997).
15. Vannier, B., Loosfelt, H., Meduri, G., Pichon, C. & Milgrom, E. Anti-human FSH receptor monoclonal antibodies: immunochemical and immunocytochemical characterization of the receptor. *Biochemistry* 35, 1358-1366 (1996).
16. Zhang, X. Y., et al. Follicle-stimulating hormone peptide can facilitate paclitaxel nanoparticles to target ovarian carcinoma in vivo. *Cancer Res* 69, 6506-6514 (2009).
17. Al-Timimi, A., Buckley, C. H. & Fox, H. An immunohistochemical study of the incidence and significance of human gonadotrophin and prolactin binding sites in normal and neoplastic human ovarian tissue. *Br J Cancer* 53, 321-329 (1986).
18. Hall, J. E. Neuroendocrine changes with reproductive aging in women. *Semin Reprod Med* 25, 344-351 (2007).
19. Ramakrishna, V., et al. Naturally occurring peptides associated with HLA-A2 in ovarian cancer cell lines identified by mass spectrometry are targets of HLA-A2-restricted cytotoxic T cells. *Int Immunol* 15, 751-763 (2003).
20. Choi, J. H., Choi, K. C., Auersperg, N. & Leung, P. C. Overexpression of follicle-stimulating hormone receptor activates oncogenic pathways in preneoplastic ovarian surface epithelial cells. *J Clin Endocrinol Metab* 89, 5508-5516 (2004).
21. Jemal, A., et al. Cancer statistics, 2009. *CA Cancer J Clin* 59, 225-249 (2009).
22. Jemal, A., et al. Cancer statistics, 2008. *CA Cancer J Clin* 58, 71-96 (2008).
23. Coukos, G., Conejo-Garcia, J. R., Roden, R. B. & Wu, T C Immunotherapy for gynaecological malignancies. *Expert Opin Biol Ther* 5, 1193-1210 (2005).
24. Conejo-Garcia, J. R., et al. Ovarian carcinoma expresses the NKG2D ligand Letal and promotes the survival and expansion of CD28− antitumor T cells. *Cancer Res* 64, 2175-2182 (2004).
25. Hamanishi, J., et al. Programmed cell death 1 ligand 1 and tumor-infiltrating CD8+T lymphocytes are prognostic factors of human ovarian cancer. *Proc Natl Acad Sci USA* 104, 3360-3365 (2007).
26. Sato, E., et al. Intraepithelial CD8+ tumor-infiltrating lymphocytes and a high CD8+/regulatory T cell ratio are associated with favorable prognosis in ovarian cancer. *Proc Natl Acad Sci USA* 102, 18538-18543 (2005).
27. Urba, W. J. & Longo, D. L. Redirecting T cells. *N Engl J Med* 365, 754-757 (2011).
28. Maude, S. L., et al. Chimeric antigen receptor T cells for sustained remissions in leukemia. *N Engl J Med* 371, 1507-1517 (2014).
29. Huarte, E., et al. PILAR is a novel modulator of human T-cell expansion. *Blood* 112, 1259-1268 (2008).
30. Stephen, T. L., et al. Transforming Growth Factor beta-Mediated Suppression of Antitumor T Cells Requires FoxPl Transcription Factor Expression. *Immunity* 41, 427-439 (2014).
31. Lamers, C. H., et al. Immune responses to transgene and retroviral vector in patients treated with ex vivo-engineered T cells. *Blood* 117, 72-82 (2011).
32. Maus, M. V., et al. T cells expressing chimeric antigen receptors can cause anaphylaxis in humans. *Cancer Immunol Res* 1, 26-31 (2013).
33. Conejo-Garcia, J. R., et al. Tumor-infiltrating dendritic cell precursors recruited by a beta-defensin contribute to vasculogenesis under the influence of Vegf-A. *Nat Med* 10, 950-958 (2004).
34. Rutkowski, M. R., et al. Initiation of metastatic breast carcinoma by targeting of the ductal epithelium with adenovirus-cre: a novel transgenic mouse model of breast cancer. *J Vis Exp* (2014).
35. Song, D. G., et al. In vivo persistence, tumor localization, and antitumor activity of CAR-engineered T cells is enhanced by costimulatory signaling through CD137 (4-1BB). *Cancer Res* 71, 4617-4627 (2011).
36. Milone, M. C., et al. Chimeric receptors containing CD137 signal transduction domains mediate enhanced survival of T cells and increased antileukemic efficacy in vivo. *Mol Ther* 17, 1453-1464 (2009).
37. Heslop, H. E., et al. Long-term outcome of EBV-specific T-cell infusions to prevent or treat EBV-related lymphoproliferative disease in transplant recipients. *Blood* 115, 925-935 (2010).
38. Scholler, J., et al. Decade-long safety and function of retroviral-modified chimeric antigen receptor T cells. *Sci Transl Med* 4, 132ra153 (2012).
39. Biasco, L., et al. Integration profile of retroviral vector in gene therapy treated patients is cell-specific according to gene expression and chromatin conformation of target cell. *EMBO Mol Med* 3, 89-101 (2011).
40. Brentjens, R. J. & Curran, K. J. Novel cellular therapies for leukemia: CAR-modified T cells targeted to the CD19 antigen. Hematology *Am Soc Hematol Educ Program* 2012, 143-151 (2012).
41. Hollyman, D., et al. Manufacturing validation of biologically functional T cells targeted to CD19 antigen for autologous adoptive cell therapy. *J Immunother* 32, 169-180 (2009).
42. Pule, M. A., et al. Virus-specific T cells engineered to coexpress tumor-specific receptors: persistence and anti-tumor activity in individuals with neuroblastoma. *Nat Med* 14, 1264-1270 (2008).
43. Nesbeth, Y. C., et al. CD4+ T cells elicit host immune responses to MHC class II-ovarian cancer through CCL5 secretion and CD40-mediated licensing of dendritic cells. *J Immunol* 184, 5654-5662 (2010).
44. Porter, D. L., et al. A phase 1 trial of donor lymphocyte infusions expanded and activated ex vivo via CD3/CD28 costimulation. *Blood* 107, 1325-1331 (2006).
45. Terakura, S., et al. Generation of CD19-chimeric antigen receptor modified CD8+ T cells derived from virus-specific central memory T cells. *Blood* 119, 72-82 (2012).
46. Maines-Bandiera, S. L., et al. Epithelio-mesenchymal transition in a neoplastic ovarian epithelial hybrid cell line. *Differentiation* 72, 150-161 (2004).
47. Ellis, J. M., et al. Frequencies of HLA-A2 alleles in five U.S. population groups. Predominance Of A*02011 and identification of HLA-A*0231. *Hum Immunol* 61, 334-340 (2000).
48. Ritchie, D. S., et al. Persistence and efficacy of second generation CART cell against the LeY antigen in acute myeloid leukemia. *Mol Ther* 21, 2122-2129 (2013).
49. Amatangelo, M. D., et al. Three-dimensional culture sensitizes epithelial ovarian cancer cells to EZH2 methyltransferase inhibition. *Cell Cycle* 12, 2113-2119 (2013).
50. Nesbeth, Y. & Conejo-Garcia, J. R. Harnessing the effect of adoptively transferred tumor-reactive T cells on endogenous (host-derived) antitumor immunity. *Clin Dev Immunol* 2010, 139304 (2010).
51. Siraj, A., et al. Expression of follicle-stimulating hormone receptor by the vascular endothelium in tumor metastases. *BMC Cancer* 13, 246 (2013).
52. Mariani, S., et al. Expression and cellular localization of follicle-stimulating hormone receptor in normal human prostate, benign prostatic hyperplasia and prostate cancer. *J Urol* 175, 2072-2077; discussion 2077 (2006).
53. Walker, J. L., et al. Intraperitoneal catheter outcomes in a phase III trial of intravenous versus intraperitoneal chemotherapy in optimal stage III ovarian and primary peritoneal cancer: a Gynecologic Oncology Group Study. *Gynecol Oncol* 100, 27-32 (2006).
54. Lee, D. W., et al. T cells expressing CD19 chimeric antigen receptors for acute lymphoblastic leukaemia in children and young adults: a phase 1 dose-escalation trial. *Lancet* (2014).
55. Grupp, S. A., et al. Chimeric antigen receptor-modified T cells for acute lymphoid leukemia. *N Engl J Med* 368, 1509-1518 (2013).
56. Carpenito, C., et al. Control of large, established tumor xenografts with genetically retargeted human T cells containing CD28 and CD137 domains. *Proc Natl Acad Sci USA* 106, 3360-3365 (2009).
57. Teachey, D. T., et al. Cytokine release syndrome after blinatumomab treatment related to abnormal macrophage activation and ameliorated with cytokine-directed therapy. *Blood* 121, 5154-5157 (2013).
58. Barber, A., et al. Chimeric NKG2D receptor-bearing T cells as immunotherapy for ovarian cancer. *Cancer Res* 67, 5003-5008 (2007).
59. Cesano, A. & Santoli, D. Two unique human leukemic T-cell lines endowed with a stable cytotoxic function and a different spectrum of target reactivity analysis and modulation of their lytic mechanisms. *In Vitro Cell Dev Biol* 28A, 648-656 (1992).
60. Brando, C., et al. Receptors and lytic mediators regulating anti-tumor activity by the leukemic killer T cell line TALL-104. *J Leukoc Biol* 78, 359-371 (2005).
61. Visonneau, S., et al. Phase I trial of TALL-104 cells in patients with refractory metastatic breast cancer. *Clin Cancer Res* 6, 1744-1754 (2000).
62. U.S. Pat. No. 5,702,702

The invention claimed is:

1. A method of treating a cancer in a human subject comprising:
   administering to a subject having a tumor that expresses follicle stimulating hormone receptor (FSHR), a modified human T cell that comprises a nucleic acid sequence that encodes a chimeric protein, wherein the chimeric protein comprises a ligand linked to an extracellular hinge domain, a transmembrane domain, a co-stimulatory signaling region, and a signaling endodomain,
   wherein the ligand comprises an FSHβ subunit or a fragment thereof,
   wherein the ligand is capable of binding to FSHR on the tumor that expresses FSHR, and wherein the chimeric protein is capable of activating the modified human T cell.

2. The method according to claim 1, wherein the modified human T cell does not express Forkhead Box Protein (Foxp1).

3. The method according to claim 1, wherein said modified human T cell is an autologous human T cell or natural killer (NK) T cell obtained from the subject or from a bone marrow transplant match for the subject.

4. The method according to claim 1, wherein the tumor is ovarian cancer, cancer of the prostate, breast, colon, pancreas, urinary bladder, kidney, lung, liver, stomach, or testis, or the modified human T-cell binds to cells of blood vessels of either primary or metastatic tumors.

5. The method according to claim 1, further comprising decreasing, ablating or down-regulating expression of Forkhead Box Protein (Foxp1) in said modified human T-cell.

6. The method according to claim 5, wherein the manipulation occurs either
   (a) before a T cell is transfected with the nucleic acid sequence that encodes the chimeric protein; or
   (b) after a T cell is transfected with the nucleic acid sequence that encodes the chimeric protein.

7. The method according to claim 1, further comprising, prior to administration,
   (a) removing T cells from the subject;
   (b) transducing the T cells ex vivo with a vector encoding the chimeric protein; and
   (c) formulating the T cells in a suitable pharmaceutical carrier.

8. The method according to claim 1, further comprising treating the subject with chemotherapy.

9. The method according to claim 1, wherein said modified human T cell is an endogenous or heterologous human T cell or human T cell line.

10. The method according to claim 1, wherein the co-stimulatory domain is selected from a CD27, CD28, 4-1BB (CD137), OX40, CD30, CD40, PD-1, ICOS, lymphocyte function-associated antigen-1 (LFA-1), CD2, CD7, LIGHT, NKG2C, and B7-H3 costimulatory domain.

11. The method according to claim 1, wherein the signaling endodomain is selected from a CD3ζ, TCR ζ, FcR γ, FcR β, CD3γ, CD3δ, CD3ε, CD5, CD22, 25 CD79a, CD79b, and CD66d signaling endodomain.

12. The method according to claim 1, wherein the transmembrane domain is selected from a T-cell receptor, CD28, CD3 epsilon, CD45, CD4, CDS, CD9, CD16, CD22, CD33, CD37, CD64, CDSO, CD86, CD134, CD137, and CD154 transmembrane domain.

13. The method according to claim 1, wherein the ligand further comprises an FSHα subunit.

14. The method according to claim 1, wherein the ligand comprises the FSHβ subunit linked to an FSHα subunit by a linker sequence.

15. The method according to claim 1, wherein the FSHβ subunit is a first FSHβ subunit, wherein the ligand further comprises a second FSHβ subunit and a linker, and wherein the first FSHβ subunit is linked to the second FSHβ subunit by the linker sequence.

16. The method according to claim 1, wherein the ligand comprises an FSHβ subunit fragment.

17. The method according to claim 16, wherein the FSHβ subunit fragment comprises an amino acid sequence selected from the group consisting of amino acids 19-33 of SEQ ID NO: 2, 51-71 of SEQ ID NO:2, 69-83 of SEQ ID NO:2, and 99-113 of SEQ ID NO: 2.

18. The method according to claim 1, wherein the ligand comprises a full length FSHβ subunit.

* * * * *

SEQUENCE LISTING

```
<160> NUMBER OF SEQ ID NOS: 8

<210> SEQ ID NO 1
<211> LENGTH: 1473
<212> TYPE: DNA
<213> ORGANISM: Homo sapiens

<400> SEQUENCE: 1
atgaagacac tccagttttt cttccttttc tgttgctgga aagcaatctg ctgcaatagc      60
tgtgagctga ccaacatcac cattgcaata gagaaagaag aatgtcgttt ctgcataagc     120
atcaacacca cttggtgtgc tggctactgc tacaccaggg atctggtgta taggaccca     180 gccaggccca aaatccagaa aacatgtacc ttcaaggaac tggtatacga aacagtgaga     240
gtgcccggct gtgctcacca tgcagattcc ttgtatacat acccagtggc cacccagtgt     300
cactgtggca agtgtgacag cgacagcact gattgtactg tgcgaggcct ggggcccagc     360
tactgctcct ttggtgaaat gaaagaaggt ggtggttctg gtggtggatc cggtggtggt     420
tctggtggtg gtgctcctga tgtgcaggag acagggtttc accatgttgc ccaggctgct     480
```

| | | |
|---|---|---|
| ctcaaactcc tgagctcaag caatccaccc actaaggcct cccaaagtgc taggattaca | 540 | |
| gattgcccag aatgcacgct acaggaaaac ccattcttct cccagccggg tgccccaata | 600 | |
| cttcagtgca tgggctgctg cttctctaga gcatatccca ctccactaag gtccaagaag | 660 | |
| acgatgttgg tccaaaagaa cgtcacctca gagtccactt gctgtgtagc taaatcatat | 720 | |
| aacagggtca cagtaatggg gggtttcaaa gtggagaacc acacggcgtg ccactgcagt | 780 | |
| acttgttatt atcacaaatc taccacgacg ccagcgccgc gaccaccaac accggcgccc | 840 | |
| accatcgcgt cgcagcccct gtccctgcgc ccagaggcgt gccggccagc ggcgggggc | 900 | |
| gcagtgcaca cgagggggct ggacttcgcc tgtgatatct acatctgggc gcccttggcc | 960 | |
| gggacttgtg gggtccttct cctgtcactg gttatcaccc tttactgcaa acggggcaga | 1020 | |
| aagaaactcc tgtatatatt caaacaacca tttatgagac cagtacaaac tactcaagag | 1080 | |
| gaagatggct gtagctgccg atttccagaa gaagaagaag aggatgtgaa actgagagtg | 1140 | |
| aagttcagca ggagcgcaga cgcccccgcg taccagcagg gccagaacca gctctataac | 1200 | |
| gagctcaatc taggacgaag agaggagtac gatgttttgg acaagagacg tggccgggac | 1260 | |
| cctgagatgg gggaaagcc gagaaggaag aaccctcagg aaggcctgta caatgaactg | 1320 | |
| cagaaagata agatggcgga ggcctacagt gagattggga tgaaaggcga gcgccggagg | 1380 | |
| ggcaaggggc acgatggcct ttaccagggt ctcagtacag ccaccaagga cacctacgac | 1440 | |
| gcccttcaca tgcaggccct gccccctcgc taa | 1473 | |

<210> SEQ ID NO 2
<211> LENGTH: 490
<212> TYPE: PRT
<213> ORGANISM: Homo sapiens

<400> SEQUENCE: 2

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu Gly Gly Gly Ser Gly Gly Gly Ser Gly Gly Gly Ser Gly Gly Gly
    130                 135                 140

Ala Pro Asp Val Gln Glu Thr Gly Phe His His Val Ala Gln Ala Ala
145                 150                 155                 160

Leu Lys Leu Leu Ser Ser Ser Asn Pro Pro Thr Lys Ala Ser Gln Ser
                165                 170                 175

Ala Arg Ile Thr Asp Cys Pro Glu Cys Thr Leu Gln Glu Asn Pro Phe
            180                 185                 190
```

```
Phe Ser Gln Pro Gly Ala Pro Ile Leu Gln Cys Met Gly Cys Cys Phe
            195                 200                 205
Ser Arg Ala Tyr Pro Thr Pro Leu Arg Ser Lys Lys Thr Met Leu Val
    210                 215                 220
Gln Lys Asn Val Thr Ser Glu Ser Thr Cys Cys Val Ala Lys Ser Tyr
225                 230                 235                 240
Asn Arg Val Thr Val Met Gly Gly Phe Lys Val Glu Asn His Thr Ala
                245                 250                 255
Cys His Cys Ser Thr Cys Tyr Tyr His Lys Ser Thr Thr Pro Ala
            260                 265                 270
Pro Arg Pro Pro Thr Pro Ala Pro Thr Ile Ala Ser Gln Pro Leu Ser
            275                 280                 285
Leu Arg Pro Glu Ala Cys Arg Pro Ala Ala Gly Gly Ala Val His Thr
    290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Lys Arg Gly Arg Lys Lys Leu Leu Tyr Ile Phe Lys Gln Pro Phe Met
            340                 345                 350
Arg Pro Val Gln Thr Thr Gln Glu Glu Asp Gly Cys Ser Cys Arg Phe
            355                 360                 365
Pro Glu Glu Glu Glu Gly Gly Cys Glu Leu Arg Val Lys Phe Ser Arg
            370                 375                 380
Ser Ala Asp Ala Pro Ala Tyr Gln Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
            420                 425                 430
Gln Glu Gly Leu Tyr Asn Glu Leu Gln Lys Asp Lys Met Ala Glu Ala
            435                 440                 445
Tyr Ser Glu Ile Gly Met Lys Gly Glu Arg Arg Arg Gly Lys Gly His
450                 455                 460
Asp Gly Leu Tyr Gln Gly Leu Ser Thr Ala Thr Lys Asp Thr Tyr Asp
465                 470                 475                 480
Ala Leu His Met Gln Ala Leu Pro Pro Arg
                485                 490

<210> SEQ ID NO 3
<211> LENGTH: 1365
<212> TYPE: DNA
<213> ORGANISM: Homo sapiens

<400> SEQUENCE: 3
atgaatagct gtgagctgac caacatcacc attgcaatag agaaagaaga atgtcgtttc      60
tgcataagca tcaacaccac ttggtgtgct ggctactgct acaccaggga tctggtgtat     120
aaggacccag ccaggcccaa aatccagaaa acatgtacct tcaaggaact ggtatacgaa     180
acagtgagag tgcccggctg tgctcaccat gcagattcct tgtatacata cccagtggcc     240
acccagtgtc actgtggcaa gtgtgacagc gacagcactg attgtactgt gcgaggcctg     300
gggcccagct actgctcctt tggtgaaatg aaagaaggcg gcggaagcgg aggcggatct     360
gggggaggat ctggcggcgg agctcctgat gtgcaggaga cagggtttca ccatgttgcc     420
```

```
caggctgctc tcaaactcct gagctcaagc aatccaccca ctaaggcctc ccaaagtgct    480
aggattacag attgcccaga atgcacgcta caggaaaaacc cattcttctc ccagccgggt    540
gccccaatac ttcagtgcat gggctgctgc ttctctagag catatcccac tccactaagg    600
tccaagaaga cgatgttggt ccaaaagaac gtcaccctcag agtccacttg ctgtgtagct    660
aaatcatata cagggtcac agtaatgggg ggtttcaaag tggagaacca cacggcgtgc     720
cactgcagta cttgttatta tcacaaatct ggcggcggaa gcggaggcgg atctggggga    780
ggatctggcg gcggaaactt cactataaaa tcattgtcca gacctggaca gccctggtgt    840
gaagcgcagg tcttcttgaa taaaaatctt ttccttcagt acaacagtga caacaacatg    900
gtcaaacctc tgggcctcct ggggaagaag gtatatgcca ccagcacttg gggagaattg    960
acccaaacgc tgggagaagt ggggcgagac ctcaggatgc tcctttgtga catcaaaccc   1020
cagataaaga ccagtgatcc ttccactctg caagtcgaga tgttttgtca acgtgaagca   1080
gaacggtgca ctggtgcatc ctggcagttc gccaccaatg gagagaaatc cctcctcttt   1140
gacgcaatga acatgacctg gacagtaatt aatcatgaag ccagtaagat caaggagaca   1200
tggaagaaag acagagggct ggaaaagtat ttcaggaagc tctcaaaggg agactgcgat   1260
cactggctca gggaattctt agggcactgg gaggcaatgc cagaaccgac agtgtcacca   1320
gtaaatgctt cagatatcca ctggtcttct tctagtctac catag                 1365
```

<210> SEQ ID NO 4
<211> LENGTH: 454
<212> TYPE: PRT
<213> ORGANISM: Homo sapiens

<400> SEQUENCE: 4

```
Met Asn Ser Cys Glu Leu Thr Asn Ile Thr Ile Ala Ile Glu Lys Glu
1               5                   10                  15

Glu Cys Arg Phe Cys Ile Ser Ile Asn Thr Thr Trp Cys Ala Gly Tyr
                20                  25                  30

Cys Tyr Thr Arg Asp Leu Val Tyr Lys Asp Pro Ala Arg Pro Lys Ile
            35                  40                  45

Gln Lys Thr Cys Thr Phe Lys Glu Leu Val Tyr Glu Thr Val Arg Val
        50                  55                  60

Pro Gly Cys Ala His His Ala Asp Ser Leu Tyr Thr Tyr Pro Val Ala
65                  70                  75                  80

Thr Gln Cys His Cys Gly Lys Cys Asp Ser Asp Ser Thr Asp Cys Thr
                85                  90                  95

Val Arg Gly Leu Gly Pro Ser Tyr Cys Ser Phe Gly Glu Met Lys Glu
            100                 105                 110

Gly Gly Gly Ser Gly Gly Gly Ser Gly Gly Ser Gly Gly Gly Ala
        115                 120                 125

Pro Asp Val Gln Glu Thr Gly Phe His His Val Ala Gln Ala Ala Leu
    130                 135                 140

Lys Leu Leu Ser Ser Ser Asn Pro Thr Lys Ala Ser Gln Ser Ala
145                 150                 155                 160

Arg Ile Thr Asp Cys Pro Glu Cys Thr Leu Gln Glu Asn Pro Phe Phe
                165                 170                 175

Ser Gln Pro Gly Ala Pro Ile Leu Gln Cys Met Gly Cys Cys Phe Ser
            180                 185                 190

Arg Ala Tyr Pro Thr Pro Leu Arg Ser Lys Lys Thr Met Leu Val Gln
        195                 200                 205
```

```
Lys Asn Val Thr Ser Glu Ser Thr Cys Cys Val Ala Lys Ser Tyr Asn
    210                 215                 220

Arg Val Thr Val Met Gly Gly Phe Lys Val Glu Asn His Thr Ala Cys
225                 230                 235                 240

His Cys Ser Thr Cys Tyr Tyr His Lys Ser Gly Gly Ser Gly Gly
                245                 250                 255

Gly Ser Gly Gly Gly Ser Gly Gly Asn Phe Thr Ile Lys Ser Leu
            260                 265                 270

Ser Arg Pro Gly Gln Pro Trp Cys Glu Ala Gln Val Phe Leu Asn Lys
            275                 280                 285

Asn Leu Phe Leu Gln Tyr Asn Ser Asp Asn Asn Met Val Lys Pro Leu
    290                 295                 300

Gly Leu Leu Gly Lys Lys Val Tyr Ala Thr Ser Thr Trp Gly Glu Leu
305                 310                 315                 320

Thr Gln Thr Leu Gly Glu Val Gly Arg Asp Leu Arg Met Leu Leu Cys
                325                 330                 335

Asp Ile Lys Pro Gln Ile Lys Thr Ser Asp Pro Ser Thr Leu Gln Val
            340                 345                 350

Glu Met Phe Cys Gln Arg Glu Ala Glu Arg Cys Thr Gly Ala Ser Trp
            355                 360                 365

Gln Phe Ala Thr Asn Gly Glu Lys Ser Leu Leu Phe Asp Ala Met Asn
    370                 375                 380

Met Thr Trp Thr Val Ile Asn His Glu Ala Ser Lys Ile Lys Glu Thr
385                 390                 395                 400

Trp Lys Lys Asp Arg Gly Leu Glu Lys Tyr Phe Arg Lys Leu Ser Lys
                405                 410                 415

Gly Asp Cys Asp His Trp Leu Arg Glu Phe Leu Gly His Trp Glu Ala
            420                 425                 430

Met Pro Glu Pro Thr Val Ser Pro Val Asn Ala Ser Asp Ile His Trp
            435                 440                 445

Ser Ser Ser Ser Leu Pro
    450

<210> SEQ ID NO 5
<211> LENGTH: 1260
<212> TYPE: DNA
<213> ORGANISM: Mus musculus

<400> SEQUENCE: 5
atgcacagct gcgagctgac caacatcacc atcagcgtgg aaaaagagga atgccggttc      60
tgcatcagca tcaacaccac ttggtgcgcc ggctactgct acacccggga cctggtgtac     120
aaggaccccg ccagacccaa cacccagaaa gtgtgcacct tcaaagaact ggtgtacgag     180
acagtgcggc tgcccggctg tgccagacac agcgatagcc tgtacaccta ccccgtggcc     240
accgagtgcc actgcggcaa gtgtgacagc gacagcaccg actgtaccgt gcggggactg     300
ggccctagct actgcagctt cagcgagatg aaggaaggcg gcggaagcgg aggcggatct     360
ggggggagga tctggcggcgg agacttcatt attcaaggct gccccgagtg caagctgaaa     420
gagaacaagt acttcagcaa gctgggcgct cccatctacc agtgcatggg ctgctgcttc     480
agcagagcct accccacccc tgccagatcc aagaaaacca tgctggtgcc caagaacatc     540
acctccgagg ccacctgttg cgtggccaag gccttcacca aggccaccgt gatgggcaac     600
gccagagtgg aaaaccacac agagtgtcac tgcagcacct gttactacca caagagcgct     660
agcggcggcg gaagcggagg cggatctggg ggaggatctg gcggcggacc aaggatagaa     720
```

```
gagactgctt ctctttgtaa catttacaag gttaacaggt cagagtctgg acaacatagt      780
catgaagttc aaggcctact caacagacag cctcttttg tctacaagga taaaaagtgt       840
catgccattg gtgctcatag aacagcatg aatgctacaa agatctgtga aaagaggtt        900 gacactctga agatggaat tgacattttc aaaggtctgc tgcttcacat agtgcaggag       960
actaacacaa ccggaaagcc cctcactctg caggctgagg tgtgtggcca gtatgaagta     1020
gacaaacatt tcacaggata cgccattgtt agcctcaatg aaagaatat attccgtgtt     1080 gacacaagca ctggcaactg gacccaactg gatcatgaat tcgagaagtt tatagaaatg    1140
tgcaaggaag acaaggtttt agctgccttt ttaaagaaga ctacagaggg cgactgcagg    1200
acctggcttg atgagctcat gttgcactgg aaagaacatc tggagcctgc aggatcttag   1260
```

<210> SEQ ID NO 6
<211> LENGTH: 446
<212> TYPE: PRT
<213> ORGANISM: Mus musculus

<400> SEQUENCE: 6

```
Met His Ser Cys Glu Leu Thr Asn Ile Thr Ile Ser Val Glu Lys Glu
1               5                   10                  15

Glu Cys Arg Phe Cys Ile Ser Ile Asn Thr Thr Trp Cys Ala Gly Tyr
            20                  25                  30

Cys Tyr Thr Arg Asp Leu Val Tyr Lys Asp Pro Ala Arg Pro Asn Thr
        35                  40                  45

Gln Lys Val Cys Thr Phe Lys Glu Leu Val Tyr Glu Thr Val Arg Leu
    50                  55                  60

Pro Gly Cys Ala Arg His Ser Asp Ser Leu Tyr Thr Tyr Pro Val Ala
65                  70                  75                  80

Thr Glu Cys His Cys Gly Lys Cys Asp Ser Asp Ser Thr Asp Cys Thr
                85                  90                  95

Val Arg Gly Leu Gly Pro Ser Tyr Cys Ser Phe Ser Glu Met Lys Glu
            100                 105                 110

Gly Gly Gly Ser Gly Gly Gly Ser Gly Gly Gly Ser Gly Gly Gly Asp
        115                 120                 125

Phe Ile Ile Gln Gly Cys Pro Glu Cys Lys Leu Lys Glu Asn Lys Tyr
    130                 135                 140

Phe Ser Lys Leu Gly Ala Pro Ile Tyr Gln Cys Met Gly Cys Cys Phe
145                 150                 155                 160

Ser Arg Ala Tyr Pro Thr Pro Ala Arg Ser Lys Lys Thr Met Leu Val
                165                 170                 175

Pro Lys Asn Ile Thr Ser Glu Ala Thr Cys Cys Val Ala Lys Ala Phe
            180                 185                 190

Thr Lys Ala Thr Val Met Gly Asn Ala Arg Val Glu Asn His Thr Glu
        195                 200                 205

Cys His Cys Ser Thr Cys Tyr Tyr His Lys Ser Ala Ser Gly Gly Gly
    210                 215                 220

Ser Gly Gly Gly Ser Gly Gly Ser Gly Gly Gly Pro Arg Ile Glu
225                 230                 235                 240

Glu Thr Ala Ser Leu Cys Asn Ile Tyr Lys Val Asn Arg Ser Glu Ser
                245                 250                 255

Gly Gln His Ser His Glu Val Gln Gly Leu Leu Asn Arg Gln Pro Leu
            260                 265                 270

Phe Val Tyr Lys Asp Lys Lys Cys His Ala Ile Gly Ala His Arg Asn
        275                 280                 285
```

```
Ser Met Asn Ala Thr Lys Ile Cys Glu Lys Glu Val Asp Thr Leu Lys
    290                 295                 300
Asp Gly Ile Asp Ile Phe Lys Gly Leu Leu His Ile Val Gln Glu
305                 310                 315                 320
Thr Asn Thr Thr Gly Lys Pro Leu Thr Leu Gln Ala Glu Val Cys Gly
                325                 330                 335
Gln Tyr Glu Val Asp Lys His Phe Thr Gly Tyr Ala Ile Val Ser Leu
            340                 345                 350
Asn Gly Lys Asn Ile Phe Arg Val Asp Thr Ser Thr Gly Asn Trp Thr
        355                 360                 365
Gln Leu Asp His Glu Phe Glu Lys Phe Ile Glu Met Cys Lys Glu Asp
    370                 375                 380
Lys Val Leu Ala Ala Phe Leu Lys Lys Thr Thr Glu Gly Asp Cys Arg
385                 390                 395                 400
Thr Trp Leu Asp Glu Leu Met Leu His Trp Lys Gly Ala Ala Cys Ala
                405                 410                 415
Thr Cys Thr Gly Gly Ala Gly Cys Cys Thr Gly Cys Ala Gly Gly Ala
            420                 425                 430
Thr Cys Thr Thr Ala Gly Glu His Leu Glu Pro Ala Gly Ser
        435                 440                 445
```

<210> SEQ ID NO 7
<211> LENGTH: 1272
<212> TYPE: DNA
<213> ORGANISM: Homo sapiens

<400> SEQUENCE: 7

```
atgaatagct gtgagctgac caacatcacc attgcaatag agaaagaaga atgtcgtttc    60
tgcataagca tcaacaccac ttggtgtgct ggctactgct acaccaggga tctggtgtat   120
aaggacccag ccaggcccaa atccagaaaa catgtacctt caaggaact ggtatacgaa    180
acagtgagag tgcccggctg tgctcaccat gcagattcct tgtatacata cccagtggcc   240
acccagtgtc actgtggcaa gtgtgacagc gacagcactg attgtactgt gcgaggcctg   300
gggcccagct actgctcctt tggtgaaatg aagaaggcg gcggaagcgg aggcggatct   360
gggggaggat ctggcggcgg agctcctgat gtgcaggatt gcccagaatg cacgctacag   420
gaaaacccat tcttctccca gccgggtgcc caatacttc agtgcatggg ctgctgcttc   480
tctagagcat atcccactcc actaaggtcc aagaagacga tgttggtcca aagaacgtc    540
acctcagagt ccacttgctg tgtagctaaa tcatataaca gggtcacagt aatggggggt   600
ttcaaagtgg agaaccacac ggcgtgccac tgcagtactt gttattatca caatctggc    660
ggcggaagcg gaggcggatc tggggagga tctggcggcg gaaacttcac tataaaatca   720
ttgtccagac tggacagcc ctggtgtgaa gcgcaggtct tcttgaataa aaatcttttc    780
cttcagtaca cagtgacaa caacatggtc aaacctctgg gcctcctggg gaagaaggta    840
tatgccacca gcacttgggg agaattgacc caaacgctgg agaagtggg gcgagacctc    900
aggatgctcc tttgtgacat caaaccccag ataaagacca gtgatcttc cactctgcaa   960
gtcgagatgt tttgtcaacg tgaagcagaa cggtgcactg tgcatcctg cagttcgcc   1020
accaatggag agaatccct cctctttgac gcaatgaaca tgacctggac agtaattaat   1080
catgaagcca gtaagatcaa ggagacatgg aagaaagaca gagggctgga aaagtatttc   1140
aggaagctct caaagggaga ctgcgatcac tggctcaggg aattcttagg gcactgggag   1200
```

```
gcaatgccag aaccgacagt gtcaccagta aatgcttcag atatccactg gtcttcttct    1260
agtctaccat ag                                                        1272
```

<210> SEQ ID NO 8
<211> LENGTH: 423
<212> TYPE: PRT
<213> ORGANISM: Homo sapiens

<400> SEQUENCE: 8

```
Met Asn Ser Cys Glu Leu Thr Asn Ile Thr Ile Ala Ile Glu Lys Glu
1               5                  10                  15

Glu Cys Arg Phe Cys Ile Ser Ile Asn Thr Thr Trp Cys Ala Gly Tyr
                20                  25                  30

Cys Tyr Thr Arg Asp Leu Val Tyr Lys Asp Pro Ala Arg Pro Lys Ile
            35                  40                  45

Gln Lys Thr Cys Thr Phe Lys Glu Leu Val Tyr Glu Thr Val Arg Val
        50                  55                  60

Pro Gly Cys Ala His His Ala Asp Ser Leu Tyr Thr Tyr Pro Val Ala
65                  70                  75                  80

Thr Gln Cys His Cys Gly Lys Cys Asp Ser Asp Ser Thr Asp Cys Thr
                85                  90                  95

Val Arg Gly Leu Gly Pro Ser Tyr Cys Ser Phe Gly Glu Met Lys Glu
            100                 105                 110

Gly Gly Gly Ser Gly Gly Gly Ser Gly Gly Gly Ser Gly Gly Gly Ala
        115                 120                 125

Pro Asp Val Gln Asp Cys Pro Glu Cys Thr Leu Gln Glu Asn Pro Phe
130                 135                 140

Phe Ser Gln Pro Gly Ala Pro Ile Leu Gln Cys Met Gly Cys Cys Phe
145                 150                 155                 160

Ser Arg Ala Tyr Pro Thr Pro Leu Arg Ser Lys Lys Thr Met Leu Val
                165                 170                 175

Gln Lys Asn Val Thr Ser Glu Ser Thr Cys Cys Val Ala Lys Ser Tyr
            180                 185                 190

Asn Arg Val Thr Val Met Gly Gly Phe Lys Val Glu Asn His Thr Ala
        195                 200                 205

Cys His Cys Ser Thr Cys Tyr Tyr His Lys Ser Gly Gly Ser Gly
    210                 215                 220

Gly Gly Ser Gly Gly Ser Gly Gly Gly Asn Phe Thr Ile Lys Ser
225                 230                 235                 240

Leu Ser Arg Pro Gly Gln Pro Trp Cys Glu Ala Gln Val Phe Leu Asn
                245                 250                 255

Lys Asn Leu Phe Leu Gln Tyr Asn Ser Asp Asn Asn Met Val Lys Pro
            260                 265                 270

Leu Gly Leu Leu Gly Lys Lys Val Tyr Ala Thr Ser Thr Trp Gly Glu
        275                 280                 285

Leu Thr Gln Thr Leu Gly Glu Val Gly Arg Asp Leu Arg Met Leu Leu
    290                 295                 300

Cys Asp Ile Lys Pro Gln Ile Lys Thr Ser Asp Pro Ser Thr Leu Gln
305                 310                 315                 320

Val Glu Met Phe Cys Gln Arg Glu Ala Glu Arg Cys Thr Gly Ala Ser
                325                 330                 335

Trp Gln Phe Ala Thr Asn Gly Glu Lys Ser Leu Leu Phe Asp Ala Met
            340                 345                 350
```

```
Asn Met Thr Trp Thr Val Ile Asn His Glu Ala Ser Lys Ile Lys Glu
        355                 360                 365

Thr Trp Lys Lys Asp Arg Gly Leu Glu Lys Tyr Phe Arg Lys Leu Ser
    370                 375                 380

Lys Gly Asp Cys Asp His Trp Leu Arg Glu Phe Leu Gly His Trp Glu
385                 390                 395                 400

Ala Met Pro Glu Pro Thr Val Ser Pro Val Asn Ala Ser Asp Ile His
                405                 410                 415

Trp Ser Ser Ser Ser Leu Pro
            420
```

UNITED STATES PATENT AND TRADEMARK OFFICE
CERTIFICATE OF CORRECTION

PATENT NO. : 10,259,855 B2
APPLICATION NO. : 15/515442
DATED : April 16, 2019
INVENTOR(S) : Alfredo Perales-Puchalt and Jose R. Conejo-Garcia Page 1 of 1

It is certified that error appears in the above-identified patent and that said Letters Patent is hereby corrected as shown below:

In the Claims

Column 54, Lines 29-32, Claim 11, (approx.) should read:
-- 11. The method according to claim 1, wherein the signaling endodomain is selected from a CD3 ζ, TCR ζ, FcR γ, FcR β, CD3γ, CD3 δ, CD3 ε, CD5, CD22, CD79a, CD79b, and CD66d signaling endodomain. --

Column 54, Lines 33-37, Claim 12, (approx.) should read:
-- 12. The method according to claim 1, wherein the transmembrane domain is selected from a T-cell receptor, CD28, CD3 epsilon, CD45, CD4, CD8, CD9, CD16, CD22, CD33, CD37, CD64, CD80, CD86, CD134, CD137, and CD154 transmembrane domain. --

Signed and Sealed this
Twenty-seventh Day of August, 2019

Andrei Iancu
*Director of the United States Patent and Trademark Office*